US008415082B2

(12) United States Patent
Utsumi et al.

(10) Patent No.: US 8,415,082 B2
(45) Date of Patent: *Apr. 9, 2013

(54) RESIST COMPOSITION, METHOD OF FORMING RESIST PATTERN, COMPOUND AND METHOD OF PRODUCING THE SAME, ACID GENERATOR

(75) Inventors: Yoshiyuki Utsumi, Kawasaki (JP); Takehiro Seshimo, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 158 days.

This patent is subject to a terminal disclaimer.

(21) Appl. No.: 12/765,590

(22) Filed: Apr. 22, 2010

(65) Prior Publication Data

US 2010/0273105 A1    Oct. 28, 2010

(30) Foreign Application Priority Data

Apr. 27, 2009    (JP) ................................ P2009-107917

(51) Int. Cl.
*G03C 1/00*    (2006.01)
*G03F 7/00*    (2006.01)

(52) U.S. Cl.
USPC ........................................ 430/270.1; 430/325

(58) Field of Classification Search ........ 430/270.1–326; 558/52, 59, 61
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,949,325 B2 | 9/2005 | Li et al. | |
| 7,074,543 B2 | 7/2006 | Iwai et al. | |
| 7,252,924 B2 | 8/2007 | Yamanaka et al. | |
| 7,323,287 B2 | 1/2008 | Iwai et al. | |
| 7,335,454 B2 | 2/2008 | Kanna et al. | |
| 7,384,726 B2 | 6/2008 | Lin et al. | |
| 7,579,497 B2 | 8/2009 | Harada et al. | |
| 7,682,772 B2 | 3/2010 | Seshimo et al. | |
| 7,713,679 B2 | 5/2010 | Ishiduka et al. | |
| 7,767,984 B2 | 8/2010 | Lin et al. | |
| 7,771,914 B2 | 8/2010 | Hatakeyama et al. | |
| 7,816,072 B2 | 10/2010 | Shimbori | |
| 8,012,669 B2* | 9/2011 | Shimizu et al. | 430/270.1 |
| 2001/0049073 A1 | 12/2001 | Hada et al. | |
| 2003/0113658 A1 | 6/2003 | Ebata et al. | |
| 2006/0008736 A1 | 1/2006 | Kanda et al. | |
| 2006/0040203 A1 | 2/2006 | Kodama et al. | |
| 2007/0078269 A1 | 4/2007 | Harada et al. | |
| 2007/0100158 A1 | 5/2007 | Harada et al. | |
| 2007/0100159 A1 | 5/2007 | Yoshida et al. | |
| 2007/0111138 A1 | 5/2007 | Rahman et al. | |
| 2008/0096134 A1 | 4/2008 | Sugimoto et al. | |
| 2008/0138742 A1 | 6/2008 | Kodama et al. | |
| 2008/0248422 A1 | 10/2008 | Iwai et al. | |
| 2008/0311522 A1 | 12/2008 | Iwai et al. | |
| 2009/0042131 A1 | 2/2009 | Shiono et al. | |
| 2009/0068591 A1 | 3/2009 | Kawaue et al. | |
| 2009/0162788 A1* | 6/2009 | Hada et al. | 430/285.1 |
| 2009/0197197 A1 | 8/2009 | Shimizu et al. | |
| 2009/0253081 A1 | 10/2009 | Abdallah et al. | |
| 2010/0015552 A1* | 1/2010 | Kawaue et al. | 430/281.1 |
| 2010/0119974 A1* | 5/2010 | Hada et al. | 430/281.1 |
| 2012/0009521 A1* | 1/2012 | Kawaue et al. | 430/281.1 |

FOREIGN PATENT DOCUMENTS

| | | |
|---|---|---|
| EP | 1 600 437 A | 11/2005 |
| GB | 1 431 251 A | 4/1976 |
| JP | H08-157451 | 6/1996 |
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2000-206694 | 7/2000 |
| JP | 2001-255647 | 9/2001 |

(Continued)

OTHER PUBLICATIONS

Office Action issued in U.S. Appl. No. 12/265,607 on Jun. 29, 2009.
Office Action issued in U.S. Appl. No. 12/400,203 on Dec. 2, 2010.
Office Action issued in U.S. Appl. No. 12/692,513 on Dec. 28, 2011.
Supplemental European Search Report issued for counterpart European Patent Application No. 08168403.7, dated Mar. 3, 2009.
Date-stamped correspondence acknowledging receipt of European Search Report issued for counterpart European Patent Application No. 08168403.7, by Applicant, dated Mar. 23, 2009.
Office Action (Notice of Allowance) issued in counterpart Korean Patent Application No. 10-2008-0113890, dated Feb. 23, 2011.

(Continued)

*Primary Examiner* — Cynthia Kelly
*Assistant Examiner* — Connie P Johnson
(74) *Attorney, Agent, or Firm* — Knobbe Martens Olson & Bear LLP

(57) ABSTRACT

A resist composition including a base material component (A) which exhibits changed solubility in an alkali developing solution under action of acid, and an acid generator component (B) which generates acid upon exposure,
the acid generator component (B) including an acid generator (B1) consisting of a compound represented by general formula (b1-1) shown below:

[Chemical Formula 1]

$$\left[ R^X - \underset{\underset{O}{\|}}{\overset{\overset{O}{\|}}{S}} - O - R^1 - O - \overset{\overset{O}{\|}}{C} - Y^1 - SO_3^- \right]_n \cdot Z \quad (b1\text{-}1)$$

wherein $R^X$ represents a hydrocarbon group which may have a hetero atom; $R^1$ represents a divalent linking group; $Y^1$ represents an alkylene group of 1 to 4 carbon atoms or a fluorinated alkylene group of 1 to 4 carbon atoms; n represents an integer of 1 to 3; and Z represents an organic cation (exclusive of an amine ion and a quaternary ammonium ion) having a valence of n.

7 Claims, No Drawings

FOREIGN PATENT DOCUMENTS

| | | |
|---|---|---|
| JP | 2003-241385 | 8/2003 |
| JP | 2005-037888 | 2/2005 |
| JP | A-2005-266766 | 9/2005 |
| JP | 2005-336452 | 12/2005 |
| JP | A-2006-048029 | 2/2006 |
| JP | 2006-259582 | 9/2006 |
| JP | 2006-317803 | 11/2006 |
| JP | A 2007-145823 | 6/2007 |
| JP | A 2007-145824 | 6/2007 |
| JP | 2008-107377 | 5/2008 |
| JP | 2009-019028 | 1/2009 |
| JP | 2009-515944 | 4/2009 |
| WO | WO 2004-074242 | 9/2004 |
| WO | WO 2006/120896 A1 | 11/2006 |

OTHER PUBLICATIONS

Office Action issued in Taiwanese Patent Application No. 097142516 on Aug. 13, 2012.

Office Action issued in corresponding Japanese Patent Application No. 2009-046064 on Jan. 29, 2013.

* cited by examiner

US 8,415,082 B2

RESIST COMPOSITION, METHOD OF FORMING RESIST PATTERN, COMPOUND AND METHOD OF PRODUCING THE SAME, ACID GENERATOR

BACKGROUND OF THE INVENTION

1. Field of the Invention

The present invention relates to a resist composition containing a novel acid generator, a method of forming a resist pattern using the resist composition, an acid generator for a resist composition or a novel compound useful as a precursor of the acid generator, and a method of producing the compound.

Priority is claimed on Japanese Patent Application No. 2009-107917, filed Apr. 27, 2009, the content of which is incorporated herein by reference.

2. Description of the Related Art

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization. Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X ray.

As shortening of the wavelength of the exposure light source progresses, it is required to improve various lithography properties of the resist material, such as the sensitivity to the exposure light source and the resolution capable of reproducing patterns of minute dimensions. As a resist material which satisfies these conditions, a chemically amplified resist composition is known, which includes a base material component that exhibits a changed solubility in an alkali developing solution under the action of acid and an acid generator component that generates acid upon exposure.

Conventionally, resins have been used as the base material components within these types of chemically amplified resist compositions, and examples of these resins include polyhydroxystyrene (PHS), PHS-based resins in which a portion of the hydroxyl groups of a PHS have been protected with acid dissociable, dissolution inhibiting groups, copolymers derived from (meth)acrylate esters, and resins in which a portion of the carboxyl groups within these (meth)acrylate esters have been protected with acid dissociable, dissolution inhibiting groups (for example, refer to Patent Document 1). Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

As acid generators, various types have been proposed including, for example, onium salt-based acid generators; oxime sulfonate-based acid generators; diazomethane-based acid generators; nitrobenzylsulfonate-based acid generators; iminosulfonate-based acid generators; and disulfone-based acid generators. Of these, as an onium salt-based acid generator, iodonium salts containing iodonium ions as cations and sulfonium salts containing sulfonium ions as cations have conventionally been used. Further, as an anion (acid) that forms a salt with these cations, a perfluoroalkylsulfonic acid ion is generally used (for example, refer to Patent Document 2).

However, a perfluoroalkyl chain of 6 or more carbon atoms is hardly decomposable, and hence, in consideration of minimizing bioaccumulation to improve safety in handling, a perfluoroalkylsulfonic acid ion of no more than 4 carbon atoms such as a nonafluorobutanesulfonic acid ion or the like has been mainly used as the above-mentioned perfluoroalkylsulfonic acid ions.

[Patent Document 1] Japanese Unexamined Patent Application, First Publication No. 2003-241385

[Patent Document 2] Japanese Unexamined Patent Application, First Publication No. 2005-037888

SUMMARY OF THE INVENTION

As the lithography techniques advance even further and the miniaturization of resist patterns continues to progress in future, further improvements in various lithography properties have been required with the resist materials. Examples of those lithography properties that are required to improve include the so-called exposure margin (EL margin) and mask error factor (MEF). The exposure margin (EL margin) is the range of the exposure dose at which a resist pattern can be formed with a size within a predetermined range of variation from a target size, when exposure is conducted by changing the exposure dose, i.e., the range of the exposure dose at which a resist pattern faithful to the mask pattern can be formed. The larger the exposure margin, the smaller the amount of change in the pattern size depending on the change in the exposure dose. The MEF is a parameter that indicates how faithfully mask patterns of differing dimensions can be reproduced (mask reproducibility) by using the same exposure dose with fixed pitch and changing the mask pattern size (namely, the hole diameter in hole patterns and the line width in line and space patterns). The closer the MEF value is to 1, the better the mask reproducibility.

Therefore, development of a compound containing a novel anion which improves these lithography properties and is more useful as an acid generator for a resist composition has been demanded.

The present invention takes the above circumstances into consideration, with an object of providing a resist composition containing a novel acid generator, a method of forming a resist pattern using the resist composition, an acid generator for a resist composition or a novel compound useful as a precursor of the acid generator, and a method of producing the compound.

A first aspect of the present invention which solves the above-mentioned problems is a resist composition including a base material component (A) which exhibits changed solubility in an alkali developing solution under action of acid and an acid generator component (B) which generates acid upon exposure, the acid generator component (B) including an acid generator (B1) consisting of a compound represented by general formula (b1-1) shown below.

Further, a second aspect of the present invention is a method of forming a resist pattern, including: applying a resist composition of the first aspect to a substrate to form a resist film on the substrate; subjecting the resist film to exposure, and subjecting the resist film to alkali developing to form a resist pattern.

[Chemical Formula 1]

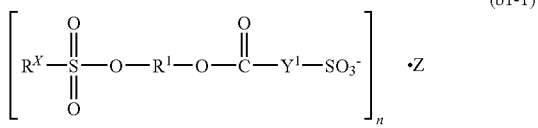

(b1-1)

[In the formula, $R^X$ represents a hydrocarbon group which may have a hetero atom; $R^1$ represents a divalent linking group; $Y^1$ represents an alkylene group of 1 to 4 carbon atoms or a fluorinated alkylene group of 1 to 4 carbon atoms; n represents an integer of 1 to 3; and Z represents an organic cation (exclusive of an amine ion and a quaternary ammonium ion) having a valence of n.]

A third aspect of the present invention is a compound having an anion represented by general formula (I) shown below.

Further, a fourth aspect of the present invention is a compound represented by general formula (b1-1) shown below, and a fifth aspect of the present invention is a compound represented by general formula (b0-1) shown below.

[Chemical Formula 2]

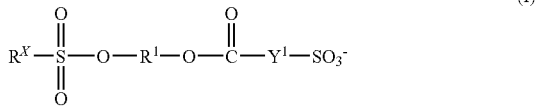

(I)

[In the formula, $R^X$ represents a hydrocarbon group which may have a hetero atom; $R^1$ represents a divalent linking group; and $Y^1$ represents an alkylene group of 1 to 4 carbon atoms or a fluorinated alkylene group of 1 to 4 carbon atoms.]

[Chemical Formula 3]

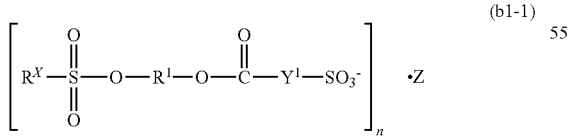

(b1-1)

[In the formula, $R^X$ represents a hydrocarbon group which may have a hetero atom; $R^1$ represents a divalent linking group; $Y^1$ represents an alkylene group of 1 to 4 carbon atoms or a fluorinated alkylene group of 1 to 4 carbon atoms; n represents an integer of 1 to 3; and Z represents an organic cation (exclusive of an amine ion and a quaternary ammonium ion) having a valence of n.]

[Chemical Formula 4]

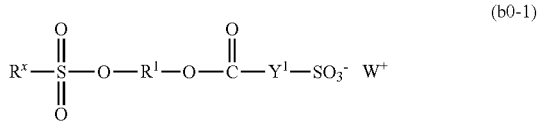

(b0-1)

[In the formula, $R^X$ represents a hydrocarbon group which may have a hetero atom; $R^1$ represents a divalent linking group; $Y^1$ represents an alkylene group of 1 to 4 carbon atoms or a fluorinated alkylene group of 1 to 4 carbon atoms; and $W^+$ represents an alkali metal ion, an amine ion or a quaternary ammonium ion.]

A sixth aspect of the present invention is a method of producing a compound according to the fourth aspect, and is a production method that includes a step of reacting a compound represented by general formula (b0-1) shown below with a compound represented by general formula (b0-2) shown below.

Further, a seventh aspect of the present invention is a method of producing a compound according to the fifth aspect, and is a production method that includes a step of reacting a compound represented by general formula (1-11) shown below with a compound represented by general formula (1-12) shown below under the presence of an alkali metal hydroxide, an amine or a quaternary ammonium salt.

[Chemical Formula 5]

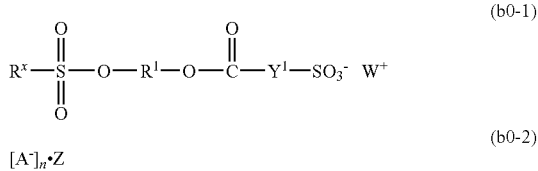

(b0-1)

(b0-2)

[In the formula, $R^X$, $R^1$, $Y^1$, n and Z are the same as defined above; $W^+$ represents an alkali metal ion, an amine ion or a quaternary ammonium ion; and $A^-$ represents a counter anion.]

[Chemical Formula 6]

(1-11)

(1-12)

[In the formulas, $R^X$, $R^1$ and $Y^1$ are the same as defined above; $W'^+$ represents an alkali metal ion, an amine ion or a quaternary ammonium ion; and $X^{21}$ represents a halogen atom.]

An eighth aspect of the present invention is an acid generator including the compound of the fourth aspect.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon groups, unless otherwise specified.

The term "alkylene group" includes linear, branched or cyclic divalent saturated hydrocarbon groups, unless otherwise specified. The same applies for the alkyl group within an alkoxy group.

A "halogenated alkyl group" is a group in which part or all of the hydrogen atoms of an alkyl group is substituted with halogen atoms. Examples of the halogen atoms include fluorine atoms, chlorine atoms, bromine atoms and iodine atoms.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a resin component (polymer).

The term "exposure" is used as a general concept that includes irradiation with any form of radiation.

According to the present invention, there are provided a resist composition containing a novel acid generator, a method of forming a resist pattern using the resist composition, an acid generator for a resist composition or a novel compound useful as a precursor of the acid generator, and a method of producing the compound.

DETAILED DESCRIPTION OF THE INVENTION

<<Compound and Production Method Thereof>>

A compound according to the third aspect of the present invention is a compound having an anion (hereafter, frequently referred to as "anion (I)") represented by general formula (I) shown below.

[Chemical Formula 7]

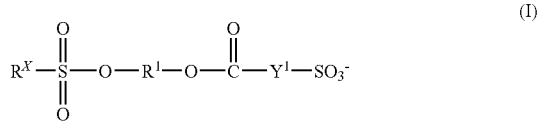

(I)

[In the formula, $R^X$ represents a hydrocarbon group which may have a hetero atom; $R^1$ represents a divalent linking group; and $Y^1$ represents an alkylene group of 1 to 4 carbon atoms or a fluorinated alkylene group of 1 to 4 carbon atoms.]

In formula (I), a "hetero atom" which the hydrocarbon group for $R^X$ may have refers to an atom other than a carbon atom and a hydrogen atom, and examples thereof include an oxygen atom, a sulfur atom, a nitrogen atom and a halogen atom. Examples of the halogen atom include a fluorine atom, a chlorine atom, a bromine atom and an iodine atom.

The hydrocarbon group for $R^X$ may be either an aliphatic hydrocarbon group, or an aromatic hydrocarbon group.

Further, the aliphatic hydrocarbon group may be a saturated aliphatic hydrocarbon group or an unsaturated aliphatic hydrocarbon group, or a combination thereof. Further, the aliphatic hydrocarbon group may be any of linear, branched or cyclic.

In the aliphatic hydrocarbon group, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom. Hereafter, a "substituent group containing a hetero atom" may be referred to as a "hetero atom-containing substituent".

As the hetero atom within the hetero atom-containing substituent, the same hetero atoms as those described above can be used.

The hetero atom-containing substituent may consist solely of the hetero atoms described above, or may be a group containing a group or atom other than the hetero atoms described above.

Specific examples of the hetero atom-containing substituent which may substitute a part of the carbon atoms constituting the aliphatic hydrocarbon group include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—, and the like. When the hetero atom-containing substituent is —NH— and the H in the formula is replaced with a substituent (such as an alkyl group or an acyl group), the substituent preferably has 1 to 10 carbon atoms, more preferably 1 to 8 carbon atoms, and most preferably 1 to 5 carbon atoms.

When the aliphatic hydrocarbon group is cyclic, the aliphatic hydrocarbon group may contain any of these substituent groups in the ring structure.

Examples of the hetero atom-containing substituent which may substitute a part or all of the hydrogen atoms constituting the aliphatic hydrocarbon group include a halogen atom, an alkoxy group, a hydroxyl group, —C(=O)—$R^{90}$ [wherein $R^{90}$ represents an alkyl group], —COO$R^{91}$ [wherein $R^{91}$ represents a hydrogen atom or an alkyl group], a halogenated alkyl group, a halogenated alkoxy group, an amino group, an amide group, a nitro group, an oxygen atom (=O), a sulfur atom and a sulfonyl group (SO$_2$).

Examples of the halogen atom as the hetero atom-containing substituent include a fluorine atom, a chlorine atom, a bromine atom and an iodine atom, and a fluorine atom is preferable.

The alkyl group within the alkoxy group as the hetero atom-containing substituent may be a linear, branched or cyclic group, or may be a combination thereof. The number of carbon atoms within the alkyl group is preferably within a range of from 1 to 30.

When the alkyl group is a linear or branched alkyl group, it preferably has 1 to 20 carbon atoms, more preferably 1 to 17 carbon atoms, still more preferably 1 to 15 carbon atoms, and most preferably 1 to 10 carbon atoms. Specific examples of the alkyl group include the same groups as those for the linear or branched saturated hydrocarbon group described below.

When the alkyl group is a cyclic alkyl group (cycloalkyl group), it preferably has 3 to 30 carbon atoms, more preferably 3 to 20 carbon atoms, still more preferably 3 to 15 carbon atoms, still more preferably 4 to 12 carbon atoms, and most preferably 5 to 10 carbon atoms. The alkyl group may be either a monocyclic group or a polycyclic group. Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples of the monocycloalkane include cyclopentane and cyclohexane. Further, specific examples of the polycycloalkane include adamantane, norbornane, isobornane, tricyclodecane and tetracyclododecane. In these cycloalkyl groups, part or all of the hydrogen atoms boned to the ring may or may not be substituted with a substituent such as a fluorine atom and a fluorinated alkyl group.

With respect to —C(=O)—$R^{90}$ and —COO$R^{91}$ as the hetero atom-containing substituent, as the alkyl group for $R^{90}$ and R$^{91}$, the same alkyl groups as those described above as the alkyl group within the alkoxy group can be used.

Examples of the alkyl group within the halogenated alkyl group as the hetero atom-containing substituent include the same alkyl groups as those described above as the alkyl group within the alkoxy group. As the halogenated alkyl group, a fluorinated alkyl group is particularly desirable.

Examples of the halogenated alkoxy group as the hetero atom-containing substituent include a group in which part or all of the hydrogen atoms within the aforementioned alkoxy group have been substituted with the aforementioned halogen atoms. As the halogenated alkoxy group, a fluorinated alkoxy group is preferable.

Examples of the hydroxyalkyl group as the hetero atom-containing substituent include a group in which at least one hydrogen atom of the aforementioned alkyl group within the alkoxy group has been substituted with a hydroxyl group. The number of hydroxyl groups included in the hydroxyalkyl group is preferably within a range from 1 to 3, and is most preferably 1.

As the aliphatic hydrocarbon group, a linear or branched saturated hydrocarbon group, a linear or branched unsaturated hydrocarbon group, a cyclic aliphatic hydrocarbon group (aliphatic cyclic group), or a combination thereof is preferable.

The linear saturated hydrocarbon group (alkyl group) preferably has 1 to 20 carbon atoms, more preferably 1 to 17 carbon atoms, still more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

These saturated hydrocarbon groups may have part of the carbon atoms substituted with a hetero atom-containing substituent. As the hetero atom-containing substituent, the same hetero atom-containing substituents as those described above which may substitute a part of the carbon atoms constituting the aliphatic hydrocarbon group can be used.

Further, these saturated hydrocarbon groups may have part or all of the hydrogen atoms substituted with a hetero atom-containing substituent. As the hetero atom-containing substituent, the same hetero atom-containing substituents as those described above which may substitute a part or all of the hydrogen atoms constituting the aliphatic hydrocarbon group can be used.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear unsaturated hydrocarbon groups include a vinyl group, a propenyl group (an allyl group) and a butynyl group. Examples of branched unsaturated hydrocarbon groups include a 1-methylpropenyl group and a 2-methylpropenyl group. Of these, a propenyl group is preferable.

These unsaturated hydrocarbon groups may have part of the carbon atoms substituted with a hetero atom-containing substituent. As the hetero atom-containing substituent, the same hetero atom-containing substituents as those described above which may substitute a part of the carbon atoms constituting the aliphatic hydrocarbon group can be used.

Further, these unsaturated hydrocarbon groups may have part or all of the hydrogen atoms substituted with a hetero atom-containing substituent. As the hetero atom-containing substituent, the same hetero atom-containing substituents as those described above which may substitute a part or all of the hydrogen atoms constituting the aliphatic hydrocarbon group can be used.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Further, the aliphatic cyclic group may be either saturated or unsaturated, preferably saturated.

Examples of the monocyclic groups among the aliphatic cyclic groups include groups in which one or more of the hydrogen atoms have been removed from a monocycloalkane; and examples of the polycyclic groups include groups in which one or more of the hydrogen atoms have been removed from a polycycloalkane such as a bicycloalkane, a tricycloalkane, or a tetracycloalkane.

The monocycloalkane preferably has 3 to 8 carbon atoms, and examples thereof include cyclopentane and cyclohexane.

The polycycloalkane preferably has 7 to 12 carbon atoms, and examples thereof include adamantane, norbornane, isobornane, tricyclodecane and tetracyclododecane.

Of these aliphatic cyclic groups, polycyclic groups are preferable, groups in which one or more hydrogen atoms have been removed from a polycycloalkane are more preferable, and a group in which one or more hydrogen atoms have been removed from norbornane (bicyclo[2.2.1]heptane) or a group in which one or more hydrogen atoms have been removed from adamantane is particularly desirable.

In the aliphatic cyclic groups, a part of the carbon atoms constituting the ring structure may be substituted with a substituent containing a hetero atom. In this case, as the substituent containing a hetero atom, the same hetero atom-containing substituents as those described above which may substitute a part of the carbon atoms constituting the aliphatic hydrocarbon group can be used. Among these, —O—, —C(=O)—O—, —S—, —S(=O)$_2$— or —S(=O)$_2$—O— is preferable.

Specific examples of such aliphatic cyclic groups include groups represented by formulas (L1) to (L5) and (S1) to (S4) shown below.

[Chemical Formula 8]

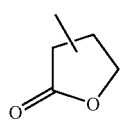

(L1)

-continued

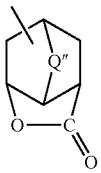 (L2)

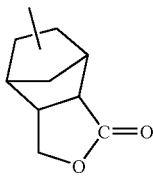 (L3)

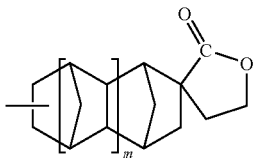 (L4)

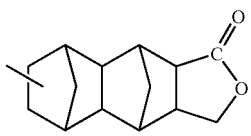 (L5)

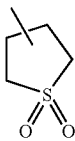 (S1)

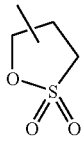 (S2)

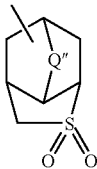 (S3)

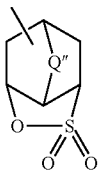 (S4)

[In the formulas above, Q" represents an alkylene group which may include an oxygen atom or a sulfur atom; and m represents an integer of 0 or 1.]

In the formulas, the alkylene group for Q" is preferably linear or branched, and preferably has 1 to 5 carbon atoms. Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$; an ethylene group [—$CH_2CH_2$—]; alkylethylene groups such as —CH($CH_3$)$CH_2$—, —CH($CH_3$)CH($CH_3$)—, —C($CH_3$)$_2CH_2$—, and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—]. Among these, a methylene group or an alkylmethylene group is preferable, and a methylene group, —CH($CH_3$)— or —C($CH_3$)$_2$— is particularly desirable.

The alkylene group may include an oxygen atom (—O—) or a sulfur atom (—S—). Examples of alkylene groups that include an oxygen atom or a sulfur atom include the aforementioned alkylene groups in which —O— or —S— is bonded to the terminal of the alkylene group or interposed within the alkyl group. Specific examples of such alkylene groups include —O—$R^{94}$—, —S—$R^{95}$—, —$R^{96}$—O—$R^{97}$— and —$R^{98}$—S—$R^{99}$—. Each of $R^{94}$ to $R^{99}$ independently represents an alkylene group. As the alkylene group, the same alkylene groups as those described above for Q" can be used. Of these, —O—$CH_2$—, —$CH_2$—O—$CH_2$—, —S—$CH_2$—, —$CH_2$—S—$CH_2$— or the like is preferable.

In these aliphatic cyclic groups, a part or all of the hydrogen atoms may be substituted with a substituent. Examples of the substituent include an alkyl group, a halogen atom, an alkoxy group, a hydroxyl group, —C(=O)—$R^{90}$ [wherein $R^{90}$ represents an alkyl group], —COO$R^{91}$ [wherein $R^{91}$ represents a hydrogen atom or an alkyl group], a halogenated alkyl group, a halogenated alkoxy group, an amino group, an amide group, a nitro group, an oxygen atom (=O), a sulfur atom and a sulfonyl group ($SO_2$).

Examples of the alkyl group for the substituent include the same alkyl groups as those described above for the alkyl group within the alkoxy group as the hetero atom-containing substituent.

As the alkyl group for the substituent, an alkyl group of 1 to 6 carbon atoms is particularly desirable. Further, the alkyl group is preferably a linear or branched alkyl group, and specific examples thereof include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or an ethyl group is preferable, and a methyl group is particularly desirable.

As the halogen atom, alkoxy group, —C(=O)—$R^{90}$, —COO$R^{91}$, halogenated alkyl group and halogenated alkoxy group for the substituent, the same hetero atom-containing substituents as those described above which may substitute a part or all of the hydrogen atoms constituting the aliphatic hydrocarbon group can be used.

As a substituent for substituting the hydrogen atoms of the aliphatic cyclic group, among the various examples described above, an alkyl group, an oxygen atom (=O), or a hydroxyl group is preferable.

The aliphatic cyclic group may have one substituent, or two or more substituents. If the aliphatic cyclic group has two or more substituents, then the two or more of the substituents may be the same or different from each other.

With respect to the aliphatic hydrocarbon group, examples of the combinations of the linear or branched saturated hydrocarbon group, the linear or branched unsaturated hydrocarbon group, and the aliphatic cyclic group include —$R^L$—$R^M$ [wherein $R^L$ represents a linear or branched alkylene group; and $R^M$ represents an aliphatic cyclic group].

In the formula, as $R^L$, a group in which one hydrogen atom has been removed from the saturated hydrocarbon group described above as the linear or branched saturated hydrocarbon group for the aliphatic hydrocarbon group can be used. As $R^L$, a linear alkylene group is preferable, and a methylene group is particularly desirable.

As $R^M$, the same aliphatic cyclic group for the aliphatic hydrocarbon group as those described above can be used. As $R^M$, an aliphatic polycyclic group which may have a substituent is preferable.

As the aliphatic hydrocarbon group for $R^X$, a group selected from the group consisting of groups represented by general formulas (AL-1) to (AL-4) shown below and groups represented by general formulas (L-1) to (L-5) and (S1) to (S4) above is preferable, and a group represented by general formula (AL-3) or (AL-4) is particularly desirable.

[Chemical Formula 9]

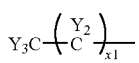
(AL-1)

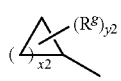
(AL-2)

(AL-3)

(AL-4)

[In the formula, x1 represents an integer of 0 to 16; Y represents a hydrogen atom or a fluorine atom; x2 represents an integer of 1 to 6; $R^g$ represents a substituent; y2 represents an integer of 0 to 10; x3 represents 0 or 1; $R^h$ represents an alkyl group, and two $R^h$ groups may be the same or different from each other; $R^i$ represents a substituent; x4 represents 0 or 1; and y4 represents an integer of 0 to 3.]

In general formula (AL-1), x1 is preferably an integer of 0 to 15, more preferably an integer of 1 to 10.

The plurality of Y in the formula may be the same or different from each other. In general formula (AL-2), x2 is preferably an integer of 1 to 10, more preferably an integer of 3 to 6.

y2 is preferably an integer of 0 to 5, more preferably an integer of 0 to 3.

As $R^g$, the same substituents as those described above which may substitute a part or all of the hydrogen atoms constituting the aliphatic cyclic group can be used. As $R^g$, a hydroxyl group, an oxygen atom (=O), a sulfur atom or a sulfonyl group ($SO_2$) is preferable.

In general formula (AL-3), x3 is most preferably 1.

As $R^h$, the same alkyl groups as those described above as the substituents which may substitute a part or all of the hydrogen atoms constituting the aliphatic cyclic group can be used. As $R^h$, a methyl group is particularly desirable.

In general formula (AL-4), x4 is most preferably 0.

y4 is preferably an integer of 0 to 2, and is most preferably 1.

As $R^i$, the same substituents as those described above which may substitute a part or all of the hydrogen atoms constituting the aliphatic cyclic group can be used. As $R^g$, a hydroxyl group, an oxygen atom (=O), an alkyl group or a fluorinated alkyl group is preferable, and a hydroxyl group is particularly desirable.

As the group represented by general formula (AL-4), a 1-adamantyl group which may have $R^i$ is preferable, more preferably groups having a hydroxyl group for $R^i$, and 3-hydroxy-1-adamantyl group or 3-hydroxy-1-adamantylmethyl group is particularly desirable.

An "aromatic hydrocarbon group" is a hydrocarbon group having an aromatic ring.

The aromatic hydrocarbon group for $R^X$ preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

The number of aromatic rings included in one aromatic hydrocarbon group may be 1 or may be 2 or more, and preferably 1 or 2. If the aromatic hydrocarbon group has 2 or more aromatic rings, then the two or more of the aromatic rings may be the same or different from each other.

The aromatic ring may be an aromatic ring in which the ring skeleton thereof is constituted of only carbon atoms (aromatic hydrocarbon ring), or an aromatic ring in which the ring skeleton thereof contains a hetero atom (aromatic heterocycle).

Specific examples of the aromatic hydrocarbon rings include benzene, naphthalene, anthracene and phenanthrene.

Examples of the hetero atom included in the aromatic heterocycle include an oxygen atom, a sulfur atom, and a nitrogen atom. The hetero atom included in one aromatic heterocycle may be of a single variety, or may include two or more different varieties. Further, the number of hetero atoms included in one aromatic heterocycle may be 1, or may be 2 or more.

Examples of the aromatic heterocycle include those having a benzene skeleton and those having a conjugated double bond (e.g., =C—C=, =C—N= or the like) apart from the above-mentioned hetero atoms within the ring skeleton. More specifically, examples of monocyclic aromatic heterocycles include furan, thiophene, oxazol, isooxazol, thiazol, isothiazol, imidazole, pyrazol, pyridine, and pyrimidine. Further, examples of polycyclic aromatic heterocycles include a condensed ring formed of a benzene ring and a monocyclic aromatic heterocycle as described above.

Specific examples of aromatic hydrocarbon groups having the aforementioned aromatic hydrocarbon ring include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an arylalkyl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 to 2 carbon atoms, and most preferably 1 carbon atom.

Further, specific examples of aromatic hydrocarbon groups having the aforementioned aromatic heterocycle include a group in which the aromatic hydrocarbon ring in the aryl group or arylalkyl group mentioned above has been substituted with the aforementioned aromatic heterocycle (hereafter, referred to as a heteroaryl group and a heteroarylalkyl group, respectively).

The aromatic hydrocarbon group may have a substituent. For example, a part or all of the hydrogen atoms bonded to the aromatic ring included in the aromatic hydrocarbon group may be substituted with a substituent. Examples of the substituent include an alkyl group, a halogen atom, an alkoxy group, a hydroxyl group, —C(=O)—$R^{90}$ [wherein $R^{90}$ represents an alkyl group], —COO$R^{91}$ [wherein $R^{91}$ represents a hydrogen atom or an alkyl group], a halogenated alkyl group, a halogenated alkoxy group, an amino group, an amide group, a nitro group, oxygen atom (=O), a sulfur atom and a sulfonyl group ($SO_2$). As the substituent, the substituent as those described above as the substituent which may substitute a part or all of the hydrogen atoms constituting the aliphatic cyclic group can be used.

As the aromatic hydrocarbon group for $R^X$, groups represented by general formulas (AR-1) to (AL-16) shown below are preferable.

[Chemical Formula 10]

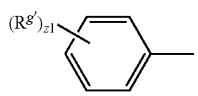 (AR-1)

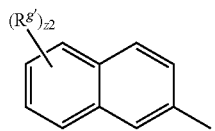 (AR-2)

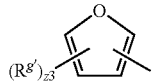 (AR-3)

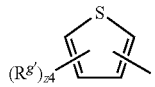 (AR-4)

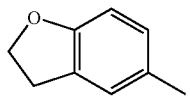 (AR-5)

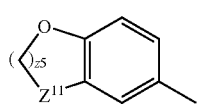 (AR-6)

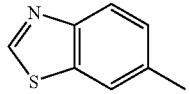 (AR-7)

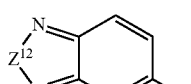 (AR-8)

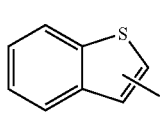 (AR-9)

-continued

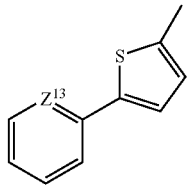 (AR-10)

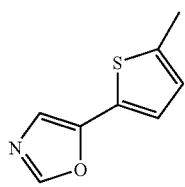 (AR-11)

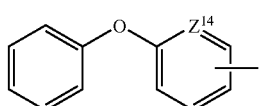 (AR-12)

(AR-13)

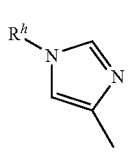

(AR-14)

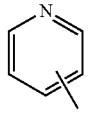

(AR-15)

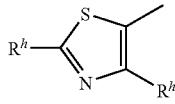

(AR-16)

[In the formulas, $R^g$, represents a substituent; z1 represents an integer of 0 to 5; z2 represents an integer of 0 to 7; z3 represents an integer of 0 to 3; z4 represents an integer of 0 to 3; z5 represents an integer of 1 to 3; $Z^{11}$ represents an oxygen atom or a nitrogen atom; $Z^{12}$ represents an oxygen atom or a sulfur atom; $Z^{13}$ represents a carbon atom or a nitrogen atom; $Z^{14}$ represents a carbon atom or a nitrogen atom; and $R^h$ represents an alkyl group, and the plurality of $R^h$ in formula (AR-15) and (AR-16) may be the same or different from each other.]

As $R^{g'}$, the same substituents as those described above which may substitute a part or all of the hydrogen atoms bonded to the aromatic ring included in the aromatic hydrocarbon group can be used. As $R^{g'}$, a hydroxyl group, an oxygen atom (=O), a sulfur atom or a sulfonyl group ($SO_2$) is preferable.

As $R^h$, the same alkyl groups as those described above as the substituents which may substitute a part or all of the hydrogen atoms constituting the aliphatic cyclic group can be used. As $R^h$, a methyl group is particularly desirable.

In the present invention, it is preferable that $R^X$ be a group represented by any one of the aforementioned general formulas (AL-1) to (AL-4), (L1) to (L5), (S1) to (S4), and (AR-1) to (AR-16).

Further, in terms of the effects to improve the lithography properties, $R^X$ is preferably a group containing a ring within the structure thereof. The ring may be either an aliphatic ring or an aromatic ring, and an aliphatic ring is preferable. Further, the ring may be either a monocyclic group or a polycyclic group, and a polycyclic group is preferable.

In general formula (1), $R^1$ represents a divalent linking group.

The divalent linking group for $R^1$ is not particularly limited, and examples thereof include a divalent hydrocarbon group which may have a hetero atom. As examples of the divalent hydrocarbon group, a group in which one hydrogen atom has been removed from the "hydrocarbon group which may have a hetero atom" mentioned above for $R^X$ can be used.

As $R^1$, an alkylene group which may have a substituent is particularly desirable.

The alkylene group may be linear, branched or cyclic, or a combination thereof. Examples of such combinations include a group in which one or two of linear or branched alkylene groups are bonded to a cyclic alkylene group.

The linear or branched alkylene group preferably has 1 to 12 carbon atoms, more preferably 1 to 5 carbon atoms, and still more preferably 1 to 3 carbon atoms.

Specific examples of the linear or branched alkylene group include a methylene group [—$CH_2$—]; alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; alkylethylene groups such as —$CH(CH_3)CH_2$—, —$CH(CH_3)CH(CH_3)$—, —$C(CH_3)_2CH_2$—, and —$CH(CH_2CH_3)CH_2$—; a trimethylene group (n-propylene group) [—$CH_2CH_2CH_2$—]; alkyltrimethylene groups such as —$CH(CH_3)CH_2CH_2$— and —$CH_2CH(CH_3)CH_2$—; a tetramethylene group [—$CH_2CH_2CH_2CH_2$—]; alkyltetramethylene groups such as —$CH(CH_3)CH_2CH_2CH_2$— and —$CH_2CH(CH_3)CH_2CH_2$—; and a pentamethylene group [—$CH_2CH_2CH_2CH_2CH_2$—].

The linear or branched alkylene group may or may not have a substituent. As the substituent, the same groups as those described above as the "hetero atom-containing substituent" for $R^X$ can be used. Examples of such substituents include a fluorine atom, a fluorinated alkyl group of 1 to 6 carbon atoms which is substituted by a fluorine atom, and an oxygen atom (=O).

As examples of the cyclic alkylene group, a group in which two hydrogen atoms have been removed from the cycloalkanes such as a monocycloalkane or a polycycloalkane mentioned above in relation to the aliphatic cyclic group for $R^X$ can be used.

The cyclic alkylene group may or may not have a substituent. As the substituent, the same substituents as those described above which may substitute a part or all of the hydrogen atoms constituting the aforementioned aliphatic cyclic group for $R^X$ can be used. Examples of such substituents include an alkyl group of 1 to 6 carbon atoms, a fluorine atom, a fluorinated alkyl group of 1 to 6 carbon atoms, and an oxygen atom (=O).

The alkylene group for $R^1$ is preferably a linear alkylene group or a branched alkylene group, more preferably a linear alkylene group. Of these, a methylene group, an ethylene group or a trimethylene group is preferable, and an ethylene group is most preferable.

In formula (1), as the alkylene group for $Y^1$, the same alkylene groups as those described above for $R^1$ having 1 to 4 carbon atoms can be used.

As the fluorinated alkylene group for $Y^1$, groups in which part of or all of the hydrogen atoms in the alkylene group are substituted with fluorine atoms can be used.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As $Y^1$, a fluorinated alkylene group is preferable, and a fluorinated alkylene group in which the carbon atom bonded to the adjacent sulfur atom is fluorinated is particularly desirable. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2$—, —$CF_2CF_2$—, —$CF_2CF_2CF_2$—, and $CH_2CF_2CF_2$— are preferable, —$CF_2$—, —$CF_2CF_2$— and —$CF_2CF_2CF_2$— are more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with atoms or groups other than hydrogen atoms and fluorine atoms.

Examples of the substituents which the alkylene group or fluorinated alkylene group may have include an alkyl group of 1 to 4 carbon atoms, an alkoxy group of 1 to 4 carbon atoms, and a hydroxyl group.

As the anion (I), an anion represented by general formula (I-1) shown below is particularly desirable.

[Chemical Formula 11]

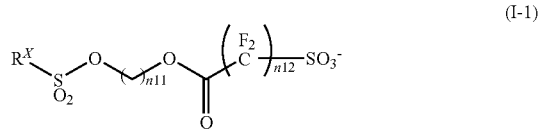

(I-1)

[In the formula, $R^X$ is the same as defined above; n11 represents an integer of 1 to 3 (most preferably 2); and n12 represents an integer of 1 to 4 (most preferably 1).]

The compound according to the third aspect of the present invention is constituted of the above-mentioned anion (I) and a counter cation thereof.

The counter cation in the compound (the cation that forms a salt with the above-mentioned anion (I)) is not particularly limited. The counter cation may be an inorganic cation or an organic cation, and may be appropriately selected from the known cations.

For example, as an inorganic cation, an alkali metal ion can be used. Examples of alkali metal ions include a sodium ion, a potassium ion and a lithium ion.

Further, as an organic cation, Z in formula (b1-1) described later, an amine ion, a quaternary ammonium ion or the like can be used.

Among these compounds, a compound having Z as a counter cation, in other words, a compound represented by general formula (b1-1) shown below (hereafter, frequently referred to as compound (b1-1)) is useful as an acid generator for a chemically amplified resist composition.

Further, a compound having an alkali metal ion, an amine ion or a quaternary ammonium ion as a counter cation, in other words, a compound represented by general formula (b0-1) shown below (hereafter, frequently referred to as compound (b0-1)) is useful for producing the aforementioned compound (b1-1). For example, as shown in the section <Method of producing compound (b1-1)> described later, when the compound (b0-1) is used as a precursor during the production of the compound (b1-1), the yield of the compound (b1-1) is enhanced.

Each of the compounds (b1-1) and (b0-1) and preferable production methods thereof will be described below.

[Chemical Formula 12]

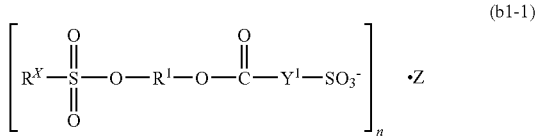

[In the formula, $R^X$, $R^1$ and $Y^1$ are the same as defined above; n represents an integer of 1 to 3; and Z represents an organic cation (exclusive of an amine ion and a quaternary ammonium ion) having a valence of n.]

[Chemical Formula 13]

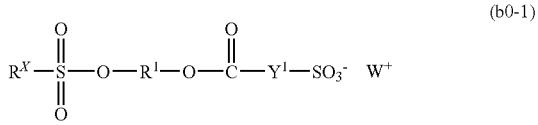

[In the formula, $R^X$, $R^1$ and $Y^1$ are the same as defined above; and $W^+$ represents an alkali metal ion, an amine ion or a quaternary ammonium ion.]

<Compound (b1-1)>

In general formula (b1-1), n represents an integer of 1 to 3, preferably 1 or 2.

Z represents an organic cation (exclusive of an amine ion and a quaternary ammonium ion) having a valence of n. The amine ion and quaternary ammonium ion herein are the same amine ion and quaternary ammonium ion as those mentioned in relation to $W^+$ in the compound (b0-1) described later.

As the organic cation for Z, there is no particular limitation as long as it is a cation other than an amine ion and a quaternary ammonium ion, and any of those cations conventionally known as cation moiety for an onium salt-based acid generator can be appropriately selected for use. As the cation moiety, for example, a sulfonium ion or an iodonium ion can be used, and a sulfonium ion is particularly desirable.

Specific examples of the sulfonium ion include cation represented by general formula (b'-1) shown below. Further, specific examples of the iodonium ion include cation represented by general formula (b'-2) shown below.

[Chemical Formula 14]

[In formula (b'-1), each of $R^{1''}$ to $R^{3''}$ independently represents an aryl group which may have a substituent or an alkyl group, and any two of $R^{1''}$ to $R^{3''}$ may be bonded to each other to form a ring with the sulfur atom in the formula. In formula (b'-2), $R^{5''}$ and $R^{6''}$ each independently represents an aryl group which may have a substituent or an alkyl group.]

In formula (b'-1), each of $R^{1''}$ to $R^{3''}$ independently represents an aryl group which may have a substituent or an alkyl group.

The aryl group for $R^{1''}$ to $R^{3''}$ is not particularly limited and includes, for example, an aryl group having 6 to 20 carbon atoms. The aryl group is preferably an aryl group having 6 to 10 carbon atoms because it can be synthesized at a low cost. Specific examples thereof include a phenyl group and a naphthyl group.

The aryl group may have a substituent. The aryl group "has a substituent" means that part or all of the hydrogen atoms of the aryl group is substituted with a substituent. Examples of the substituent include an alkyl group, an alkoxy group, a hydroxyl group, a hydroxyalkyl group, a hydroxyalkoxy group, a halogen atom, a halogenated alkyl group, a halogenated alkoxy group, an alkoxyalkyloxy group, —O-$L^1$-CO—(O)$_g$—$R^{51}$ [wherein $L^1$ represents a single bond or a divalent linking group; g represents 0 or 1; and $R^{51}$ represents a monovalent hydrocarbon group which may have a hetero atom], —O-$L^2$-CO—(O)$_h$—$R^{52}$—(O)$_i$—CO—(O)$_j$—$R^{53}$ [wherein $L^2$ represents a single bond or a divalent linking group; each of h, i and j independently represents 0 or 1; $R^{52}$ represents a divalent hydrocarbon group which may have a hetero atom; and $R^{53}$ represents a monovalent hydrocarbon group which may have a hetero atom], —O-$L^4$-COOH [wherein $L^4$ represents a divalent linking group], —SO$_2$—$R^f$ [wherein $R^f$ represents a halogenated alkyl group], and a cyano group.

Of these, examples of the alkyl group for the substituent include the same alkyl groups as those described above for $R^{90}$ within —C(=O)—$R^{90}$ as the hetero atom-containing substituent in relation to $R^X$.

As the alkyl group within the alkoxy group for the substituent, the same alkyl groups as those described above can be used.

As examples of the hydroxyalkyl group and hydroxyalkoxy group for the substituent, groups in which part of the hydrogen atoms of the aforementioned alkyl groups and alkoxy groups have been substituted with hydroxyl groups can be given. The number of hydroxyl groups in the hydroxyalkyl group and hydroxyalkoxy group is preferably within a range from 1 to 3, and is most preferably 1.

Examples of the halogen atom as the substituent include a fluorine atom, a chlorine atom, a bromine atom and an iodine atom, and a fluorine atom is preferable.

As examples of the halogenated alkyl group and halogenated alkoxy group for the substituent, a group in which part or all of the hydrogen atoms within the aforementioned alkyl group and alkoxy group have been substituted with halogen atoms can be given. It is particularly desirable that the halogenated alkyl group and a halogenated alkyl group within the halogenated alkoxy group be —$R^{10''}$-$R^{11''}$ [wherein $R^{10''}$ represents a linear or branched alkylene group, and $R^{11''}$ represents a linear or branched perfluoroalkyl group]. In the formula, the alkylene group for $R^{10''}$ may be linear or branched, and is preferably linear. Further, the number of carbon atoms within the alkylene group is preferably within a range of from 1 to 10, more preferably from 3 to 5. The perfluoroalkyl group for $R^{11''}$ may be linear or branched, and is preferably linear. Further, the number of carbon atoms within the perfluoroalkyl group is preferably within a range of from 1 to 10, more preferably from 1 to 4. As —$R^{10''}$-$R^{11''}$, —$(CH_2)_e$—$(CF_2)_e$—$CF_3$ is particularly desirable. In the formula, e represents an integer of 1 to 10, and is preferably an integer of 3 to 5. f represents an integer of 0 to 9, and is preferably an integer of 0 to 3. Further, e f is preferably an integer of 2 to 20, and more preferably an integer of 4 to 7.

Examples of the alkoxyalkyloxy group as the substituent include a group represented by a general formula: —O—C($R^{47}$)($R^{48}$)—O—$R^{49}$ [wherein each of $R^{47}$ and $R^{48}$ independently represents a hydrogen atom or a linear or branched alkyl group; $R^{49}$ represents an alkyl group; and $R^{48}$ and $R^{49}$ may be bonded to each other to form a ring structure, with the provision that at least one of $R^{47}$ and $R^{48}$ represents a hydrogen atom].

The alkyl group for $R^{47}$ and $R^{48}$ preferably has 1 to 5 carbon atoms, and is preferably an ethyl group or a methyl group, and most preferably a methyl group.

It is preferable that either one of $R^{47}$ and $R^{48}$ be a hydrogen atom, and the other be a hydrogen atom or a methyl group, and it is particularly desirable that both of $R^{47}$ and $R^{48}$ be a hydrogen atom.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, a n-butyl group and a tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkane include adamantane, norbornane, isobornane, tricyclodecane and tetracyclododecane. Among these, a group in which one or more hydrogen atoms have been removed from adamantane is preferable.

$R^{48}$ and $R^{49}$ may be bonded to each other to form a ring structure. In such a case, a cyclic group is formed by $R^{48}$, $R^{49}$, the oxygen atom having $R^{49}$ bonded thereto and the carbon atom having the oxygen atom and $R^{48}$ bonded thereto. Such a cyclic group is preferably a 4- to 7-membered ring, and more preferably a 4- to 6-membered ring.

In —O-$L^1$-CO—(O)$_g$—$R^{51}$ for the substituent, $L^1$ may be a single bond or may be a divalent linking group. As examples of the divalent linking group for L', the same groups as those described above for $R^1$ can be given. As the linking group, an alkylene group is preferable, a linear or branched alkylene group is more preferable, and a linear alkylene group is particularly desirable. The alkylene group preferably has 1 to 5 carbon atoms, and specific examples thereof include a methylene group, an ethylene group, a trimethylene group, a tetramethylene group, a 1,1-dimethylethylene group and a pentamethylene group. Among these, a methylene group is particularly desirable.

g may be either 0 or 1.

As —O-$L^1$-CO—(O)$_g$—$R^{51}$, a group (—O—CO—$R^{51}$) in which $L^1$ represents a single bond and g is 0, or a group (—O-$L^1$-CO—O—$R^{51}$) in which $L^1$ represents a divalent linking group and g is 1 is particularly desirable.

As examples of the monovalent hydrocarbon group which may have a hetero atom for $R^{51}$, the same groups as those described above for $R^X$ can be given.

Further, the hydrocarbon group for $R^{51}$ may be an acid dissociable group. The term "acid dissociable group" refers to a group which may dissociate due to the action of acid (the acid generated from the component (B) upon exposure), and examples thereof include the same acid dissociable, dissolution inhibiting groups (e.g., tertiary alkyl ester-type acid dissociable, dissolution inhibiting groups and acetal-type acid dissociable, dissolution inhibiting groups) as those described later in relation to the component (A). Of these, tertiary alkyl ester-type acid dissociable groups are preferable.

In —O-$L^2$-CO—(O)$_h$—$R^{52}$—(O)$_i$—CO—(O)$_j$—$R^{53}$ for the substituent, $L^2$ may be a single bond or may be a divalent linking group. As examples of the divalent linking group for $L^2$, the same groups as those described above for $L^1$ can be given.

Each of h, i and j may be either 0 or 1.

Of the various possibilities, it is preferable that i+j=1. In other words, it is preferable that either one of i and j be 1, and the other be 0.

As —O-$L^2$-CO—(O)$_h$—$R^{52}$—(O)$_i$—CO—(O)$_j$—$R^{53}$, a group (—O—CO—$R^{52}$—O—CO—$R^{53}$) in which $L^2$ represents a single bond, h is 0, i is 1 and j is 0, or a group (—O-$L^2$-CO—O—$R^{52}$—CO—O—$R^{53}$) in which $L^2$ represents a divalent linking group, h is 1, i is 0 and j is 1 is particularly desirable.

As examples of the monovalent hydrocarbon group which may have a hetero atom for $R^{53}$, the same groups as those described above for $R^{51}$ can be given.

In —O-$L^4$-COOH for the substituent, as examples of the divalent linking group for $L^4$, the same groups as those described above for $L^1$ can be given.

As the halogenated alkyl group for $R^f$ in —$SO_2$—$R^f$ for the substituent, the same halogenated alkyl groups for the substituent as those described above can be used. As $R^f$, a fluorinated alkyl group is preferable, and a perfluoroalkyl group is particularly desirable.

Further, the halogenated alkyl group for $R^f$ is preferably linear or branched, and preferably has 1 to 10 carbon atoms. $R^f$ is most preferably a trifluoromethyl group.

The alkyl group for $R^{1''}$ to $R^{3''}$ is not particularly limited and may be a linear, branched or cyclic group, or may be a combination thereof. More specifically, the same alkyl groups as those described above as the alkyl group within the alkoxy group as the hetero atom-containing substituent can be used. Examples thereof include a methyl group, an ethyl group, a n-propyl group, an isopropyl group, a n-butyl group, an isobutyl group, a tert-butyl group, a n-pentyl group, a cyclopentyl group, a hexyl group, a cyclohexyl group, a nonyl group and a decyl group.

The alkyl group for $R^{1''}$ to $R^{3''}$ is preferably a linear or branched alkyl group, and more preferably a linear alkyl group. In terms of achieving excellent resolution, the alkyl group preferably has 1 to 10 carbon atoms, more preferably 1 to 5 carbon atoms. A methyl group, an ethyl group, a n-propyl group or a n-butyl group is particularly desirable because it is excellent in resolution and can be synthesized at a low cost.

The alkyl group may have a substituent. The alkyl group "has a substituent" means that part or all of the hydrogen atoms of the alkyl group is substituted with a substituent.

As the substituent, the same groups as those which the aforementioned aryl group may have as a substituent can be used. Further, as the substituent, the alkyl group may also have an oxygen atom (═O), an aryl group, or the like other than those described above. As examples of the aryl group, the same aryl groups as those described above for $R^{1\prime\prime}$ to $R^{3\prime\prime}$ can be used.

In formula (b'-1), any two of $R^{1\prime\prime}$ to $R^{3\prime\prime}$ may be bonded to each other to form a ring with the sulfur atom in the formula. The ring may be either a monocyclic group or a polycyclic group. For example, when either one or both of the two groups forming a ring is a cyclic group (a cyclic alkyl group or aryl group), when they bond with each other, a polycyclic ring (condensed ring) is formed.

When two of $R^{1\prime\prime}$ to $R^{3\prime\prime}$ are bonded to each other to form a ring, it is preferable that a ring containing the sulfur atom in the formula within the ring skeleton thereof be a 3 to 10-membered ring including the sulfur atom, and it is particularly desirable that the ring be a 5 to 7-membered ring including the sulfur atom.

Specific examples of the ring formed by the bonding of two of $R^{1\prime\prime}$ to $R^{3\prime\prime}$ include benzothiophene, dibenzothiophene, 9H-thioxanthene, thioxanthone, thianthrene, phenoxathiin, tetrahydrothiophenium and tetrahydrothiopyranium.

When two of $R^{1\prime\prime}$ to $R^{3\prime\prime}$ are bonded to each other to form a ring with the sulfur atom in the formula, the remaining one of $R^{1\prime\prime}$ to $R^{3\prime\prime}$ is preferably an aryl group. As examples of the aryl group, the same aryl groups as those described above for $R^{1\prime\prime}$ to $R^{3\prime\prime}$ can be used.

When using the compound for the light source of 193 nm or 248 nm in the Deep UV region, among $R^{1\prime\prime}$ to $R^{3\prime\prime}$ in formula (b'-1), at least one of $R^{1\prime\prime}$ to $R^{3\prime\prime}$ preferably represents an aryl group, more preferably at least two of $R^{1\prime\prime}$ to $R^{3\prime\prime}$ represent an aryl group, and it is particularly desirable that all of $R^{1\prime\prime}$ to $R^{3\prime\prime}$ represent an aryl group. As a result, the compound exhibits absorption in the Deep UV region.

However, the present invention is not limited to those described above, and a cation in which all of $R^{1\prime\prime}$ to $R^{3\prime\prime}$ represent an alkyl group is also preferable. Such compounds can be used, for example, as an acid generator for EB or EUV.

Among various cation moieties for the compound represented by general formula (b'-1), when all of $R^{1\prime\prime}$ to $R^{3\prime\prime}$ represent a phenyl group which may have a substituent, in other words, when the cation moiety has a triphenylsulfonium skeleton, preferable examples of the cation moiety include those cations represented by formulas (b'-1-1) to (b'-1-25) shown below.

[Chemical Formula 15]

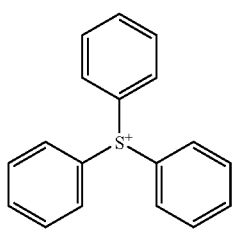
(b'-1-1)

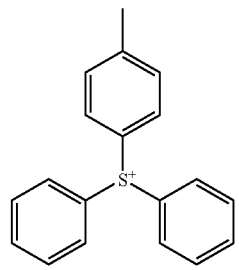
(b'-1-2)

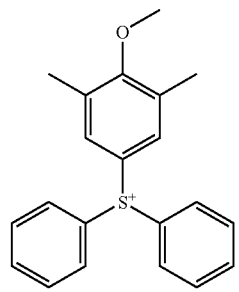
(b'-1-3)

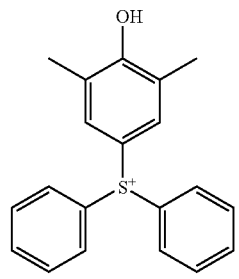
(b'-1-4)

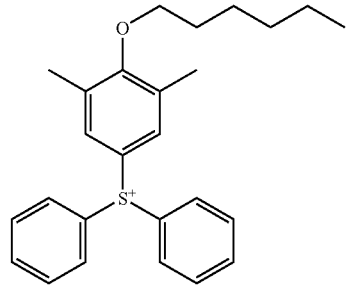
(b'-1-5)

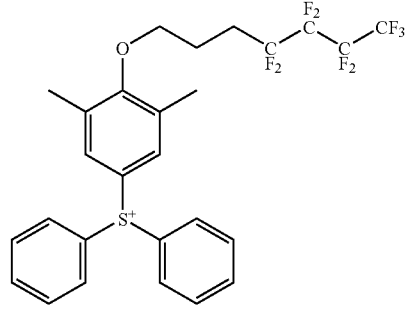
(b'-1-6)

(b'-1-7)
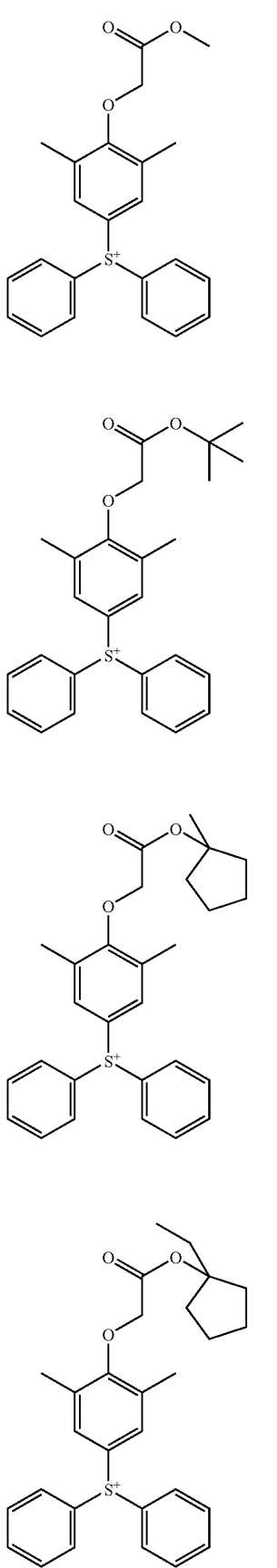
(b'-1-8)
(b'-1-9)
(b'-1-10)
[Chemical Formula 16]
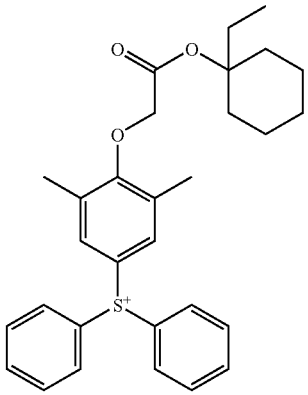
(b'-1-11)
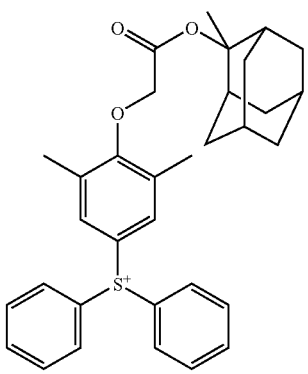
(b'-1-12)
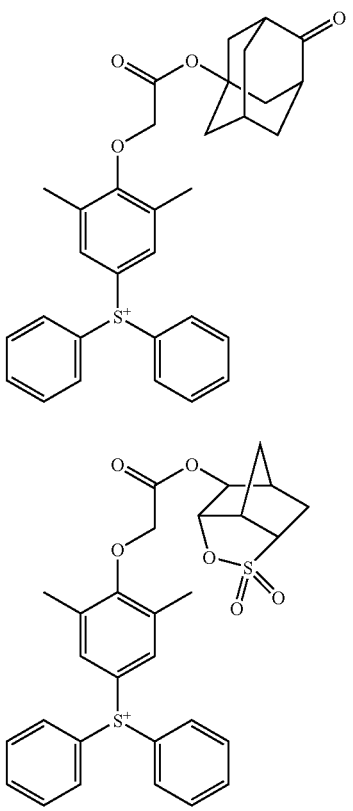
(b'-1-13)
(b'-1-14)

-continued
(b'-1-15)
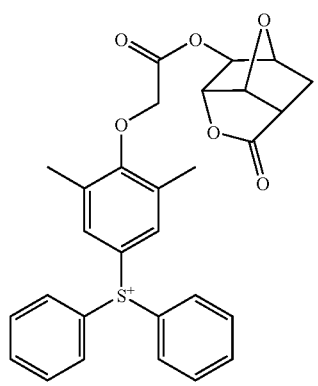
(b'-1-19)
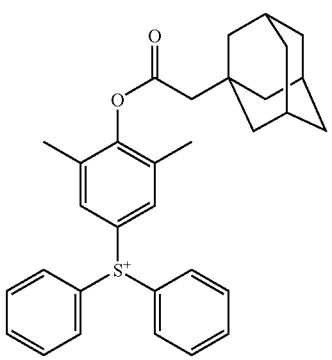
[Chemical Formula 17]
(b'-1-16)
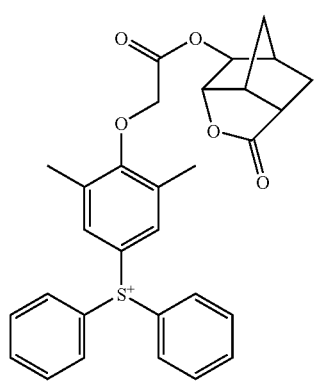
(b'-1-20)
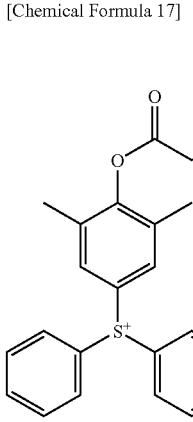
(b'-1-17)
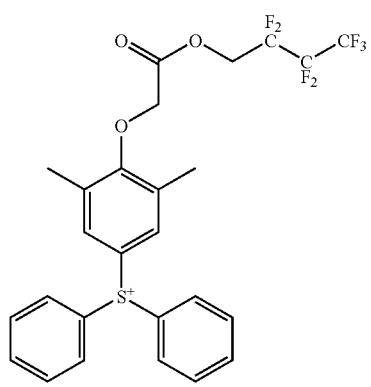
(b'-1-21)
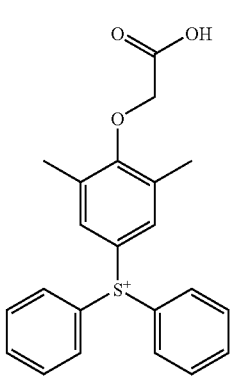
(b'-1-18)
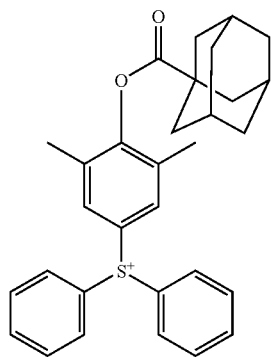
(b'-1-22)
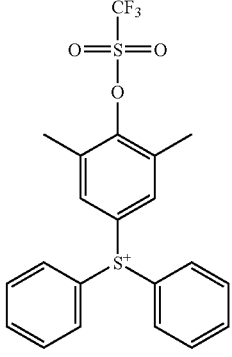

-continued

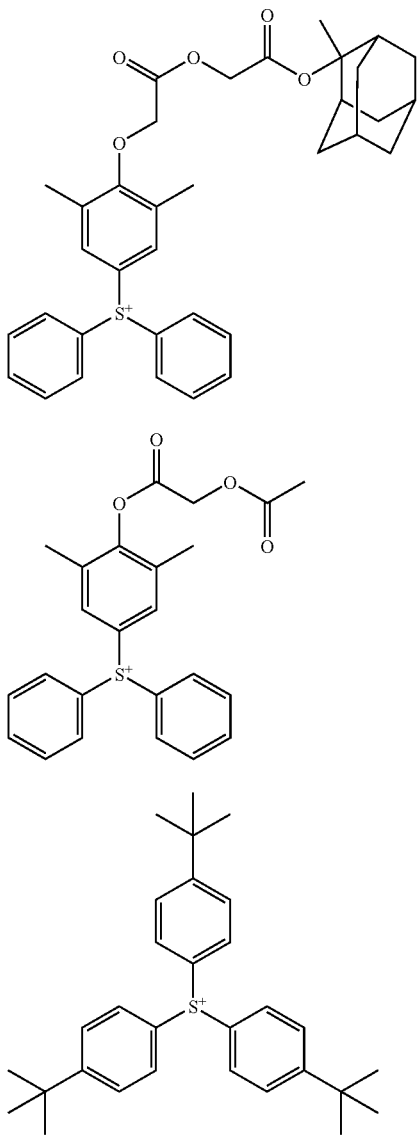

(b'-1-23)

(b'-1-24)

(b'-1-25)

Further, these cation moieties having part or all of the phenyl groups substituted with a naphthyl group which may have a substituent are also favorably used. In such a case, among three phenyl groups, it is preferable that one or two phenyl groups be substituted with a naphthyl group.

Further, these cation moieties having part or all of the phenyl groups substituted with an alkyl group which may have a substituent are also favorably used. As examples of the alkyl group, the same alkyl groups as those described above for $R^{1\prime\prime}$ to $R^{3\prime\prime}$ can be used, and a methyl group or a trifluoromethyl group is particularly desirable. In such a case, among three phenyl groups, it is preferable that one or two phenyl groups be substituted with the alkyl group.

Furthermore, among various cation moieties for the compound represented by general formula (b'-1), when any two of $R^{1\prime\prime}$ to $R^{3\prime\prime}$ are bonded to each other to form a ring with the sulfur atom in the formula, preferable examples of the cation moiety include those cation moieties represented by formula (b'-1-26) or (b'-1-27) shown below.

[Chemical Formula 18]

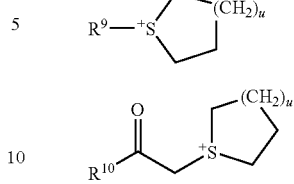

(b'-1-26)

(b'-1-27)

[In the formulas, $R^9$ represents a phenyl group which may have a substituent, a naphthyl group which may have a substituent, or an alkyl group of 1 to 5 carbon atoms; $R^{10}$ represents a phenyl group which may have a substituent, a naphthyl group which may have a substituent, an alkyl group of 1 to 5 carbon atoms, an alkoxy group of 1 to 5 carbon atoms, or a hydroxyl group; and u represents an integer of 1 to 3.]

In formulas (b'-1-26) and (b'-1-27), as the substituent which the phenyl group or naphthyl group for $R^9$ and $R^{10}$ may have, the same groups as those which the aforementioned aryl group for $R^{1\prime\prime}$ to $R^{3\prime\prime}$ may have as a substituent can be used.

u represents an integer of 1 to 3, and is most preferably 1 or 2.

As Z, a cation represented by general formula (b-5) or (b-6) shown below is also preferable.

[Chemical Formula 19]

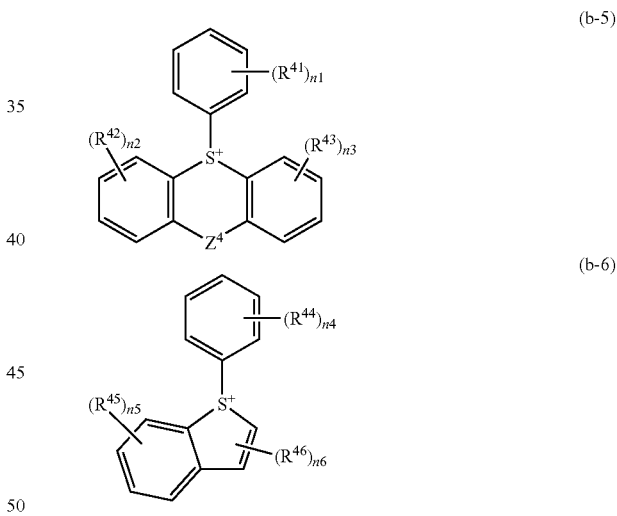

(b-5)

(b-6)

[In the formulas, $Z^4$ represents a single bond or a divalent linking group; $R^{41}$ to $R^{46}$ each independently represents a substituent; $n_1$ to $n_5$ each independently represents an integer of 0 to 3; and $n_6$ represents an integer of 0 to 2.]

In general formula (b-5), the divalent linking group for $Z^4$ preferably has no more than 15 carbon atoms, more preferably no more than 10 carbon atoms.

Specific examples of the linking group include an alkylene group, an arylene group, a carbonyl group, a sulfonyl group, a carbonyloxy group, a carbonylamino group, a sulfonylamide group, an ether group, a thioether group, an amino group, a disulfide group, an acyl group, an alkylsulfonyl group, —CH═CH—, —C≡C—, an aminocarbonylamino group and an aminosulfonylamino group.

The linking group may have a substituent. The linking group "has a substituent" means that part or all of the hydrogen atoms in the linking groups having hydrogen atoms has been substituted with atoms or groups other than hydrogen atoms.

Examples of the substituents include an alkoxy group, a halogen atom, a halogenated alkyl group, a hydroxyl group and an oxygen atom (═O).

As the aforementioned alkoxy group, an alkoxy group having 1 to 5 carbon atoms can be used, and a methoxy group, an ethoxy group, a n-propoxy group, a iso-propoxy group, a n-butoxy group or a tert-butoxy group is preferable.

Examples of the aforementioned halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, a n-butyl group or a tert-butyl group) have been substituted with the aforementioned halogen atoms. As the halogenated alkyl group, a fluorinated alkyl group is preferable.

As $Z^4$, a single bond, an alkylene group, a carbonyl group, a sulfonyl group, an ester group, an ether group or a thioether group is preferable, more preferably a single bond, an alkylene group, a carbonyl group or a sulfonyl group, and most preferably a single bond or a carbonyl group.

In formulas (b-5) and (b-6), as the substituent for $R^{41}$ to $R^{46}$, the same groups as those which the aforementioned aryl group for $R^{1\prime\prime\prime}$ to $R^{3\prime\prime\prime}$ may have as a substituent can be used.

When the subscripts $n_1$ to $n_6$ of $R^{41}$ to $R^{46}$ represent an integer of 2 or more, the plurality of $R^{41}$ to $R^{46}$ may be the same or different from each other.

$n_1$ is preferably 0 to 2, more preferably 0 or 1, and still more preferably 0.

It is preferable that $n_2$ and $n_3$ each independently represents 0 or 1.

When $Z^4$ represents a single bond, $n_2$ and $n_3$ most preferably represent 0.

When $Z^4$ represents a divalent linking group, it is preferable that either one or both of $n_2$ and $n_3$ represents 1. Further, in such a case, as $R^{42}$ and $R^{43}$, a halogenated alkyl group is preferable, more preferably a fluorinated alkyl group, still more preferably a perfluoroalkyl group, and most preferably a trifluoromethyl group.

$n_4$ is preferably 0 to 2, and more preferably 0 or 1.
$n_5$ is preferably 0 or 1, and more preferably 0.
$n_6$ is preferably 0 or 1, and more preferably 1.

As Z, a cation represented by general formula (b-7) shown below is also preferable.

[Chemical Formula 20]

(b-7)

[In the formula, p represents 2 or 3; $Y^6$ represents a linking group having a valence of p; $R^{61}$ represents an arylene group or an alkylene group which may have a substituent; each of $R^{62}$ and $R^{63}$ independently represents an aryl group or an alkyl group which may have a substituent, and $R^{62}$ and $R^{63}$ may be bonded to each other to form a ring with the sulfur atom in the formula.]

In formula (b-7), $Y^6$ represents a linking group having a valence of p, and p represents 2 or 3.

When p is 2, as the divalent linking group for $Y^6$, an alkylene group, an alkenylene group (e.g., —CH═CH—), an alkynylene group (e.g., —C≡C—) an arylene group, a carbonyl group, a carbonyloxy group, a sulfonyl group (—S(═O)$_2$—), a carbonylimino group (—C(═O)—NH—), a sulfonylimino group (—S(═O)$_2$—NH—), an ether group (—O—), a thioether group (—S—), an imino group (—NH—), a disulfide group (—S—S—), a carbonylalkylene group, a sulfonylalkylene group, an iminocarbonylimino group (—NH—C(═O)—NH—), iminosulfonylimino group (—NH—S(═O)$_2$—NH—), or a group in which any two or more of these groups are combined can be used.

Of these, the alkylene group, alkenylene group, carbonylalkylene group or sulfonylalkylene group preferably has 1 to 20 carbon atoms, more preferably 1 to 15 carbon atoms, still more preferably 1 to 10 carbon atoms, still more preferably 1 to 6 carbon atoms, and most preferably 1 to 4 carbon atoms.

The alkylene group, alkenylene group and alkynylene group for $Y^6$ and the alkylene group within the carbonylalkylene group and sulfonylalkylene group may be linear, branched or cyclic.

These groups may have part or all of the hydrogen atoms substituted with a substituent. As the substituent, for example, the same hetero atom-containing substituents as those described above in relation to $R^X$ which may substitute a part or all of the hydrogen atoms constituting the aliphatic hydrocarbon group can be used. As the substituent, a halogen atom is preferable, and a fluorine atom is particularly desirable.

Examples of the arylene group for $Y^6$ include groups in which one hydrogen atom has been removed from the aromatic hydrocarbon group described above in relation to $R^X$.

The arylene group may have part or all of the hydrogen atoms substituted with a substituent. As the substituent, for example, the same substituents as those described above in relation to $R^X$ which may substitute a part or all of the hydrogen atoms bonded to the aromatic ring included in the aromatic hydrocarbon group can be used. As the substituent, a halogen atom is preferable, and a fluorine atom is particularly desirable.

In the carbonylimino group (—C(═O)—NH—), sulfonylimino group (—S(═O)$_2$—NH—), imino group (—NH—), iminocarbonylimino group (—NH—C(═O)—NH—) and iminosulfonylimino group (—NH—S(═O)$_2$—NH—) for $Y^6$, the hydrogen atom within the —NH— moiety may be substituted with a substituent. As an example of such a substituent, an alkyl group and an acyl group can be given.

As the divalent linking group for $Y^6$, a group in which an alkylene group, an alkenylene group, or an arylene group is combined with 2 carbonyl groups is preferable, and a group in which two carbonyl groups are bonded to the aromatic ring is particularly desirable.

When p is 3, as the trivalent linking group for $Y^6$, for example, a group (trivalent group) in which one hydrogen atom has been removed from the alkylene group, alkenylene group, alkynylene group, arylene group, carbonylimino group, sulfonylimino group, imino group, carbonylalkylene group, sulfonylalkylene group, iminocarbonylimino group (—NH—C(═O)—NH—) or iminosulfonylimino group (—NH—S(═O)$_2$—NH—) described above as the divalent linking group, or a group in which any one of these trivalent groups is combined with at least one of the divalent linking groups can be used.

As the trivalent linking group for $Y^6$, a group in which an alkylene group, an alkenylene group or an arylene group having one hydrogen atom removed therefrom is combined with 3 carbonyl groups is preferable, and a group in which 3 carbonyl groups are bonded to the aromatic ring is particularly desirable.

Specific examples of preferable groups for $Y^6$ are shown below.

In formula (y6-1), the bonding positions of two carbonyl groups may be any one of the ortho position, meta position or para position of benzene, and the meta position or para position is preferable.

In formula (y6-2), the bonding positions of two carbonyl groups are not particularly limited. Examples of preferable combinations of the bonding positions include a combination of the 1st and 4th positions of naphthalene, and a combination of the 2nd and 6th positions of naphthalene.

In formula (y6-3), the bonding positions of two carbonyl groups are not particularly limited. Examples of preferable combinations of the bonding positions include a combination of the 3rd and 3'rd positions of biphenyl, and a combination of the 4th and 4'th positions of biphenyl.

[Chemical Formula 21]

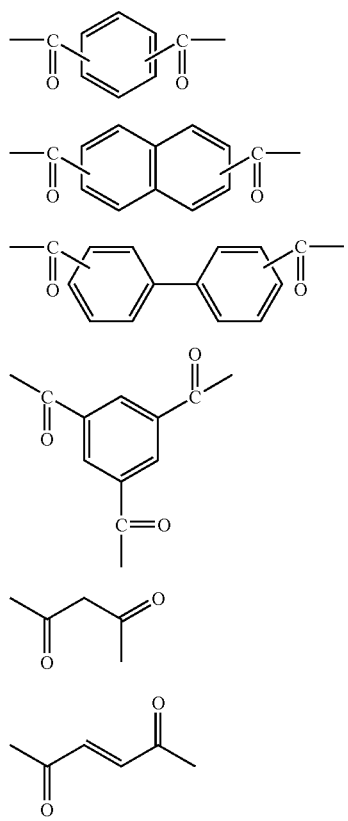

(y6-1)

(y6-2)

(y6-3)

(y6-4)

(y6-5)

(y6-6)

In general formula (b-7), as the arylene group which may have a substituent or the alkylene group for $R^{61}$, the same aryl group or the alkyl group which may have a substituent as those described above for $R^{1\prime\prime}$ to $R^{3\prime\prime}$ in general formula (b'-1) having one hydrogen atom removed therefrom can be used.

As the aryl group which may have a substituent or the alkyl group for $R^{62}$ and $R^{63}$, the same aryl group or the alkyl group which may have a substituent as those described above for $R^{1\prime\prime}$ to $R^{3\prime\prime}$ in general formula (b'-1) can be used.

In formula (b-7), $R^{62}$ and $R^{63}$ may be bonded to each other to form a ring with the sulfur atom in the formula. In such a case, the ring including the sulfur atom is preferably a 3- to 10-membered ring, and a 5- to 7-membered ring is particularly desirable.

The ring structure formed with the sulfur atom may include a hetero atom such as a sulfur atom or an oxygen atom (—O—, =O).

Specific examples of the ring (i.e., the ring structure is formed with the sulfur atom or the ring is not formed with the sulfur atom) formed include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring and a phenazine ring.

Specific examples of preferable groups represented by —O—$R^{61}$—$S^+(R^{62})(R^{63})$ (group indicated inside the bracket [ ]) in general formula (b-7) include those represented by general formulas (b-7-1) to (b-7-3) shown below.

In general formulas (b-7-2) and (b-7-3), as the alkyl group for $R^{101}$ and $R^{102}$, the same alkyl groups as those described above for $R^{1\prime\prime}$ to $R^{3\prime\prime}$ in general formula (b'-1) which the aryl group may have as a substituent can be used, and a methyl group is particularly desirable.

The plurality (i.e., 2 or 3 represented by p) of —O—$R^{61}$—$S^+(R^{62})(R^{63})$ groups in formula (b-7) may be the same or different from each other, and are preferably the same in terms of production thereof

[Chemical Formula 22]

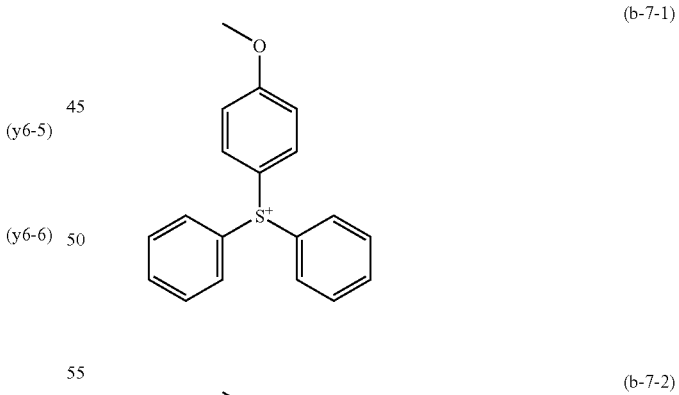

(b-7-1)

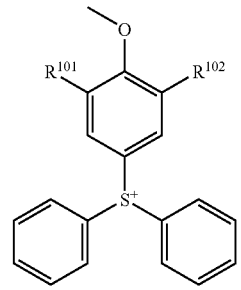

(b-7-2)

-continued

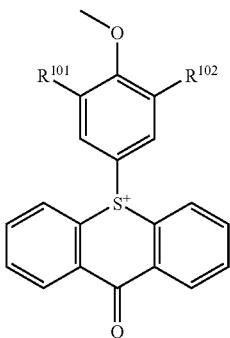

(b-7-3)

[In the formulas, $R^{101}$ and $R^{102}$ each independently represents an alkyl group.]

The above-mentioned compound (b1-1) is a novel compound.

Further, the compound (b1-1) is useful as an acid generator for a chemically amplified resist composition, and can be added to a chemically amplified resist composition as an acid generator.

The method for producing the compound (b1-1) is not particularly limited, and the compound (b1-1) can be produced, for example, by a method described later in the section <Method of producing compound (b1-1)>.

<Compound (b0-1)>

The compound (b0-1) is a compound represented by general formula (b0-1) above.

In general formula (b0-1), examples of alkali metal ions for $W^+$ include a sodium ion, a potassium ion and a lithium ion.

Amine ions are cations formed as a result of the bonding of one hydrogen atom to the nitrogen atom of amines (a primary amine, secondary amine or tertiary amine).

Specific examples of amine ions or quaternary ammonium ions include cations represented by general formula (w-1) shown below (hereafter, frequently referred to as cation (w-1)).

[Chemical Formula 23]

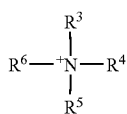

(w-1)

[In the formula, each of $R^3$ to $R^6$ independently represents a hydrogen atom or a hydrocarbon group which may have a substituent, with the provision that at least one of $R^3$ to $R^6$ represents the hydrocarbon group, and at least two of $R^3$ to $R^6$ may be bonded to each other to form a ring.]

In formula (w-1), each of $R^3$ to $R^6$ independently represents a hydrogen atom or a hydrocarbon group which may have a substituent, and at least one of $R^3$ to $R^6$ represents the hydrocarbon group.

As examples of the hydrocarbon group for $R^3$ to $R^6$, the same hydrocarbon groups as those described above for $R^x$ can be given. The hydrocarbon group may be either an aliphatic hydrocarbon group or an aromatic hydrocarbon group.

When the hydrocarbon group is an aliphatic hydrocarbon group, as the aliphatic hydrocarbon group, an alkyl group of 1 to 12 carbon atoms which may have a substituent is particularly desirable.

As the substituent which the hydrocarbon group may have, the same hetero atom-containing substituents as those described above in relation to $R^x$ which may substitute a part of the carbon atoms constituting the aliphatic hydrocarbon group, and the same hetero atom-containing substituents as those described above which may substitute a part or all of the hydrogen atoms constituting the aliphatic hydrocarbon group can be used.

When each of $R^3$ to $R^6$ is independent (i.e., when at least two of $R^3$ to $R^6$ are not bonded to each other to form a ring), as the cation (w-1), those in which at least one of $R^3$ to $R^6$ represents an alkyl group or a hydroxyalkyl group and at least one of $R^3$ to $R^6$ represents a hydrogen atom are preferable. Further, in such a case, it is preferable that two or three of $R^3$ to $R^6$ represent the aforementioned hydrocarbon group, and it is more preferable that three of $R^3$ to $R^6$ represent the aforementioned hydrocarbon group.

More specifically, those in which one of $R^3$ to $R^6$ represents an alkyl group and the remaining three groups represent a hydrogen atom (i.e., monoalkylammonium ions); those in which two of $R^3$ to $R^6$ represents an alkyl group and the remaining two groups represent a hydrogen atom (i.e., dialkylammonium ions); those in which three of $R^3$ to $R^6$ represent an alkyl group and the remaining one group represents a hydrogen atom (i.e., trialkylammonium ions); or those in which one to three of $R^3$ to $R^6$ represent a hydroxyalkyl group, one of $R^3$ to $R^6$ represents a hydrogen atom and the remaining 0 to 2 groups represent an alkyl group (i.e., alcohol amines) are preferable. Among these, dialkylammonium ions or trialkylammonium ions are preferable, and trialkylammonium ions are particularly desirable.

Each of the alkyl groups is preferably independent and has 1 to 12 carbon atoms, more preferably 1 to 10 carbon atoms, and most preferably 1 to 8 carbon atoms. Specific examples of the alkyl groups include a methyl group, an ethyl group, a propyl group, a butyl group, a pentyl group, a hexyl group, a heptyl group, an octyl group, a nonyl group and a decyl group. Among these, an ethyl group is particularly desirable.

The alkyl group or the hydroxyalkyl group may have a substituent other than a hydroxyl group. As the substituent, an ether group (—O—) is particularly desirable.

Specific examples of such cations include those in which one hydrogen atom is bonded to the nitrogen atom of the following amines:

i.e., monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Further, when each of $R^3$ to $R^6$ is independent (i.e., when at least two of $R^3$ to $R^6$ are not bonded to each other to form a ring), as the cation (w-1), cations in which all of $R^3$ to $R^6$ represent an alkyl group (tetraalkylammonium ions) are also preferable.

Examples of tetraalkylammonium ions include a tetramethylammonium ion, a tetraethylammonium ion and a tetrabutylammonium ion.

Further, as the cation (w-1), those in which at least one of $R^3$ to $R^6$ represents an aromatic hydrocarbon group (aromatic amines) may also be used. As the aromatic hydrocarbon group for the aromatic amines, a phenyl group is preferable.

Specific examples thereof include those in which one hydrogen atom is bonded to the nitrogen atom of aromatic amines such as aniline and 4-dimethylaminopyridine (DMAP).

In formula (w-1), at least two of $R^3$ to $R^6$ may be bonded to each other to form a ring. For example, two of $R^3$ to $R^6$ may be bonded to each other to form a ring (a ring having a C—N—C structure); when two of $R^3$ and $R^6$ represents same a hydrogen atom or a hydrocarbon group which may have a substituent group, three of $R^3$ to $R^6$ may be bonded to each other to form a ring (a ring having a C=N—C structure); or two pairs, each consisted of two of $R^3$ to $R^6$ bonded to each other, may form two rings.

The ring formed by the bonding of at least two of $R^3$ to $R^6$ together with the sulfur atom in the formula (i.e., a heterocycle containing a nitrogen atom as a hetero atom, and hereafter frequently referred to as "nitrogen-containing heterocycle") may have an atom other than carbon atoms and nitrogen atoms (e.g., an oxygen atom, a sulfur atom or the like) in the ring skeleton thereof.

The nitrogen-containing heterocycle may be an aromatic ring or an aliphatic ring. Further, when the nitrogen-containing heterocycle is an aliphatic ring, the aliphatic ring may be either saturated or unsaturated. Furthermore, the nitrogen-containing heterocycle may be either monocyclic or polycyclic.

The nitrogen-containing heterocycle preferably has 3 to 30 carbon atoms, more preferably 5 to 30 carbon atoms, and still more preferably 5 to 20 carbon atoms.

Specific examples of monocyclic nitrogen-containing heterocycle include pyrrole, pyridine, imidazole, pyrrazole, 1,2,3-triazole, 1,2,4-triazole, pyrimidine, pyrazine, 1,3,5-triazine, tetrazole, piperidine, piperazine, pyrrolidine and morpholine.

Specific examples of polycyclic nitrogen-containing heterocycle include quinoline, isoquinoline, indole, pyrrolo[2,3-b]pyridine, indazole, benzimidazole, benztriazole, carbazole, acridine, 1,5-diazabicyclo[4.3.0]-5-nonene, 1,8-diazabicyclo[5.4.0]-7-undecene, hexamethylenetetramine, 1,4-diazabicyclo[2.2.2]octane and 6-azabicyclo[3.2.1]octane.

Of these, pyridine and isoquinoline are preferable.

These nitrogen-containing heterocycles may have a substituent. As the substituent, the same groups as those which the aforementioned hydrocarbon group for $R^3$ to $R^6$ may have as a substituent can be used. The substituent may be bonded to the carbon atom of the nitrogen-containing heterocycles, or may be bonded to the nitrogen atom of the nitrogen-containing heterocycles.

In the present invention, as $W^+$ in general formula (b0-1), an amine ion or a quaternary ammonium ion is preferable because the compound (b0-1) is highly useful as a precursor, especially during the production of compounds useful as an acid generator through a salt substitution as described later. When $W^+$ represents an amine ion or a quaternary ammonium ion, the compound can be easily purified by washing with water, and thus improvement in the purity of final products can be expected. For example, when $W^+$ represents an alkali metal ion, purification by washing with water is difficult to conduct because the compounds are dissolved.

The above-mentioned compound (b0-1) is a novel compound.

Further, the compound (b0-1) is useful as a precursor in the production of a compound (for example, the aforementioned compound (b1-1)) useful as an acid generator for a chemically amplified resist composition. In other words, as described later in the section <Method of producing compound (b1-1)>, the compound obtained by subjecting the compound (b0-1) to a salt substitution to substitute the cation moiety $W^+$ of the compound (b0-1) with an adequate organic cation (such as a sulfonium ion or an iodonium ion) is a compound that generates acid (sulfonic acid) upon exposure. Such a compound is useful as an acid generator for a resist composition.

The compound (b0-1) of the present invention can be produced, for example, by a method of producing the compound (b0-1) described later.

<Method of Producing Compound (b1-1)>

The compound (b1-1) can be produced, for example, by a production method including a step of reacting a compound represented by general formula (b0-1) shown below with a compound represented by general formula (b0-2) shown below.

[Chemical Formula 24]

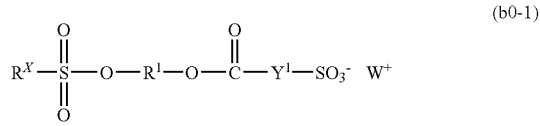

[In the formulas, $R^X$, $R^1$, $Y^1$, n and Z are the same as defined above; $W^+$ represents an alkali metal ion, an amine ion or a quaternary ammonium ion; and $A^-$ represents a counter anion.]

In the formulas, $R^X$, $R^1$, $Y^1$, n and Z are the same as defined above. Further, $W^+$ is the same as described above for $W^+$ in the compound (b0-1).

The counter anion for $A^-$ is not particularly limited. Preferable examples of counter anions include a halogen ion such as a bromine ion and a chlorine ion, a p-toluenesulfonate ion, an alkylsulfonate ion, an alkylsulfate ion and a benzenesulfonate ion.

The compound (b0-1) can be produced, for example, by a method of producing the compound (b0-1) described later.

As the compound (b0-2), commercially available compounds may be used, or the compounds may be produced by a conventional method.

The reaction between the compound (b0-1) and the compound (b0-2) can be conducted by a conventional salt substitution method. For example, the reaction may be conducted by dissolving the compound (b0-1) and the compound (b0-2) in a solvent such as water, dichloromethane, acetonitrile, methanol or chloroform, followed by stirring or the like.

The reaction temperature is preferably about 0 to 150° C., and more preferably about 0 to 100° C. The reaction time varies, depending on the reactivity of the compounds (b0-1) and (b0-2), the reaction temperature or the like. However, in general, the reaction time is preferably 0.5 to 10 hours, and more preferably 1 to 5 hours.

After the reaction, the compound (b1-1) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the obtained compound (b1-1) can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis, Among the compounds (b0-1) used in the above-mentioned production method, those in which $W^+$ represents an amine ion or a quaternary ammonium ion are highly useful as a precursor during the production of the compound (b1-1). This is because when the cation moiety of the compound (b0-1) is an amine ion or a quaternary ammonium ion, the compound can be easily purified by washing with water, and thus improvement in the purity of final products can be expected. For example, when the cation moiety is an alkali metal ion, purification by washing with water is difficult to conduct because the compounds are dissolved.

Therefore, in the method of producing the compound (b1-1), as the compound (b0-1), it is preferable to use those having an amine ion or a quaternary ammonium ion as the cation moiety thereof.

<Method of Producing Compound (b0-1)>

The compound (b0-1) can be produced, for example, by a production method including a step of reacting a compound represented by general formula (1-11) shown below (hereafter, referred to as a compound (1-11)) with a compound represented by general formula (1-12) shown below (hereafter, referred to as a compound (1-12)) under the presence of an alkali metal hydroxide, an amine or a quaternary ammonium salt.

[Chemical Formula 25]

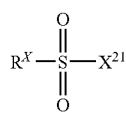
(1-11)

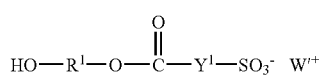
(1-12)

[In the formulas, $R^X$, $R^1$ and $Y^1$ are the same as defined above; $W'^+$ represents an alkali metal ion, an amine ion or a quaternary ammonium ion; and $X^{21}$ represents a halogen atom.]

In the formulas, the alkali metal ion, amine ion and quaternary ammonium ion for $W'^+$ are the same alkali metal ion, amine ion and quaternary ammonium ion as those mentioned in relation to $W^+$ in general formula (b0-1) above.

As $W'^+$, an alkali metal ion is preferable.

As the halogen atom for $X^{21}$, a bromine atom, a chlorine atom, an iodine atom and a fluorine atom can be used. In terms of reactivity, a bromine atom or a chlorine atom is preferable, and a chlorine atom is particularly desirable.

The method of reacting the compound (1-11) with the compound (1-12) is not particularly limited, and can be performed, for example, by allowing the compound (1-11) to come into contact with the compound (1-12) in a reaction solvent under the presence of an alkali metal hydroxide, an amine or a quaternary ammonium salt.

Such a method can be performed, for example, by adding the compound (1-11) to a solution obtained by dissolving the compound (1-12) in a reaction solvent, in the presence of an alkali metal hydroxide, an amine or a quaternary ammonium salt.

As the reaction solvent, any solvent which is capable of dissolving the compound (1-11) and the compound (1-12) as the raw materials can be used. Specific examples of such solvents include tetrahydrofuran (THF), acetone, dimethylformamide (DMF), dimethylacetamide, dimethylsulfoxide (DMSO) and acetonitrile.

As the alkali metal hydroxide, hydroxides of the alkali metal ions as those described above for $W^+$ can be used. Specific examples thereof include sodium hydroxide and potassium hydroxide.

As the amine, the same monoalkylamines, dialkylamines, trialkylamines, aromatic amines, and amines containing a nitrogen-containing heterocycle as those described above for $W^+$ can be used.

As the quaternary ammonium salt, tetraalkylammonium hydroxides such as tetramethylammonium hydroxide, tetraethylammonium hydroxide and tetrabutylammonium hydroxide can be used.

In such a case, as the alkali metal hydroxide, amine or quaternary ammonium salt present in a reaction solvent, it is preferable to use those which are compatible with $W^+$ in the compound (b1-0) to be obtained.

The amount added of the compound (1-11) is preferably 1 to 3 equivalents, and more preferably 1 to 2 equivalents, based on the amount of the compound (1-12).

The reaction temperature is preferably −20 to 40° C., and more preferably 0 to 30° C. The reaction time varies depending on the reactivity of the compound (1-11) and the compound (1-12), the reaction temperature, and the like. However, in general, the reaction temperature is preferably 1 to 120 hours, and more preferably 1 to 48 hours.

As the compounds (1-11) and (1-12), commercially available compounds may be used, or the compounds may be synthesized.

For example, when $W'^+$ in the compound (1-12) represents an alkali metal ion, such a compound (compound (1-12')) represented by general formula (1-12') shown below) can be synthesized, for example, by reacting a compound (121) represented by general formula (121) shown below with a compound (122) represented by general formula (122) shown below.

[Chemical Formula 26]

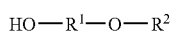
(121)

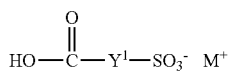
(122)

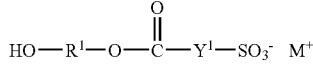
(1-12')

[In the formulas, $R^1$ and $Y^1$ are the same as defined above; $R^2$ represents an aliphatic group which may have an aromatic group as a substituent; and $M^+$ represents an alkali metal ion.]

As $M^+$, the same alkali metal ions as those described above for $W^+$ can be used.

$R^2$ represents an aliphatic group which may have an aromatic group as a substituent.

The aliphatic group may be either a saturated aliphatic group, or an unsaturated aliphatic group. Further, the aliphatic group may be linear, branched or cyclic, or a combination thereof.

The aliphatic group may be either an aliphatic hydrocarbon group consisting of carbon atoms and hydrogen atoms, a group in which part of the carbon atoms constituting the aforementioned aliphatic hydrocarbon group have been substituted with a substituent containing a hetero atom, or a group in which part or all of the hydrogen atoms constituting the aforementioned aliphatic hydrocarbon group have been substituted with a substituent containing a hetero atom.

As these substituents containing a hetero atom, the same groups as those described above as the "hetero atom-containing substituent" for $R^X$ can be used.

As the aliphatic hydrocarbon group, a linear or branched saturated hydrocarbon group of 1 to 30 carbon atoms, a linear or branched monovalent unsaturated hydrocarbon group of 2 to 10 carbon atoms, or a cyclic aliphatic hydrocarbon group (aliphatic cyclic group) of 3 to 30 carbon atoms is preferable.

The linear saturated hydrocarbon group preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 5 carbon atoms, more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

The aliphatic group for $R^2$ may have an aromatic group as a substituent.

Examples of aromatic groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and a heteroaryl group in which a part of the carbon atoms constituting the ring(s) of the aforementioned aryl group has been substituted with a hetero atom such as an oxygen atom, a sulfur atom or a nitrogen atom.

These aromatic groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. Further, the halogenated alkyl group is preferably a fluorinated alkyl group. Examples halogen atoms include a fluorine atom, a chlorine atom, an iodine atom and a bromine atom, and a fluorine atom is preferable.

If the $R^2$ group in the compound (121) represents an aromatic group, i.e., when the oxygen atom adjacent to the $R^2$ group is directly bonded to an aromatic ring without interposing an aliphatic group, the reaction between the compound (121) and the compound (122) does not proceed, such that the compound (1-12') cannot be obtained.

As the compounds (121) and (122), commercially available compounds may be used, or the compounds may be synthesized by a conventional method.

For example, a method of synthesis of compound (122) including a step of heating a compound (0-1) represented by general formula (0-1) shown below in the presence of an alkali, and neutralizing the resultant, thereby obtaining a compound (0-2) represented by general formula (0-2) shown below (hereafter, this step is referred to as a "salt formation step"); and a step of heating the compound (0-2) in the presence of an acid having an acid strength stronger than that of the compound (112), thereby obtaining the compound (112) (hereafter, this step is referred to as a "carboxylic acid generation step" can be used.

[Chemical Formula 27]

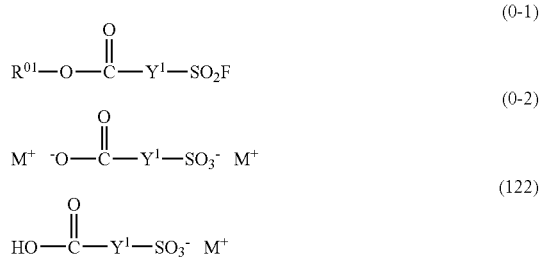

[In the formulas, $R^{01}$ represents an alkyl group; and $Y^1$ and $M^+$ are the same as defined above.]

As the alkyl group for $R^{01}$, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group. Among these, an alkyl group of 1 to 4 carbon atoms is preferable, and a methyl group is particularly desirable.

As the compound (0-1), a commercially available compound can be used.

The salt formation step can be performed, for example, by dissolving the compound (0-1) in a solvent, and adding an alkali to the resulting solution, followed by heating.

As the solvent, any solvent which is capable of dissolving the compound (0-1) can be used. Examples of such a solvent include water and tetrahydrofuran.

As the alkali, an alkali including an alkali metal ion corresponding to $M^+$ in formula (0-2) is used. Examples of such an alkali include alkali metal hydroxides such as sodium hydroxide, potassium hydroxide and lithium hydroxide.

The amount of the alkali used is preferably 1 to 5 moles, more preferably 2 to 4 moles, per 1 mole of the compound (0-1).

The heating temperature is preferably about 20 to 120° C., and more preferably about 50 to 100° C. The heating time varies, depending on the heating temperature and the like, but in general, the heating time is preferably 0.5 to 12 hours, and more preferably 1 to 5 hours.

The neutralization following the heating can be conducted by adding an acid such as hydrochloric acid, sulfuric acid or p-toluenesulfonic acid to the reaction mixture following the heating.

It is preferable to conduct the neutralization so that the pH of the reaction mixture (25° C.) after addition of an acid falls within the range of 6 to 8. Further, the temperature of the reaction mixture during the neutralization is preferably 20 to 30° C., and more preferably 23 to 27° C.

After the reaction, the compound (0-2) within the reaction mixture may be separated and purified. The separation and purification can be conducted by a conventional method. For example, any one of concentration, solvent extraction, crystallization, recrystallization and chromatography can be used alone, or two or more of these methods may be used in combination.

In the carboxylic acid generation step, the compound (0-2) obtained in the salt formation step is heated in the presence of an acid having an acid strength stronger than that of the compound (122), thereby obtaining the compound (122).

"An acid having an acid strength stronger than that of the compound (122)" (hereafter, frequently referred to simply as "strong acid") refers to an acid having a pKa value (25° C.) smaller than that of —COOH within the compound (122). By using such a strong acid, —COO-$M^+$ within the compound (0-2) can be converted into —COOH, thereby obtaining the compound (122).

The strong acid can be appropriately selected from any conventional acids which exhibit a pKa value smaller than that of —COOH within the compound (122). The pKa value of —COOH within the compound (122) can be determined by a conventional titration method.

Specific examples of strong acids include a sulfonic acid, such as an arylsulfonic acid or an alkylsulfonic acid; sulfuric acid; and hydrochloric acid. An example of an arylsulfonic acid includes p-toluenesulfonic acid. Examples of alkylsulfonic acids include methanesulfonic acid and trifluoromethane sulfonic acid. In consideration of solubility in an organic solvent and ease in purification, p-toluenesulfonic acid is particularly desirable as the strong acid.

The carboxylic acid generation step can be performed, for example, by dissolving the compound (0-2) in a solvent, and adding an acid to the resulting solution, followed by heating.

As the solvent, any solvent which is capable of dissolving the compound (0-2) can be used. Examples of such solvents include acetonitrile and methyl ethyl ketone.

The amount of the strong acid used is preferably 0.5 to 3 moles, and more preferably 1 to 2 moles, per 1 mole of the compound (0-2).

The heating temperature is preferably about 20 to 150° C., and more preferably about 50 to 120° C. The heating time varies, depending on the heating temperature and the like, but in general, the heating time is preferably 0.5 to 12 hours, and more preferably 1 to 5 hours.

After the reaction, the compound (122) within the reaction mixture may be separated and purified. The separation and purification can be conducted by a conventional method. For example, any one of concentration, solvent extraction, crystallization, recrystallization and chromatography can be used alone, or two or more of these methods may be used in combination.

When $W'^+$ in the compound (1-12) represents an amine ion or a quaternary ammonium ion, such a compound (hereafter referred to as a compound (1-12")) can be produced, for example, by reacting the compound (1-12') with an amine or ammonium salt.

As the amine or ammonium salt used in such cases, the same alkylamines, dialkylamines, trialkylamines, and hydrochloride salts or hydrobromide salts of aromatic amines as those described above can be used.

For example, the reaction may be conducted by dissolving the compound (1-12") and the ammonium salt in a solvent such as water, dichloromethane, acetonitrile, methanol or chloroform, followed by stirring or the like.

The reaction temperature is preferably about 0 to 150° C., and more preferably about 0 to 100° C. The reaction time varies, depending on the reactivity of the compounds, the reaction temperature, and the like. However, in general, the reaction time is preferably 0.5 to 10 hours, and more preferably 1 to 5 hours.

After the reaction between the compounds (1-11) and (1-12), the compound (b0-1) within the reaction mixture may be separated and purified. The separation and purification can be conducted by a conventional method. For example, any one of concentration, solvent extraction, crystallization, recrystallization and chromatography can be used alone, or two or more of these methods may be used in combination.

The structure of the obtained compound (b0-1) can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Acid Generator>>

The acid generator of the present invention consists of the aforementioned compound (b1-1) according to the present invention.

The acid generator is useful as an acid generator for a chemically amplified resist composition.

<<Resist Composition>>

The resist composition of the present invention includes a base material component (A) which exhibits changed solubility in an alkali developing solution under action of acid (hereafter, referred to as "component (A)") and an acid generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base material component for a chemically amplified resist composition can be used alone, or two or more of such organic compounds can be mixed together.

Here, the term "base material component" refers to an organic compound capable of forming a film.

Generally, as the component (A), an organic compound having a molecular weight of 500 or more is used. When the organic compound has a molecular weight of 500 or more, the film-forming ability is satisfactory, and a resist pattern of nano level can be easily formed.

The "organic compound having a molecular weight of 500 or more" is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

In general, as a polymer, any of those which have a molecular weight of 2,000 or more is used. Hereafter, a "resin" refers to a polymer having a molecular weight of 2,000 or more. With respect to the aforementioned resin, the "molecular weight" is the polystyrene equivalent weight average molecular weight determined by gel permeation chromatography (GPC).

As the component (A), a resin may be used or a low molecular compound may be used, or these types of compounds may be used in combination.

When the resist composition of the present invention is a negative resist composition, for example, as the component (A), a base material component that is soluble in an alkali developing solution is used, and a cross-linking agent is further blended therein.

In the negative resist composition, when acid is generated from the component (B) upon exposure, the action of the generated acid causes cross-linking between the base material component and the cross-linking agent, and the cross-linked portion becomes insoluble in an alkali developing solution. As a result, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and an alkyl ester (preferably an alkyl ester of 1 to 5 carbon atoms) of α-(hydroxyalkyl)acrylic acid as disclosed in Japanese Unexamined Patent Application, First Publication No. 2000-206694; a (meth)acrylic resin having a sulfone amide group or a polycycloolefin resin as disclosed in U.S. Pat. No. 6,949,325; a (meth)acrylic resin having a fluorinated alcohol as disclosed in U.S. Pat. No. 6,949,325, Japanese Unexamined Patent Application, First Publication No. 2005-336452 or 2006-317803; or a polycycloolefin resin having a fluorinated alcohol as disclosed in Japanese Unexamined Patent Application, First Publication No. 2006-259582, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group or a melamine-based cross-linking agent is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base material component that exhibits increased solubility in an alkali developing solution under the action of acid is used. More specifically, the base material component is substantially insoluble in an alkali developing solution prior to exposure, but when acid is generated from the component (B) upon exposure, the action of this acid causes an increase in the solubility of the base material component in an alkali developing solution. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base material component that exhibits increased solubility in an alkali developing solution under the action of acid. That is, the resist composition of the present invention is preferably a positive resist composition.

The component (A) may be a resin component (A1) which exhibits increased solubility in an alkali developing solution under action of acid (hereafter, referred to as "component (A1)"), a low molecular weight compound (A2) which exhibits increased solubility in an alkali developing solution under action of acid (hereafter, referred to as "component (A2)"), or a mixture of the component (A1) and the component (A2). Of the various possibilities, the component (A) preferably includes the component (A1).

[Component (A1)]

As the component (A1), a resin component (base resin) typically used as a base material component for a chemically amplified resist composition can be used alone, or two or more of such resin components can be mixed together.

In the present embodiment, it is preferable that the component (A1) include a structural unit derived from an acrylate ester.

In the present descriptions and claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. Examples of the substituent bonded to the carbon atom on the α-position include an alkyl group of 1 to 5 carbon atoms, a halogenated alkyl group of 1 to 5 carbon atoms and a hydroxyalkyl group. A carbon atom on the α-position of an acrylate ester refers to the carbon atom having the carbonyl group bonded thereto, unless specified otherwise.

With respect to the acrylate ester, the alkyl group for the substituent at the α-position is preferably a linear or branched alkyl group, and specific examples thereof include a methyl group, an ethyl group, a propyl group, an isopropyl group, a n-butyl group, an isobutyl group, a tert-butyl group, a pentyl group, an isopentyl group and a neopentyl group.

Specific examples of the halogenated alkyl group include groups in which some or all of the hydrogen atoms of the aforementioned "alkyl group for the substituent at the α-position" are substituted with halogen atoms. Examples of the halogen atom include a fluorine atom, a chlorine atom, a bromine atom and an iodine atom, and a fluorine atom is particularly desirable.

In the present invention, it is preferable that a hydrogen atom, an alkyl group of 1 to 5 carbon atoms or a halogenated alkyl group of 1 to 5 carbon atoms is bonded to the α-position of the acrylate ester, more preferably a hydrogen atom, an alkyl group of 1 to 5 carbon atoms or a fluorinated alkyl group of 1 to 5 carbon atoms. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1):

The structural unit (a1) is a structural unit derived from an acrylate ester containing an acid dissociable, dissolution inhibiting group.

As the acid dissociable, dissolution inhibiting group for the structural unit (a1), any of those which have been proposed as acid dissociable, dissolution inhibiting groups for a base resin of a chemically amplified resist may be used. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known. Here, the term "(meth)acrylate ester" is a generic term that includes either or both of the acrylate ester having a hydrogen atom bonded to the α-position and the methacrylate ester having a methyl group bonded to the α-position.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, in general, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity. The "aliphatic branched, acid dissociable, dissolution inhibiting group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable, dissolution inhibiting group, for example, a group represented by the formula —$C(R^{71})(R^{72})(R^{73})$ can be given. In the formula, each of $R^{71}$ to $R^{73}$ independently represents a linear alkyl group of 1 to 5 carbon atoms. The group represented by the formula —$C(R^{71})(R^{72})(R^{73})$ preferably has 4 to 8 carbon atoms, and specific examples include a tert-butyl group, a 2-methyl-2-butyl group, a 2-methyl-2-pentyl group and a 3-methyl-3-pentyl group. Among these, a tert-butyl group is particularly desirable.

The term "aliphatic cyclic group" refers to a monocyclic group or polycyclic group that has no aromaticity.

The "aliphatic cyclic group" within the structural unit (a1) may or may not have a substituent. Examples of substituents include an alkyl group of 1 to 5 carbon atoms, an alkoxy group of 1 to 5 carbon atoms, a fluorine atom, a fluorinated alkyl group of 1 to 5 carbon atoms which is substituted by a fluorine atom, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group. The aliphatic cyclic group preferably has 3 to 20 carbon atoms, more preferably 3 to 12 carbon atoms.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Further, these groups in which one or more hydrogen atoms have been removed from a monocycloalkane and groups in which one or more hydrogen atoms have been removed from a polycycloalkane may have part of the carbon atoms constituting the ring replaced with an ethereal oxygen atom (—O—).

Examples of acid dissociable, dissolution inhibiting groups containing an aliphatic cyclic group include (i) a group which has a tertiary carbon atom on the ring structure of a monovalent aliphatic cyclic group; and (ii) a group which has a branched alkylene group containing a tertiary carbon atom and a monovalent aliphatic cyclic group to which the tertiary carbon atom is bonded.

Specific examples of (1) a group which has a tertiary carbon atom on the ring structure of a monovalent aliphatic cyclic group include groups represented by general formulas (1-1) to (1-9) shown below.

Specific examples of (ii) a group which has a branched alkylene group containing a tertiary carbon atom and a monovalent aliphatic cyclic group to which the tertiary carbon atom is bonded include groups represented by general formulas (2-1) to (2-6) shown below.

[Chemical Formula 28]

(1-1) 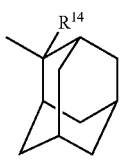

(1-2) 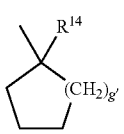

(1-3) 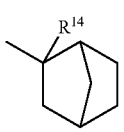

(1-4) 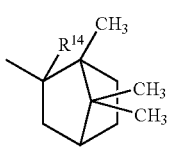

(1-5) 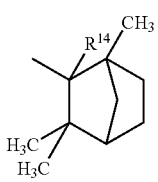

(1-6) 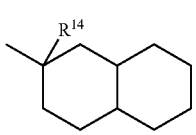

(1-7) 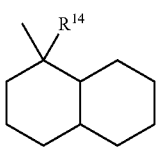

(1-8) 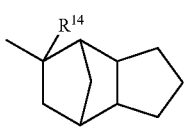

(1-9) 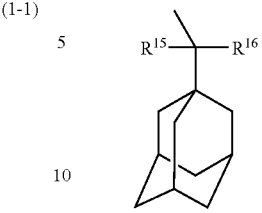

[In the formulas above, $R^{14}$ represents an alkyl group; and g' represents an integer of 0 to 8.]

[Chemical Formula 29]

(2-1) 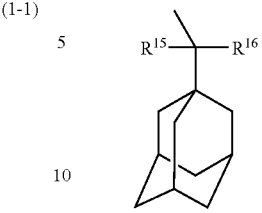

(2-2) 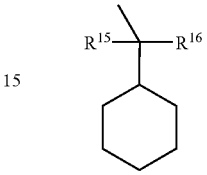

(2-3) 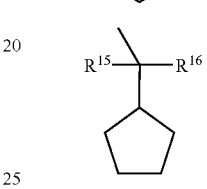

(2-4) 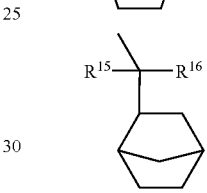

(2-5) 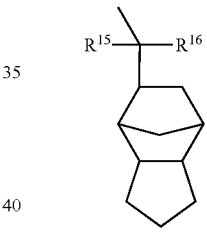

(2-6) 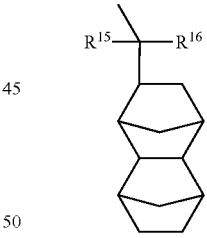

[In the formulas above, each $R^{15}$ and $R^{16}$ independently represents an alkyl group.]

As the alkyl group for $R^{14}$, a linear or branched alkyl group is preferable.

The linear alkyl group preferably has 1 to 5 carbon atoms, more preferably 1 to 4 carbon atoms, and still more preferably 1 or 2 carbon atoms. Specific examples include a methyl group, an ethyl group, a n-propyl group, a n-butyl group and a n-pentyl group. Among these, a methyl group, an ethyl group or a n-butyl group is preferable, and a methyl group or an ethyl group is more preferable.

The branched alkyl group preferably has 3 to 10 carbon atoms, and more preferably 3 to 5 carbon atoms. Specific examples of such branched alkyl groups include an isopropyl group, an isobutyl group, a tert-butyl group, an isopentyl group and a neopentyl group, and an isopropyl group is particularly desirable.

g' is preferably an integer of 0 to 3, more preferably 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6) above, part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of substituents include an alkyl group of 1 to 5 carbon atoms, a fluorine atom and a fluorinated alkyl group.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 30]

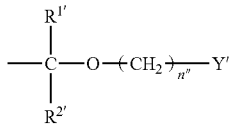

(p1)

[In the formula, $R^{1'}$ and $R^{2'}$ each independently represents a hydrogen atom or an alkyl group of 1 to 5 carbon atoms; n" represents an integer of 0 to 3; and Y' represents an alkyl group of 1 to 5 carbon atoms or an aliphatic cyclic group.]

In general formula (p1) above, n" is preferably an integer of 0 to 2, more preferably 0 or 1, and most preferably 0.

As the lower alkyl group for $R^h$ and $R^{2'}$, the same alkyl groups as those described above for R can be used, although a methyl group or an ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 31]

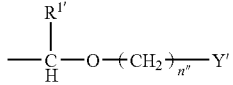

(p1-1)

[In the formula, $R^h$, n" and Y' are the same as defined above.]

As the alkyl group for Y', the same alkyl groups as those described for R above can be used.

As the aliphatic cyclic group for Y', any of the aliphatic monocyclic or polycyclic groups which have been proposed for conventional ArF resists and the like can be appropriately selected for use. For example, the same aliphatic cyclic groups described above in connection with the "aliphatic cyclic group-containing acid dissociable, dissolution inhibiting groups" can be used.

Further, as the acetal-type, acid dissociable, dissolution inhibiting group, groups represented by general formula (p2) shown below can also be used.

[Chemical Formula 32]

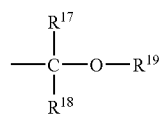

(p2)

[In the formula, $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein $R^{17}$ is bonded to $R^{19}$ to form a ring.]

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or a methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and $R^{19}$ may be bonded to $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

Specific examples of the structural unit (a1) include a structural unit represented by general formula (a1-0-1) shown below and a structural unit represented by general formula (a1-0-2) shown below.

[Chemical Formula 33]

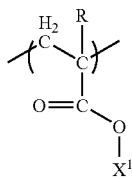
(a1-0-1)

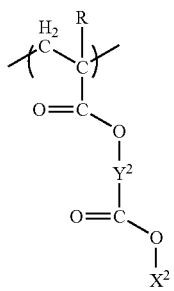
(a1-0-2)

[In the formulas, R each independently represents a hydrogen atom, an alkyl group of 1 to 5 carbon atoms or a halogenated alkyl group of 1 to 5 carbon atoms; $X^1$ represents an acid dissociable, dissolution inhibiting group; $Y^2$ represents a divalent linking group; and $X^2$ represents an acid dissociable, dissolution inhibiting group.]

In general formula (a10-1) shown above, the alkyl group and halogenated alkyl group for R are the same as the alkyl group and halogenated lower alkyl group which can be bonded to the α-position of the aforementioned acrylate ester. As R, a hydrogen atom, an alkyl group of 1 to 5 carbon atoms or a fluorinated alkyl group of 1 to 5 carbon atoms is preferable, and a hydrogen atom or a methyl group is particularly desirable.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

As the divalent linking group for $Y^2$, there are no particular limitations, and an alkylene group, a divalent aliphatic cyclic group or a divalent linking group containing a hetero atom can be used.

When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, as the aliphatic cyclic group, the same as those mentioned above in connection with the explanation of "aliphatic cyclic group" can be used, except that two or more hydrogen atoms have been removed from a monocycloalkane or a polycycloalkane. As the aliphatic cyclic group, a group in which two or more hydrogen atoms have been removed from cyclopentane, cyclohexane, norbornane, isobornane, adamantane, tricyclodecane or tetracyclododecane is particularly desirable.

When $Y^2$ represents a divalent linking group containing a hetero atom, for example, —O—, —C(=O)—O—, —C(=O)—, —O—C(=O)—O—, —C(=O)—NH—, —NH— (wherein H may be substituted with an alkyl group, an acyl group or the like), —S—, —S(=O)$_2$—, —S(=O)$_2$—O—, or -A-O—B—(wherein each of A and B independently represents a divalent hydrocarbon group which may have a substituent, and O is an oxygen atom) can be used.

When $Y^2$ represents a divalent linking group —NH— and the H in the formula is replaced with a substituent (such as an alkyl group or an acyl group), the substituent preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent. A hydrocarbon "has a substituent" means that a part or all of the hydrogen atoms within the hydrocarbon group is substituted with groups or atoms other than a hydrogen atom.

The hydrocarbon group for A may be either an aliphatic hydrocarbon group, or an aromatic hydrocarbon group. An aliphatic hydrocarbon group refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8 carbon atoms, still more preferably 2 to 5 carbon atoms, and most preferably 2 carbon atoms.

As the linear aliphatic hydrocarbon group, a linear alkylene group is preferable, and specific examples include a methylene group, an ethylene group [—(CH$_2$)$_2$-], a trimethylene group [—(CH$_2$)$_3$-], a tetramethylene group [—(CH$_2$)$_4$-] and a pentamethylene group [—(CH$_2$)$_5$-].

As the branched aliphatic hydrocarbon group, a branched alkylene group is preferable, and specific examples include various alkylalkylene groups, e.g., alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

These linear or branched aliphatic hydrocarbon groups may or may not have a substituent. Examples of such substituents include a fluorine atom, a fluorinated alkyl group of 1 to 5 carbon atoms which is substituted by a fluorine atom, and an oxygen atom (=O).

As examples of the aliphatic hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is either bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon group may or may not have a substituent. Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used.

As B, a linear or branched aliphatic hydrocarbon group is preferable, and a methylene group or an alkylmethylene group is particularly desirable. The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 34]

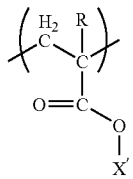
(a1-1)

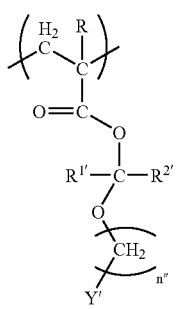
(a1-2)

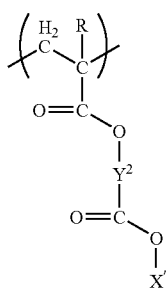
(a1-3)

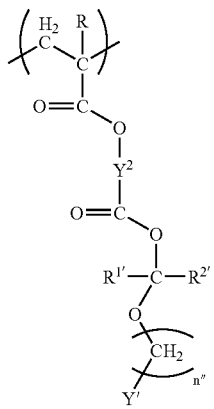
(a1-4)

[In the formulas, R, $R^{1'}$, $R^{2'}$, n'', Y' and $Y^2$ are the same as defined above; and X' each independently represents a tertiary alkyl ester-type acid dissociable, dissolution inhibiting group.]

In the above formulas, examples of the tertiary alkyl ester-type acid dissociable, dissolution inhibiting group for X' include the same tertiary alkyl ester-type acid dissociable, dissolution inhibiting groups as those described above.

As $R^{1'}$, $R^{2'}$, n'' and Y' are respectively the same as defined for $R^h$, $R^{2t}$, n'' and Y' in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ and $R^a$ represents a hydrogen atom, a methyl group or a trifluoromethyl group.

[Chemical Formula 35]

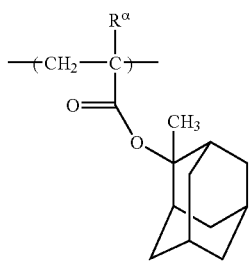
(a1-1-1)

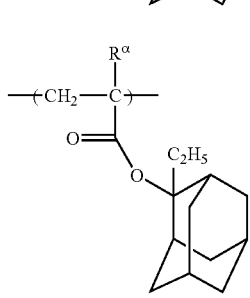
(a1-1-2)

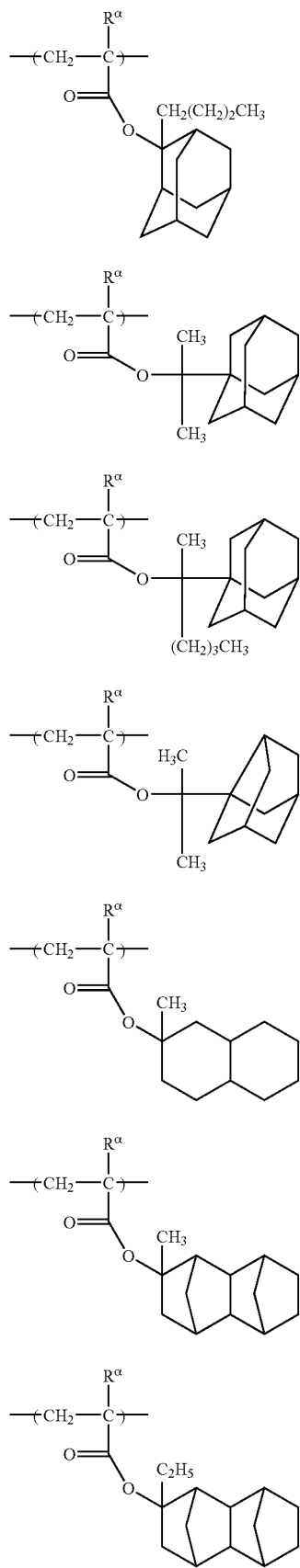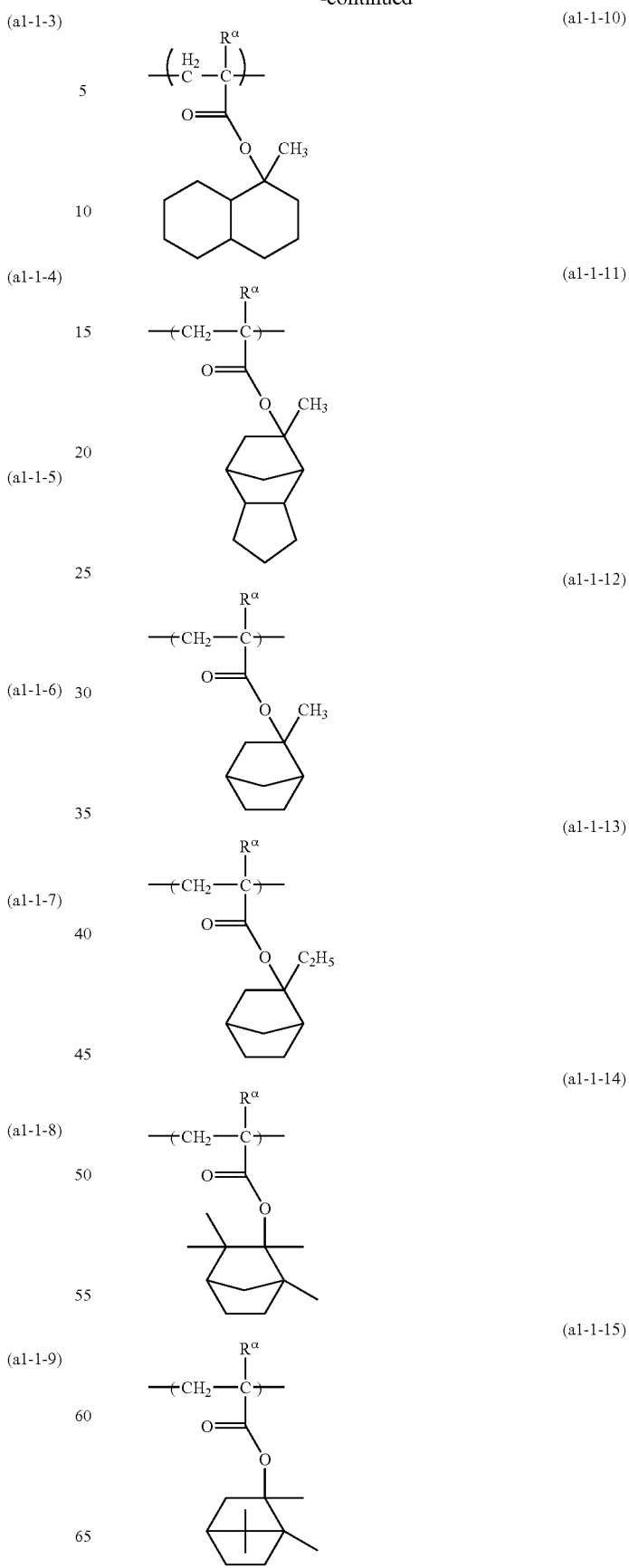

(a1-1-16) 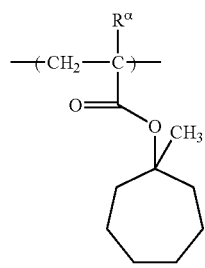
(a1-1-17) 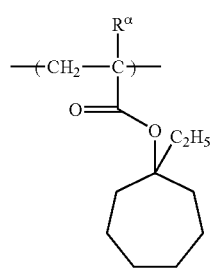
(a1-1-18) 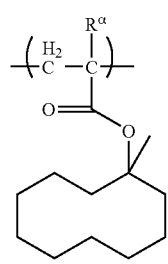
(a1-1-19) 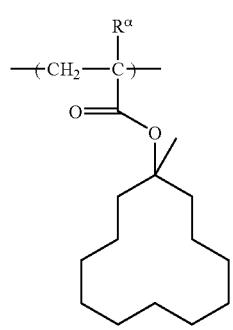
(a1-1-20) 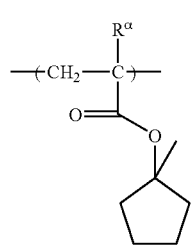
(a1-1-21) 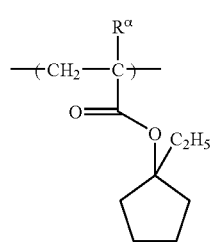
[Chemical Formula 36]
(a1-1-22) 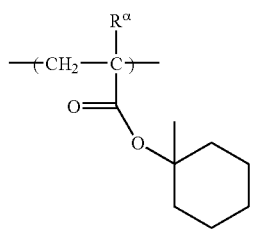
(a1-1-23) 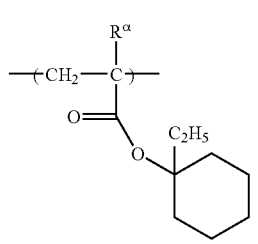
(a1-1-24) 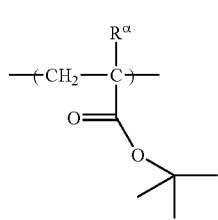
(a1-1-25) 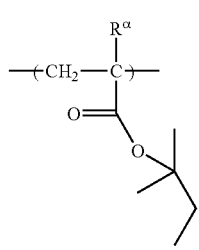
(a1-1-26) 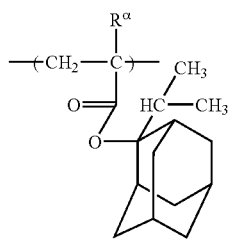
(a1-1-27) 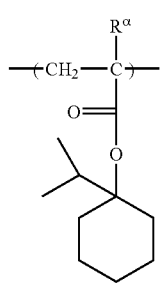

(a1-1-28) 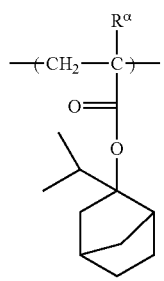
(a1-1-29) 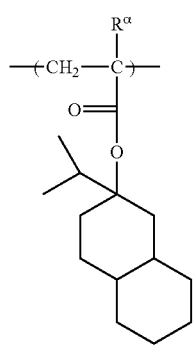
(a1-1-30) 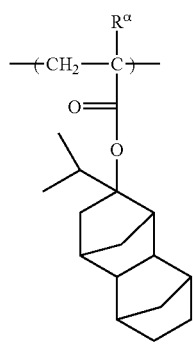
(a1-1-31) 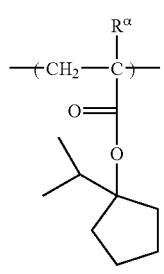
[Chemical Formula 37]
(a1-2-1) 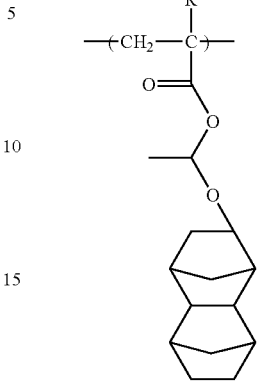
(a1-2-2) 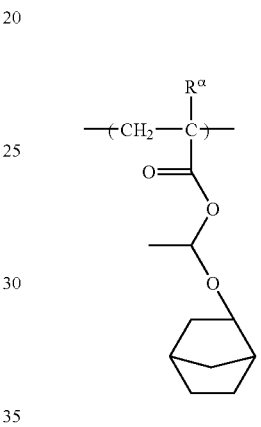
(a1-2-3) 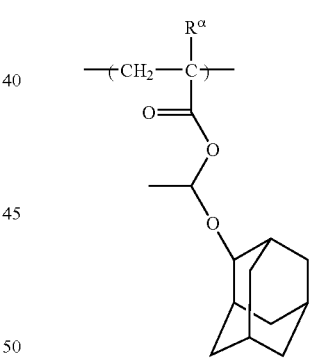
(a1-2-4) 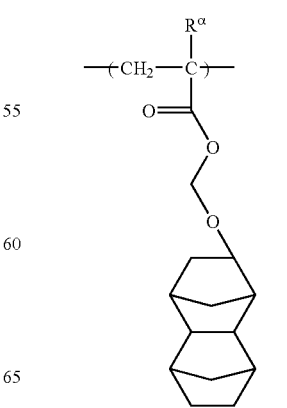

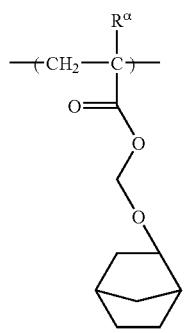 (a1-2-5)
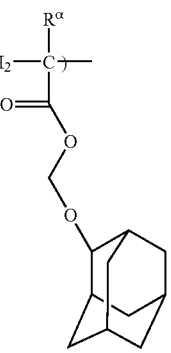 (a1-2-6)
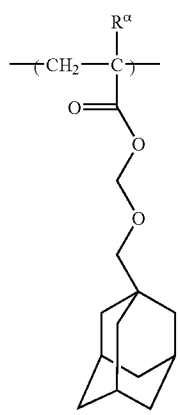 (a1-2-7)
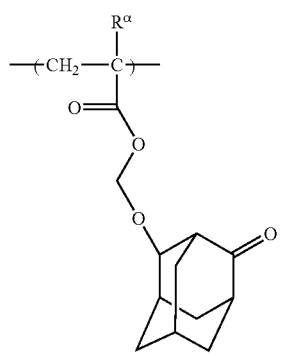 (a1-2-8)
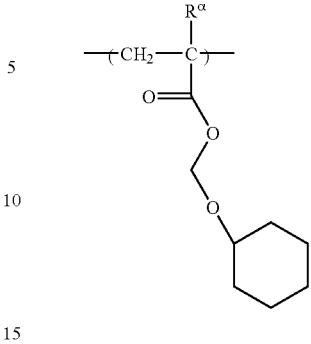 (a1-2-9)
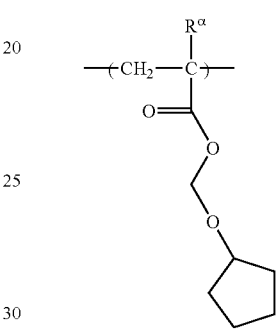 (a1-2-10)
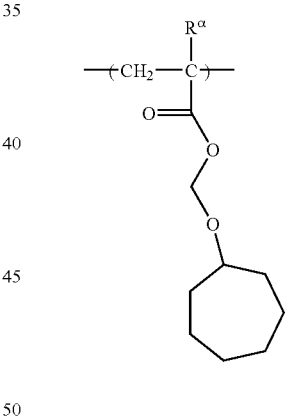 (a1-2-11)
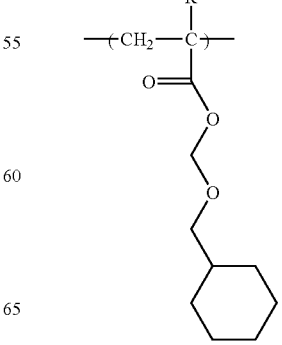 (a1-2-12)

(a1-2-13)
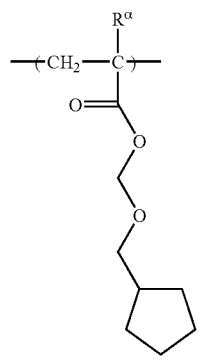
(a1-2-14)
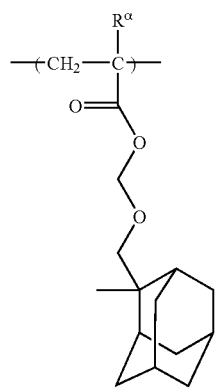
(a1-2-15)
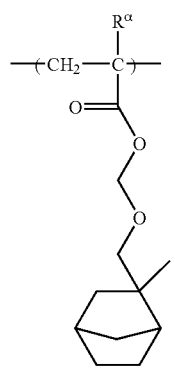
(a1-2-16)
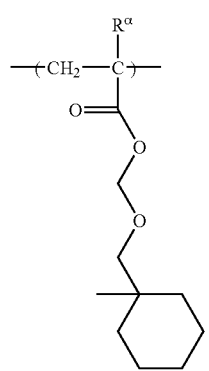
(a1-2-17)
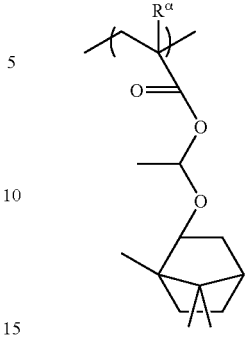
(a1-2-18)
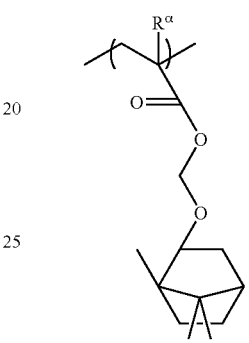
(a1-2-19)
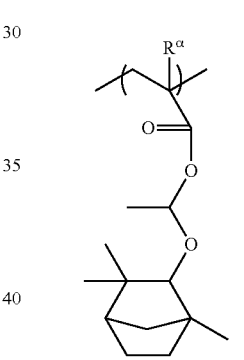
(a1-2-20)
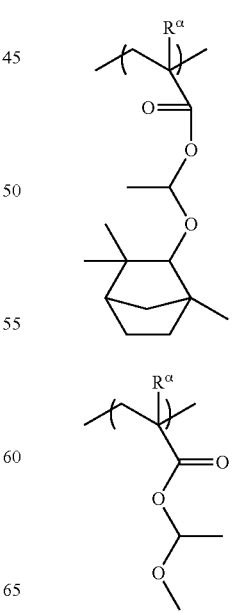
(a1-2-21)
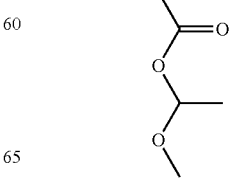

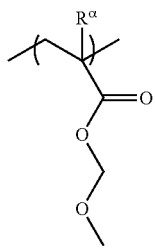 (a1-2-22)
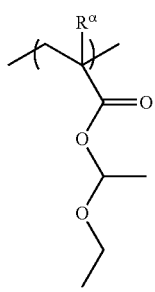 (a1-2-23)
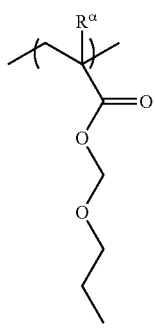 (a1-2-24)
[Chemical Formula 38]
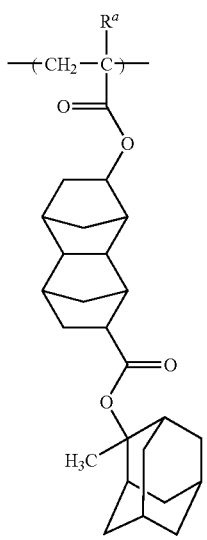 (a1-3-1)
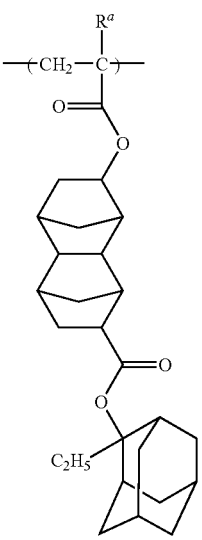 (a1-3-2)
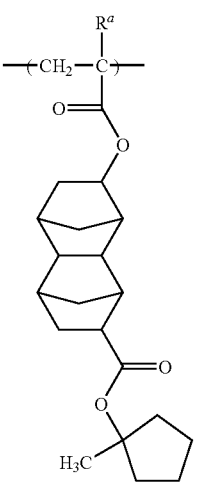 (a1-3-3)
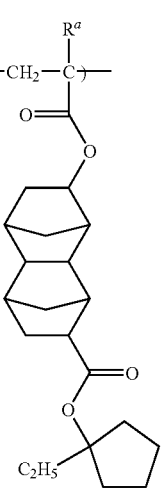 (a1-3-4)

(a1-3-5)
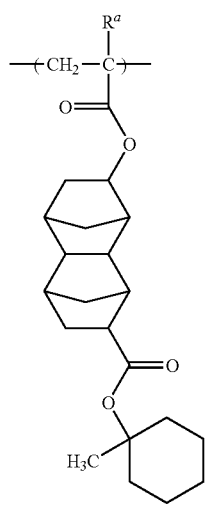
(a1-3-6)
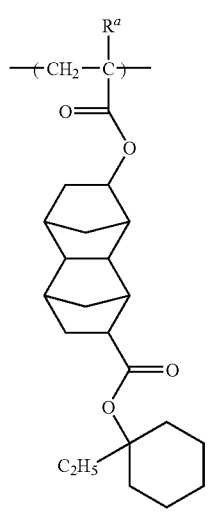
(a1-3-7)
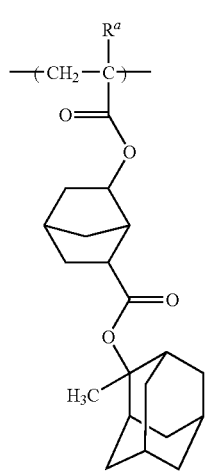
(a1-3-8)
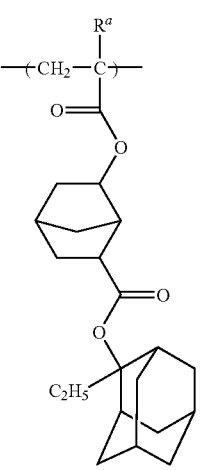
(a1-3-9)
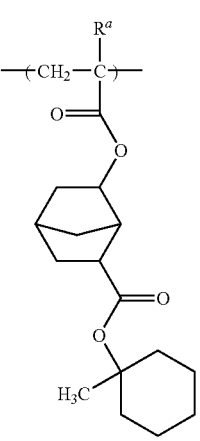
(a1-3-10)
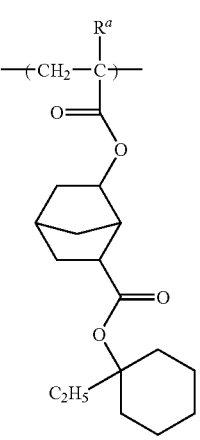

(a1-3-11) 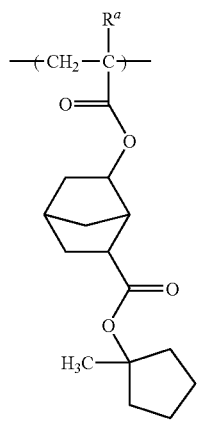
(a1-3-12) 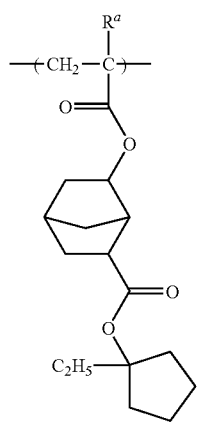
(a1-3-13) 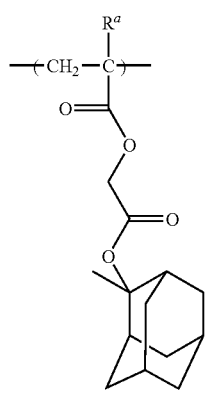
(a1-3-14) 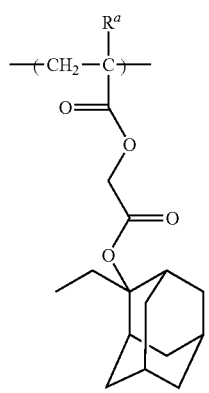
(a1-3-15) 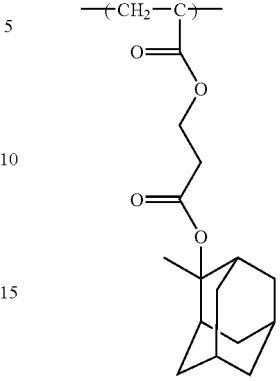
(a1-3-16) 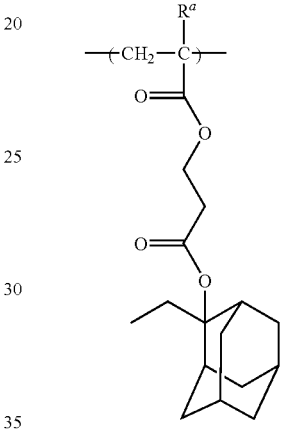
(a1-3-17) 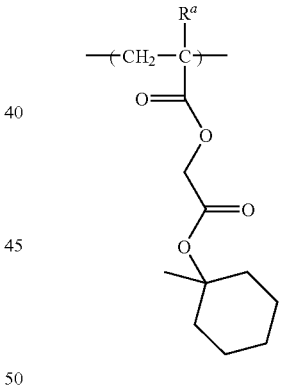
(a1-3-18) 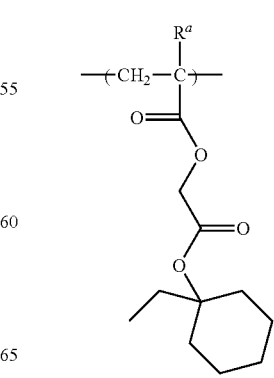

[Chemical Formula 39]
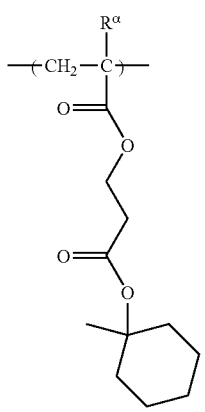
(a1-3-19)
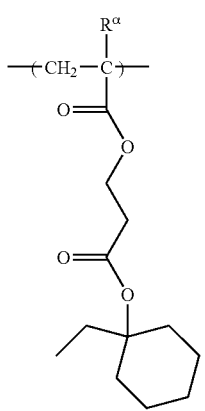
(a1-3-20)
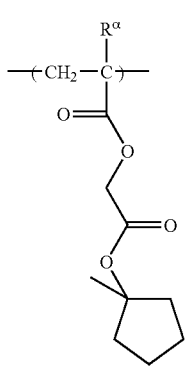
(a1-3-21)
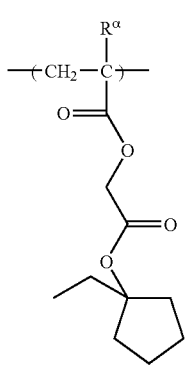
(a1-3-22)
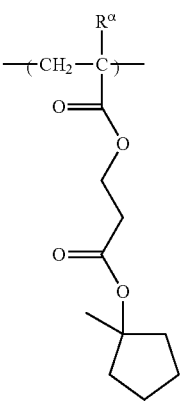
(a1-3-23)
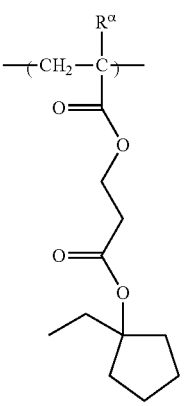
(a1-3-24)
[Chemical Formula 40]
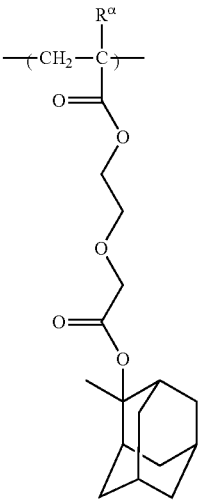
(a1-3-25)

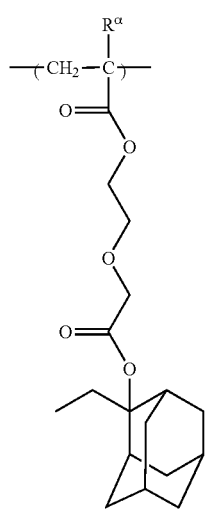
(a1-3-26)
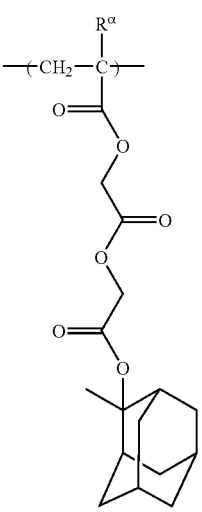
(a1-3-29)
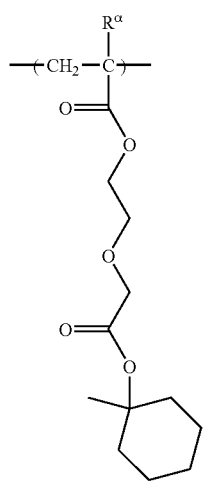
(a1-3-27)
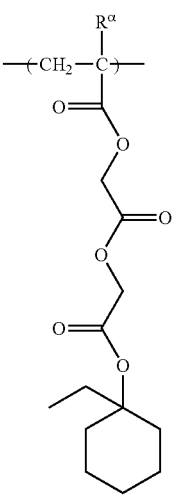
(a1-3-30)
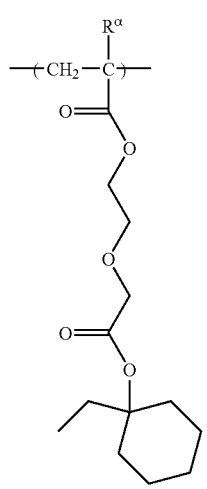
(a1-3-28)
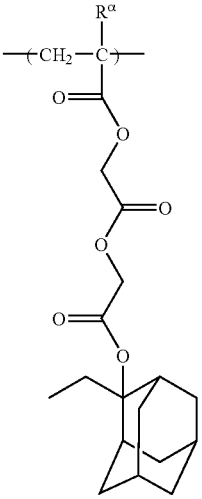
(a1-3-31)

(a1-3-32)
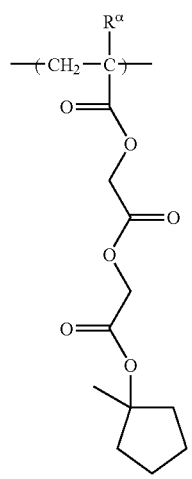
[Chemical Formula 41]
(a1-4-1)
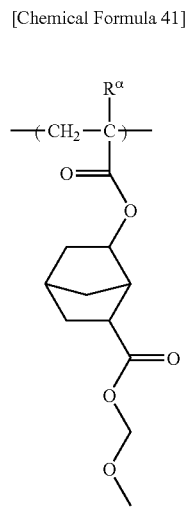
(a1-4-2)
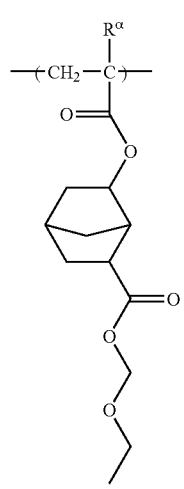
(a1-4-3)
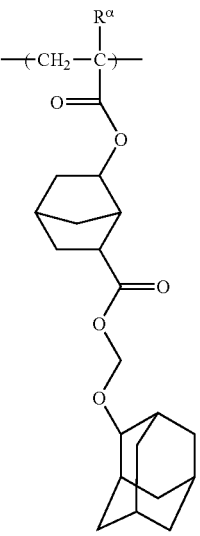
(a1-4-4)
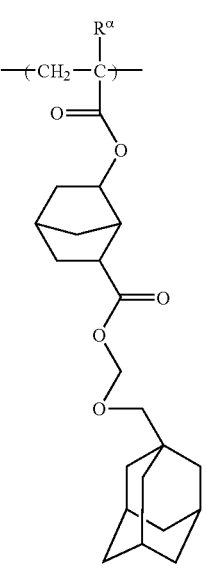
(a1-4-5)
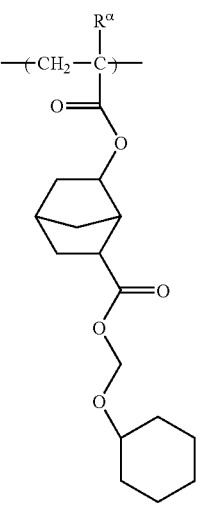

(a1-4-6)
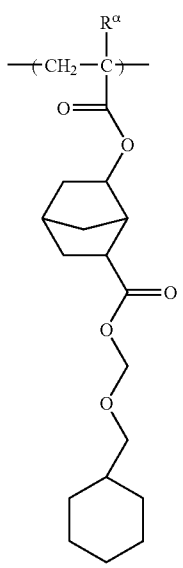
(a1-4-7)
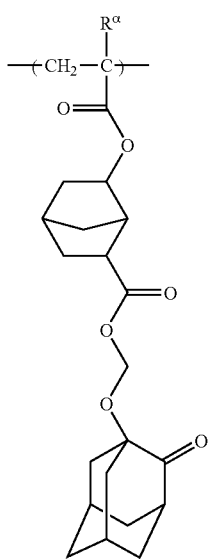
(a1-4-8)
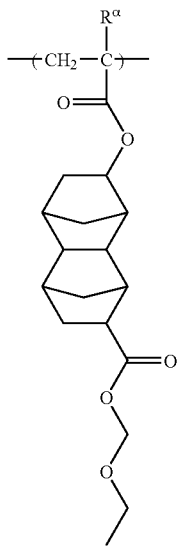
(a1-4-9)
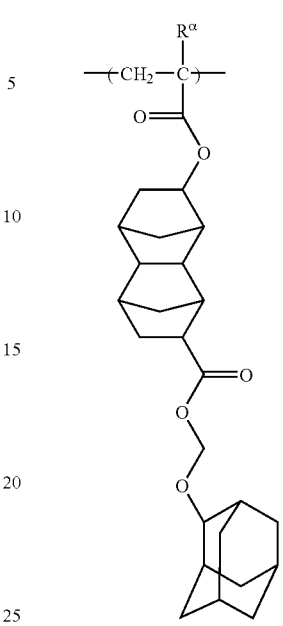
(a1-4-10)
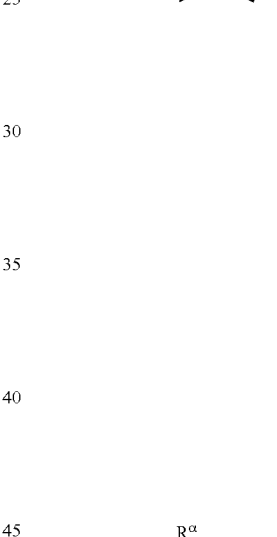
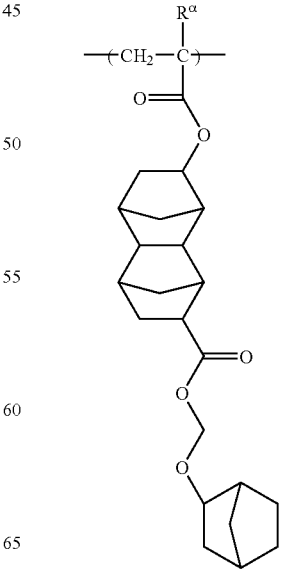

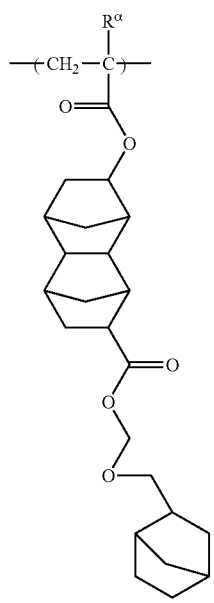
(a1-4-11)
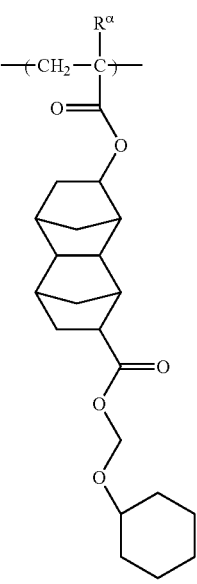
(a1-4-13)
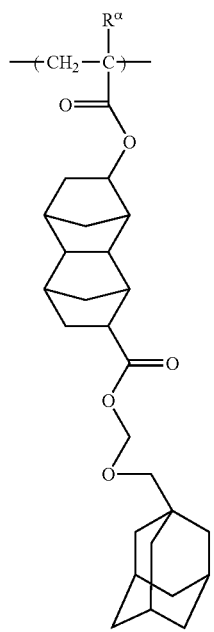
(a1-4-12)
(a1-4-14)

-continued (a1-4-15)

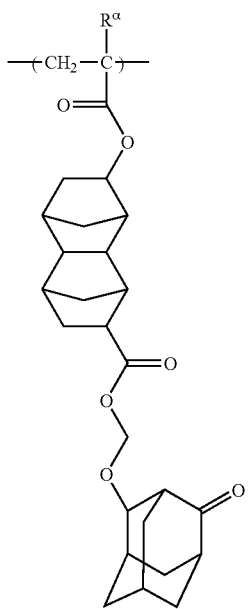

As the structural unit (a1), one type of structural unit may be used alone, or two or more types of structural units may be used in combination.

Among these, as the structural unit (a1), structural units represented by general formula (a1-1) or (a1-3) are preferable. More specifically, at least one structural unit selected from the group consisting of structural units represented by formulas (a1-1-1) to (a-1-1-4), (a1-1-20) to (a1-1-23) and (a1-3-25) to (a1-3-28) is more preferable.

Further, as the structural unit (a1), structural units represented by general formula (a1-1-01) shown below which includes the structural units represented by formulas (a1-1-1) to (a1-1-3), structural units represented by general formula (a1-1-02) shown below which includes the structural units represented by formulas (a1-1-16), (a1-1-17) and (a1-1-20) to (a1-1-23), structural units represented by general formula (a1-3-01) shown below which include the structural units represented by formulas (a1-3-25) and (a1-3-26), and structural units represented by general formula (a1-3-02) shown below which include the structural units represented by formulas (a1-3-27) to (a1-3-28) are also preferable.

[Chemical Formula 42]

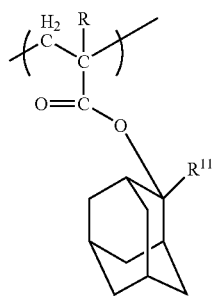

(a1-1-01)

(a1-1-02)

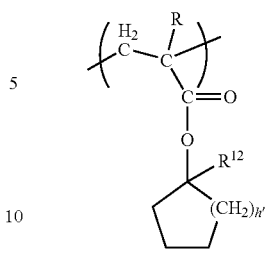

[In the formulas, R each independently represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 5 carbon atoms; and h' represents an integer of 1 to 6.]

In general formula (a1-1-01), R is the same as defined above.

The alkyl group for $R^{11}$ is the same as the alkyl group defined above for R, and is preferably a methyl group, an ethyl group or an isopropyl group.

In general formula (a1-1-02), R is the same as defined above.

The alkyl group for $R^{12}$ is the same as the alkyl group defined above for R, and is preferably a methyl group, an ethyl group or an isopropyl group.

h' is preferably 1 or 2, and most preferably 2.

[Chemical Formula 43]

(a1-3-01)

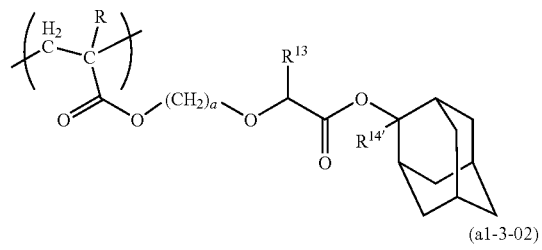

(a1-3-02)

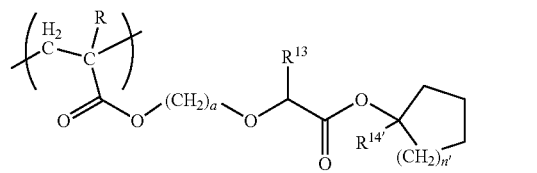

[In the formula, R each independently represents a hydrogen atom, an alkyl group of 1 to 5 carbon atoms or a halogenated alkyl group of 1 to 5 carbon atoms; $R^{14'}$ each independently represents an alkyl group of 1 to 5 carbon atoms; $R^{13}$ each independently represents a hydrogen atom or a methyl group; a each independently represents an integer of 1 to 10; and n' each independently represents an integer of 1 to 6.]

In general formulas (a1-3-01) and (a1-3-02), R is the same as defined above.

$R^{13}$ is preferably a hydrogen atom.

The alkyl group for $R^{14'}$ is the same as the alkyl group defined above for R, and is preferably a methyl group or an ethyl group.

a is preferably an integer of 1 to 8, more preferably an integer of 2 to 5, and most preferably 2.

n' is most preferably 1 or 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

Structural Unit (a2):

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the lactone-containing cyclic group of the structural unit (a2), there is no particular limitation, and any group may be used. Specific examples of lactone-containing monocyclic groups include a group in which one hydrogen atom has been removed from a 4- to 6-membered lactone ring, such as a group in which one hydrogen atom has been removed from β-propionolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 44]

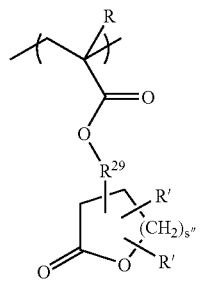

(a2-1)

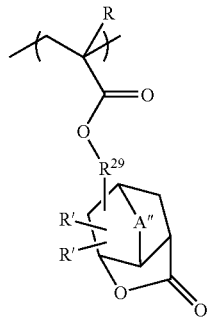

(a2-2)

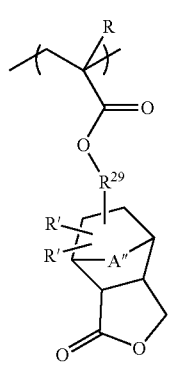

(a2-3)

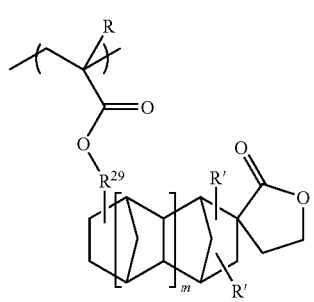

(a2-4)

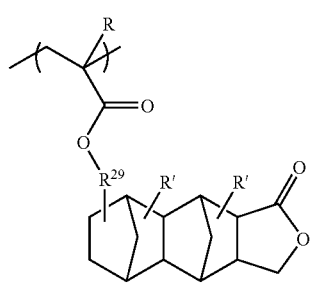

(a2-5)

[In the formulas, R each independently represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" each independently represents a hydrogen atom or an alkyl group; $R^{29}$ each independently represents a single bond or a divalent linking group; s" represents an integer of 0 to 2; A" each independently represents an oxygen atom, a sulfur atom or an alkylene group of 1 to 5 carbon atoms which may contain an oxygen atom or a sulfur atom; and m represents 0 or 1.]

In general formulas (a2-1) to (a2-5), R is the same as defined for R in the structural unit (a1).

Examples of the alkyl group of 1 to 5 carbon atoms for R' include a methyl group, an ethyl group, a propyl group, a n-butyl group and a tert-butyl group.

Examples of the alkoxy group of 1 to 5 carbon atoms for R' include a methoxy group, an ethoxy group, a n-propoxy group, a iso-propoxy group, a n-butoxy group and a tert-butoxy group.

In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples of such groups include groups in which one or more hydrogen atoms have been removed from a monocycloalkane such as cyclopentane or cyclohexane; and groups in which one or more hydrogen atoms have been removed from a polycycloalkane such as adamantine, norbornane, isobornane, tricyclodecane or tetracyclododecane.

As examples of A", the same groups as those described above for Q" in general formula (L2) can be given. A" is preferably an alkylene group of 1 to 5 carbon atoms, an oxygen atom (—O—) or a sulfur atom (—S—), and is more preferably an alkylene group of 1 to 5 carbon atoms or —O—. As the alkylene group of 1 to 5 carbon atoms, a methylene group or a dimethylmethylene group is more preferable, and a methylene group is particularly desirable.

$R^{29}$ represents a single bond or a divalent linking group. As examples of the divalent linking group for $R^{29}$, the same divalent linking groups as those described above for $Y^2$ in general formula (a1-0-2) can be given. Among these, an alkylene group, an ester bond (—C(=O)—O—) or a combination thereof is preferable. The alkylene group as a divalent linking group for $R^{29}$ is preferably a linear or branched alkylene group. Specific examples thereof include the same linear alkylene groups and branched alkylene groups as those described above for the aliphatic hydrocarbon group A in relation to $Y^2$.

As $R^{29}$, a single bond or —$R^{29'}$—C(=O)—O—[wherein $R^{29'}$ represents a linear or branched alkylene group] is particularly desirable. The linear or branched alkylene group for $R^{29'}$ preferably has 1 to 10 carbon atoms, more preferably 1 to 8 carbon atoms, and still more preferably 1 to 5 carbon atoms.

In general formula (a2-1), s" is preferably 1 or 2.

Specific examples of structural units represented by the aforementioned general formulas (a2-1) to (a2-5) are shown below. In the formulas shown below, $R^\alpha$ each independently represents a hydrogen atom, a methyl group or a trifluoromethyl group.

[Chemical Formula 45]

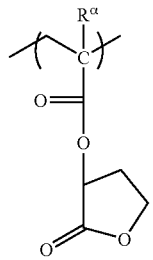
(a2-1-1)

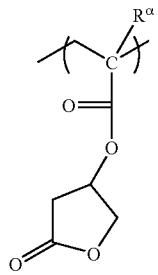
(a2-1-2)

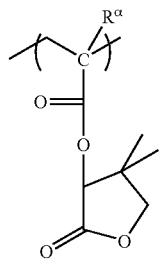
(a2-1-3)

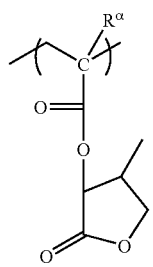
(a2-1-4)

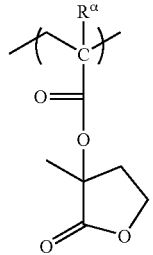
(a2-1-5)

-continued
(a2-1-6) 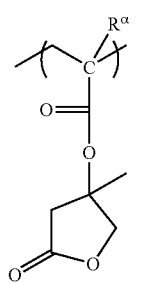
(a2-1-7) 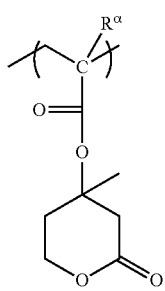
(a2-1-8) 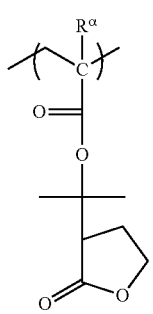
(a2-1-9) 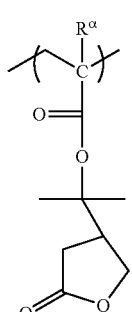
(a2-1-10) 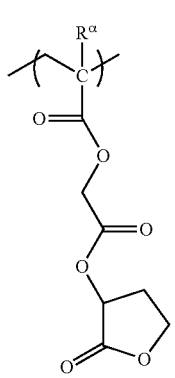
(a2-1-11) 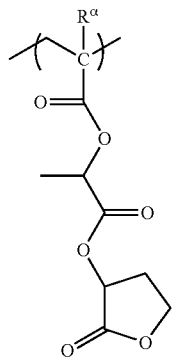
(a2-1-12) 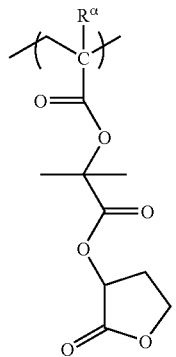
(a2-1-13) 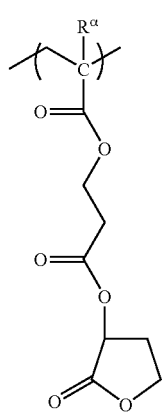
[Chemical Formula 46]
(a2-2-1) 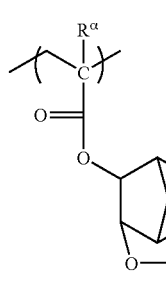

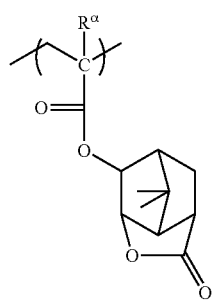 (a2-2-2)
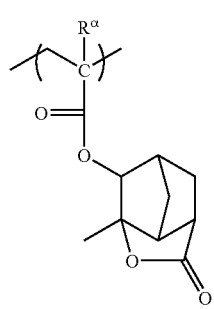 (a2-2-3)
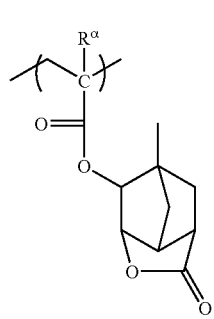 (a2-2-4)
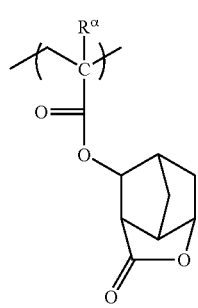 (a2-2-5)
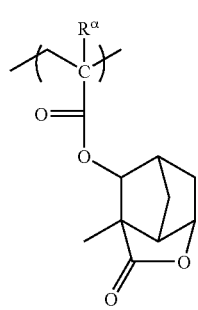 (a2-2-6)
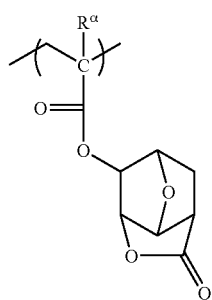 (a2-2-7)
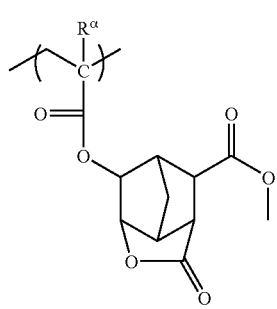 (a2-2-8)
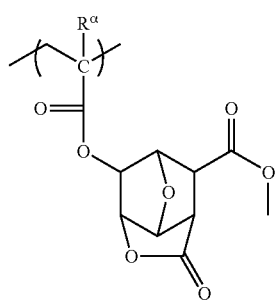 (a2-2-9)
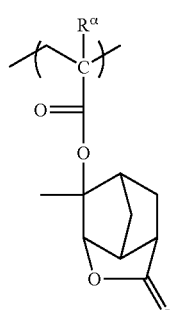 (a2-2-10)
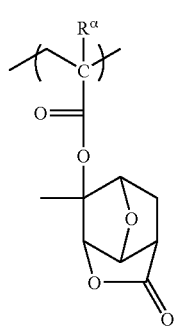 (a2-2-11)

(a2-2-12)
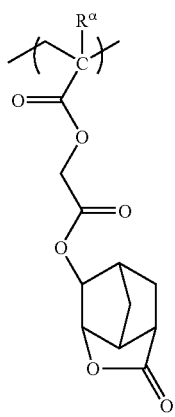
(a2-2-13)
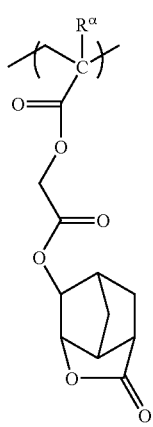
(a2-2-14)
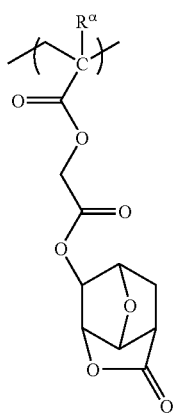
(a2-2-15)
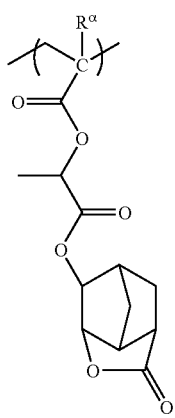
(a2-2-16)
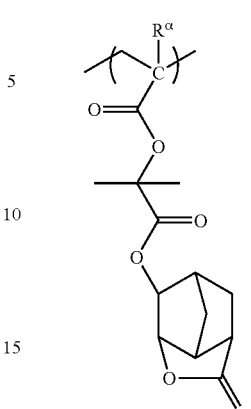
(a2-2-17)
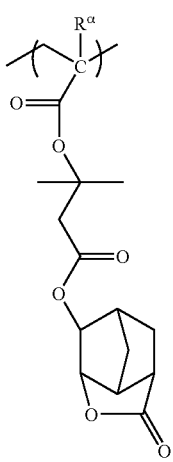
[Chemical Formula 47]
(a2-3-1)
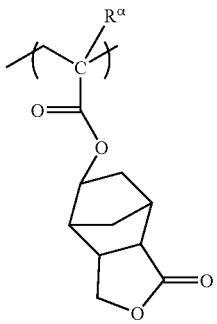
(a2-3-2)
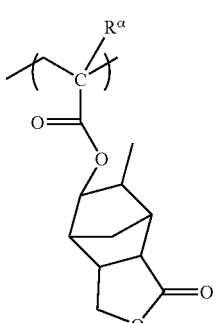

-continued
(a2-3-3)
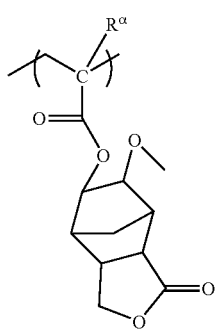
(a2-3-4)
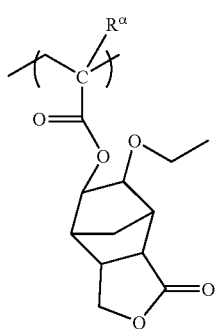
(a2-3-5)
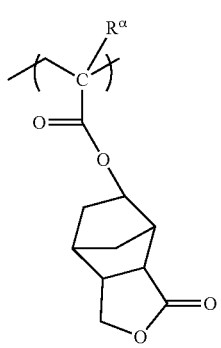
(a2-3-6)
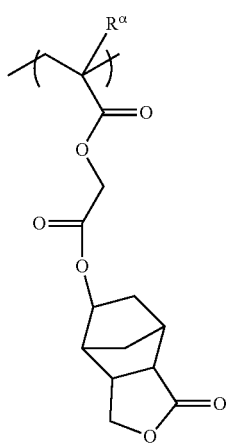
-continued
(a2-3-7)
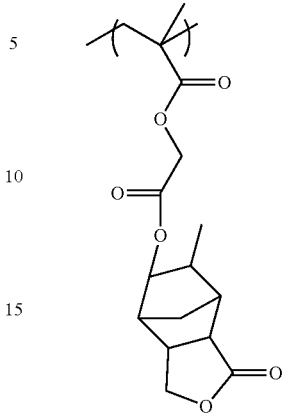
(a2-3-8)
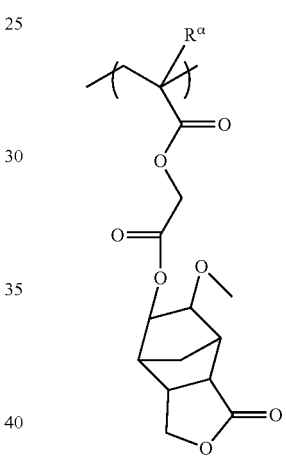
(a2-3-9)
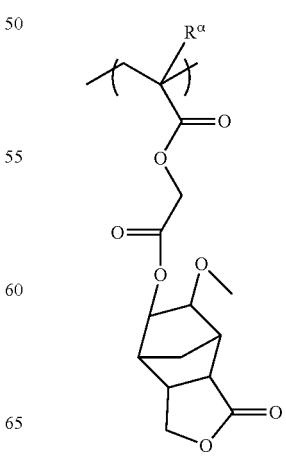

-continued
(a2-3-10)
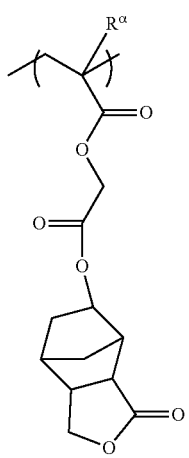
[Chemical Formula 48]
(a2-4-1)
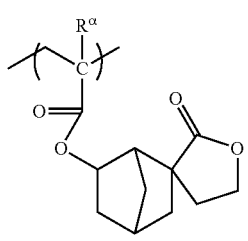
(a2-4-2)
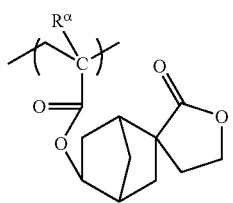
(a2-4-3)
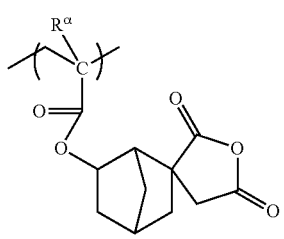
(a2-4-4)
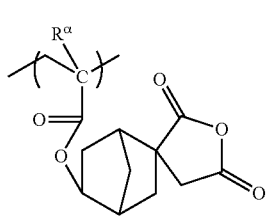
(a2-4-5)
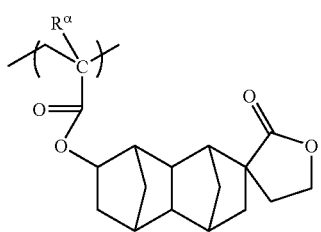
-continued
(a2-4-6)
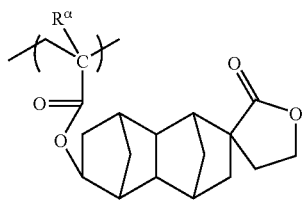
(a2-4-7)
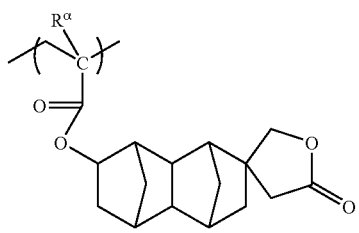
(a2-4-8)
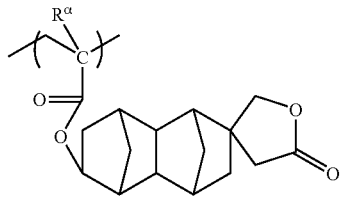
(a2-4-9)
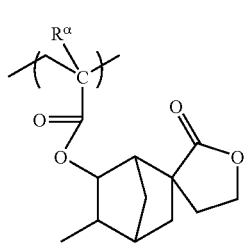
(a2-4-10)
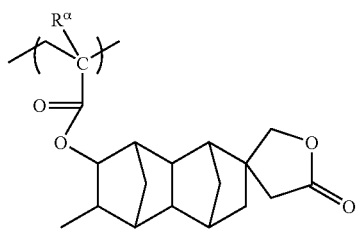
(a2-4-11)
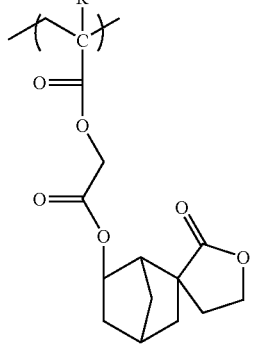

(a2-4-12)

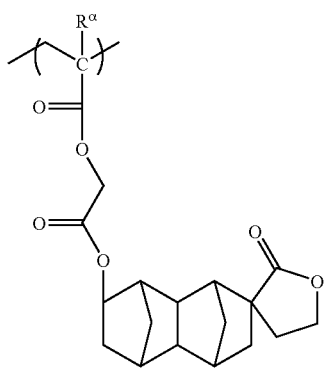

[Chemical Formula 49]

(a2-5-1)

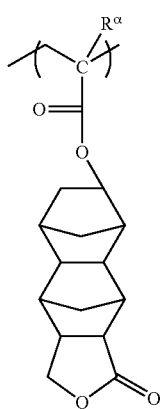

(a2-5-2)

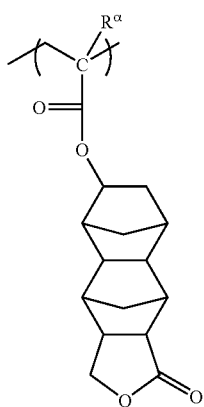

(a2-5-3)

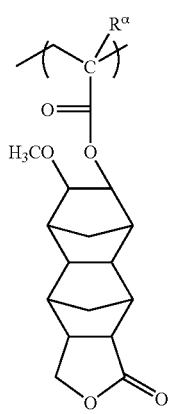

(a2-5-4)

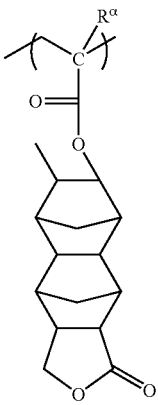

(a2-5-5)

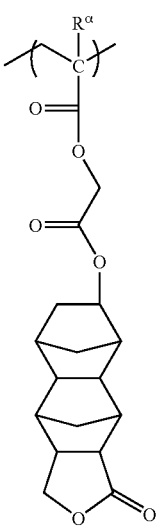

(a2-5-6)

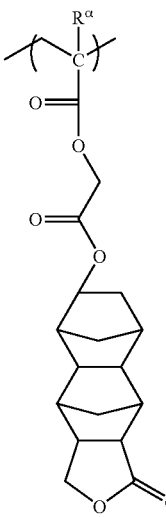

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is preferable to use at least one structural unit selected from the group consisting of structural units represented by formulas (a2-1-1), (a2-2-1), (a2-3-1) and (a2-3-5). In the component (A1), the amount of the structural unit (a2) based on the combined total of all structural units constituting the component (A1) is preferably 5 to 60 mol %, more preferably 10 to 50 mol %, and still more preferably 20 to 50 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the abovementioned range, a good balance can be achieved with the other structural units.

Structural Unit (a3):

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, a cyano group, a carboxyl group, or a fluorinated alcohol group (i.e., a hydroxyalkyl group in which some of the hydrogen atoms of the alkyl group have been substituted with fluorine atoms), although a hydroxyl group is particularly desirable.

In the structural unit (a3), the number of polar groups bonded to the aliphatic hydrocarbon group is not particularly limited, but is preferably within a range from 1 to 3, and is most preferably 1.

The aliphatic hydrocarbon group to which the polar groups are bonded may be either saturated or unsaturated, preferably saturated.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms. When the aliphatic hydrocarbon group is a monocyclic aliphatic hydrocarbon group, the monocyclic aliphatic hydrocarbon group preferably has 3 to 6 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2), and (a3-3) shown below, and the like are preferable.

[Chemical Formula 50]

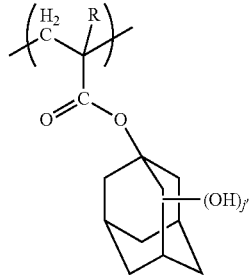

(a3-1)

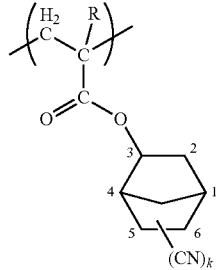

(a3-2)

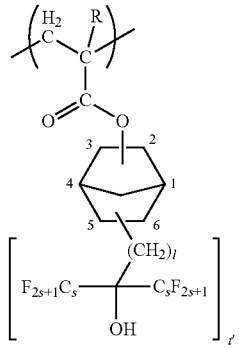

(a3-3)

[In the formulas, R is the same as defined above; j' is an integer of 1 to 3; k is an integer of 1 to 3; t' is an integer of 1 to 3; l is an integer of 1 to 5; and s is an integer of 1 to 3.]

In formula (a3-1), j' is preferably 1 or 2, and more preferably 1. When j' is 2, it is preferable that the hydroxyl groups be bonded to the 3rd and 5th positions of the adamantyl group. When j' is 1, it is preferable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1.

In formula (a3-3), it is preferable that the oxygen atom (—O—) of the carbonyloxy group be bonded to the 2nd or 3rd position of the norbornane ring. The fluorinated alkyl alcohol group is preferably bonded to the 5th or 6th position of the norbornyl group.

As the structural unit (a3), one type of structural unit may be used alone, or two or more types of structural units may be used in combination.

The amount of the structural unit (a3) within the component (A1) based on the combined total of all structural units constituting the component (A1) is preferably 5 to 50 mol %, more preferably 5 to 40 mol %, and still more preferably 5 to 25 mol %.

Structural Unit (a4):

The component (A1) may also include a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used. In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include structural units represented by general formulas (a4-1) to (a4-5) shown below.

[Chemical Formula 51]

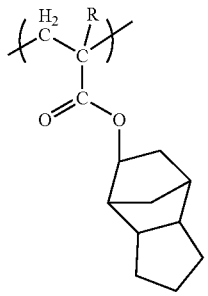
(a4-1)

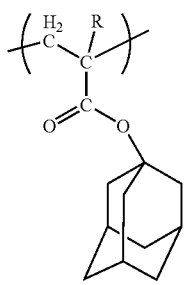
(a4-2)

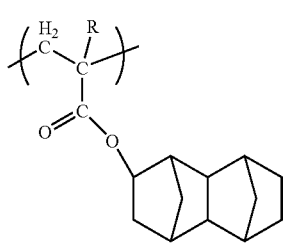
(a4-3)

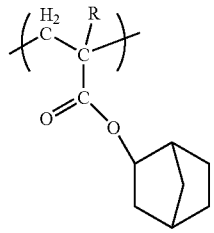
(a4-4)

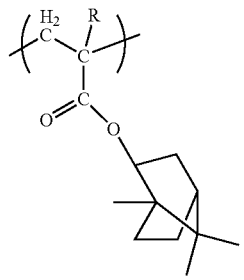
(a4-5)

[In the formulas, R is the same as defined above.]

When the component (A1) includes the structural unit (a4), the amount of the structural unit (a4) within the component (A1) based on the combined total of all the structural units that constitute the component (A1) is preferably within the range from 1 to 30 mol %, and more preferably from 10 to 20 mol %.

In the present invention, the component (A1) preferably contains a copolymer having the structural units (a1), (a2) and (a3). Examples of such copolymers include a copolymer consisting of the structural units (a1) and (a2) and (a3), and a copolymer consisting of the structural units (a1), (a2), (a3) and (a4).

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By ensuring that the weight average molecular weight is no more than the upper limit of the above-mentioned range, the component (A1) exhibits satisfactory solubility in a resist solvent when used as a resist. On the other hand, by ensuring that the weight average molecular weight is at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a low molecular weight compound that has a molecular weight of at least 500 and less than 4,000, contains a hydrophilic group, and also contains an acid dissociable, dissolution inhibiting group described above in connection with the component (A1). Examples thereof include compounds containing a plurality of phenol skeletons in which a part of the hydrogen atoms within hydroxyl groups have been substituted with the acid dissociable, dissolution inhibiting groups.

More specifically, preferable examples of the component (A2) include low molecular weight phenolic compounds that are known, for example, as sensitizers or heat resistance improvers for use in non-chemically amplified g-line or i-line resists, wherein a portion of the hydrogen atoms within hydroxyl group of these compounds have been substituted with the acid dissociable, dissolution inhibiting groups mentioned above. Examples of these low molecular weight phenolic compounds include bis(4-hydroxyphenyl)methane, bis(2,3,4-trihydroxyphenyl)methane, 2-(4-hydroxyphenyl)-2-(4' hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenolic compound is not limited to these examples.

Also, there are no particular limitations on the acid dissociable, dissolution inhibiting group, and suitable examples include the same acid dissociable, dissolution inhibiting groups as those described above in relation to the component (A1).

As the component (A), one type of component may be used alone, or two or more types may be used in combination.

In the resist composition of the present invention, the amount of the component (A) can be appropriately adjusted depending on the thickness of the resist film to be formed, and the like.

<Component (B)>

The component (B) includes an acid generator (B1) (hereafter, frequently referred to as "component (B1)") consisting of a compound represented by general formula (b1-1) above. The component (B1) is the same as the aforementioned compound of the present invention.

As the component (B1), one type may be used alone, or two or more types may be used in combination.

In the component (B), the amount of the component (B1) based on the total weight of the component (B) is preferably 25% by weight or more, more preferably 50% by weight or more, still more preferably 75% by weight or more, and may be even 100% by weight. By making the amount of the component (B1) at least as large as the lower limit of the above-mentioned range, lithography properties such as resolution, mask error factor (MEF), exposure margin (EL margin), and line width roughness (LWR) are improved. Further, the shape of the formed resist pattern is also improved.

In the resist composition of the present invention, the component (B) may further include an acid generator other than the aforementioned component (B1) (hereafter, referred to as "component (B2)").

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator in the component (B2), a compound represented by general formula (b-1) or (b-2) shown below can be preferably used.

[Chemical Formula 52]

[In formulas above, each of $R^{1"}$ to $R^{3"}$ independently represents an aryl group which may have a substituent or an alkyl group, and two of $R^{1"}$ to $R^{3"}$ may be bonded to each other to form a ring with the sulfur atom in the formula; $R^{4"}$ each independently represents an alkyl group or a fluorinated alkyl group; and $R^{5"}$ and $R^{6"}$ each independently represents an aryl group which may have a substituent or an alkyl group.]

In formula (b-1), $R^{1"}$ to $R^{3"}$ are the same as defined above for $R^{1"}$ to $R^{3"}$ in formula (b'-1).

The alkyl group for $R^{4"}$ may be any of linear, branched or cyclic, or a combination thereof.

When the alkyl group is a linear or branched alkyl group, as the alkyl group, the same linear or branched alkyl groups as those described in connection with $R^{1"}$ to $R^{3"}$ above can be mentioned. The linear or branched alkyl group for $R^{4"}$ preferably has 1 to 10 carbon atoms, more preferably 1 to 8 carbon atoms, and most preferably 1 to 4 carbon atoms.

When the alkyl group is a cyclic alkyl group, as the alkyl group, the same cyclic alkyl groups as those described in connection with $R^{1"}$ above can be mentioned. The cyclic alkyl group for $R^{4"}$ preferably has 4 to 15 carbon atoms, more preferably 4 to 10 carbon atoms, and most preferably 6 to 10 carbon atoms.

The fluorinated alkyl group for $R^{4"}$ preferably has 1 to 10 carbon atoms, more preferably 1 to 8 carbon atoms, and most preferably 1 to 4 carbon atoms.

Further, the fluorination ratio of the fluorinated alkyl group (percentage of the number of fluorine atoms within the fluorinated alkyl group, based on the total number of fluorine atoms and hydrogen atoms within the alkyl group) is preferably from 10 to 100%, more preferably from 50 to 100%, and a fluorinated alkyl group in which all hydrogen atoms are substituted with fluorine atoms (i.e., a perfluoroalkyl group) is particularly desirable because the acid strength increases.

R⁴'' is most preferably a linear or cyclic alkyl group or a fluorinated alkyl group.

In formula (b-2), R⁵'' and R⁶'' are the same as defined above for R⁵'' and R⁶'' in formula (b'-1).

As R⁴'' in formula (b-2), the same groups as those mentioned above for R⁴'' in formula (b-1) can be used.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Further, it is also possible to use onium salts in which the anion moiety of these onium salts is replaced by methanesulfonate, n-propanesulfonate, n-butanesulfonate, n-octanesulfonate, 1-adamantanesulfonate, 2-norbornanesulfonate, d-camphor-10-sulfonate, benzenesulfonate, perfluorobenzenesulfonate, or p-toluenesulfonate.

Furthermore, onium salt-based acid generators in which the anion moiety (i.e., R⁴''SO₃⁻) in general formula (b-1) or (b-2) is replaced by an anion moiety represented by general formula (b-3) or (b-4) shown below (the cation moiety is the same as (b-1) or (b-2)) may also be used.

[Chemical Formula 53]

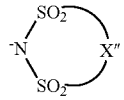

(b-3)

(b-4)

[In the formulas, X'' represents an alkylene group of 2 to 6 carbon atoms in which at least one hydrogen atom has been substituted with a fluorine atom; and Y'' and Z'' each independently represents an alkyl group of 1 to 10 carbon atoms in which at least one hydrogen atom has been substituted with a fluorine atom.]

X'' represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y'' and Z'' independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X'' or those of the alkyl group for Y'' and Z'' within the above-mentioned range of the number of carbon atoms, the more the solubility in a resist solvent is improved.

Further, in the alkylene group for X'' or the alkyl group for Y'' and Z'', it is preferable that the number of hydrogen atoms substituted with fluorine atoms is as large as possible because the acid strength increases and the transparency to high energy radiation of 200 nm or less or electron beam is improved. The percentage of the fluorine atoms within the alkylene group or alkyl group, i.e., the fluorination ratio is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Further, onium salt-based acid generators in which the anion moiety (i.e., R⁴''SO₃⁻) in general formula (b-1) or (b-2) is replaced by Ra—COO—[wherein Ra represents an alkyl group or a fluorinated alkyl group] (the cation moiety is the same as (b-1) or (b-2)) may also be used.

As Ra, the same groups as those described above for R⁴'' can be used.

Specific examples of the group represented by the formula "Ra—COO—" include a trifluoroacetate ion, an acetate ion, and a 1-adamantanecarboxylic acid ion.

Furthermore, as an onium salt-based acid generator, a sulfonium salt having a cation moiety represented by general formula (b-5) or (b-6) above and an anion moiety other than the aforementioned anion moiety included in the component (B1) may also be used.

As such anion moieties, the same anion moieties for onium salt-based acid generators which have been proposed can be used. Examples thereof include alkylsulfonic acid ions or fluorinated alkylsulfonic acid ions such as anion moieties ($R^{4"}SO_3^-$) for onium salt-based acid generators represented by general formula (b-1) or (b-2) shown above; and anion moieties represented by general formula (b-3) or (b-4) shown above. Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propanesulfonate ion and a nonafluoro-n-butylsulfonate ion.

in the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 54]

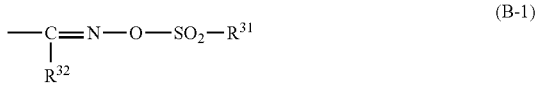

(B-1)

(In formula (B-1), $R^{31}$ and $R^{32}$ each independently represents an organic group.)

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or an aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. As the alkyl group or aryl group for $R^{32}$, the same alkyl groups or aryl groups as those described above for $R^{31}$ can be used.

As $R^{32}$, a cyano group, an alkyl group of 1 to 8 carbon atoms having no substituent, or a fluorinated alkyl group of 1 to 8 carbon atoms is particularly desirable.

Preferable examples of the oxime sulfonate-based acid generator include compounds represented by general formula (B-2) or (B-3) shown below.

[Chemical Formula 55]

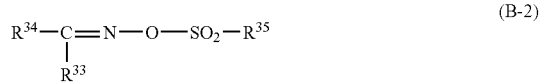

(B-2)

[In formula (B-2), $R^{33}$ represents a cyano group, an alkyl group having no substituent or a halogenated alkyl group; $R^{34}$ represents an aryl group; and $R^{35}$ represents an alkyl group having no substituent or a halogenated alkyl group.]

[Chemical Formula 56]

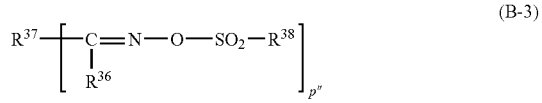

(B-3)

[In formula (B-3), $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.]

In general formula (8-2) above, the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be used.

[Chemical Formula 57]

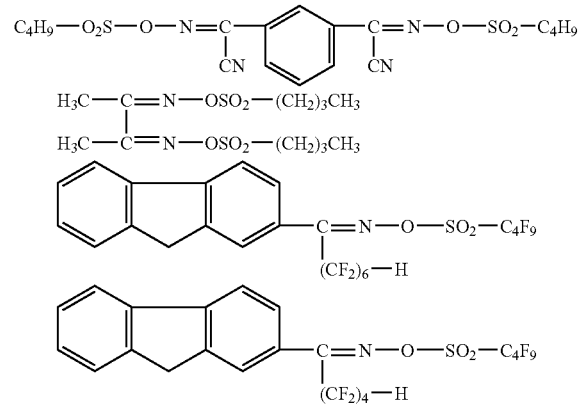

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazornethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be mentioned.

As the component (B2), any one of these acid generators may be used alone, or two or more types of acid generators may be used in combination.

In the resist composition of the present invention, the amount of the component (B) relative to 100 parts by weight of the component (A) is preferably from 0.5 to 50 parts by weight, and more preferably from 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

The resist composition of the present invention may further contain a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of 1 to 20 carbon atoms (i.e., alkylamines or alkyl alcohol amines), and cyclic amines.

Specific examples of alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, tri-n-octanolamine, stearyldiethanolamine and laurildiethanolamine. Among these, trialkylamines and/or alkyl alcohol amines are preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Further, aliphatic amines other than these aliphatic amines described above may also be used. Examples of other aliphatic amines include tris(2-methoxymethoxyethyl)amine, tris {2-(2-methoxyethoxy)ethyl}amine, tris {2-(2-methoxyethoxymethoxy)ethyl}amine, tris {2-(1-methoxyethoxy)ethyl}amine, tris{2-(1-ethoxyethoxy)ethyl}amine, tris{2-(1-ethoxypropoxy)ethyl}amine and tris[2-{2-(2-hydroxyethoxy)ethoxy}ethyl]amine.

Further, as the component (D), an aromatic amine may also be used. Examples of aromatic amines include aniline, 2,6-diisopropylaniline, pyridine, 4-dimethylaminopyridine, pyrrole, indole, pyrazole, imidazole and derivatives thereof, diphenylamine, triphenylamine and tribenzylamine.

These compounds can be used either alone, or in combinations of two or more different compounds.

The component (D) is typically used in an amount within a range from 0.01 to 5.0 parts by weight, relative to 100 parts by weight of the component (A). By ensuring that the amount of the component (D) is within the above-mentioned range, the shape of the resist pattern and the post exposure stability of the latent image formed by the pattern-wise exposure of the resist layer are improved.

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent>

The resist composition of the present invention can be prepared by dissolving the respective components for the resist composition described above in an organic solvent (hereafter, frequently referred to as "component (S)").

The component (S) may be any organic solvent which can dissolve the respective components to give a uniform solution, and one or more kinds of any organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethyl-benzene, diethylbenzene, pentylbenzene, isopropylbenzene, toluene, xylene, cymene and mesitylene.

These solvents may be used individually, or as a mixed solvent containing two or more different solvents.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably from 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) used is not particularly limited, and is appropriately adjusted to a concentration which enables coating of a coating solution to a substrate, depending on the thickness of the coating film. In general, the component (S) is used in an amount such that the solid content of the resist composition becomes within the range from 1 to 20% by weight, and preferably from 2 to 15% by weight.

The resist composition of the present invention described above and the component (B1) blended in the resist composition are novel, and are essentially unknown in the art.

Further, the lithography properties are also improved since the component (B1) is included as the component (B). For example, resist patterns with higher resolution can be formed, and mask reproducibility (e.g., mask error factor (MEF) or the like) and exposure margin (EL margin) when forming a resist pattern are also satisfactory. Further, the shape of the formed resist pattern is also favorable exhibiting a high degree of rectangularity. Such effects are particularly marked when $R^X$ in general formula (b1-1) above has a ring within the structure thereof as the component (B1).

The reasons why these effects can be achieved has not been elucidated yet, but are presumed as follows. That is, as conventional onium salt-based acid generators, those having a perfluoroalkylsulfonic acid ion as an anion (acid) have been mainly used. However, such onium salt-based acid generators exhibit low compatibility with an alkali developing solution due to the structure thereof, and are hardly distributed uniformly within the resist films, and thus, the diffusion length of the acid generated upon exposure is also considered to be long. Therefore, it is presumed that these factors have been adversely affecting the above-mentioned lithography properties of the resist composition in which these acid generators are added.

On the other hand, the component (B1) includes an anion having a structure in which $R^X$—S(=O)$_2$—O—$R^1$—O—C(=O)— containing a sulfonyl group or carbonyl group serving as a polar group has been introduced to a "$Y^1$—SO$_3^-$" skeleton. As a result, the anion of the component (B1) exhibits a high polarity and has a three-dimensionally bulky structure, as compared to a perfluoroalkylsulfonic acid ion such as nonafluorobutanesulfonate which has been used as an anion moiety of a conventional acid generator. By virtue of the intermolecular force due to the high polarity (for example, interactions with the component (A)), and the three-dimensionally bulky structure, it is presumed that diffusion of the anion within the resist film is chemically and physically suppressed, as compared to the anion moiety of a conventional acid generator. Therefore, the diffusion of anion (acid) generated from the component (B) upon exposure in exposed regions to unexposed regions can be suppressed. As a result, it is presumed that the difference in the solubility within the alkali developing solution of the unexposed portions and the exposed portions (namely, the solubility contrast) is improved, and the above-mentioned effects can be achieved.

Furthermore, because the alkyl chain of $Y^1$ has 1 to 4 carbon atoms, the alkyl chain exhibits an excellent decomposability, as compared to, for example, a perfluoroalkyl chain of 6 to 10 carbon atoms which is hardly decomposable, and is also excellent in terms of handling in consideration of bioaccumulation.

<<Method of Forming a Resist Pattern>>

The method of forming a resist pattern according to the present invention includes: applying a resist composition of the present invention to a substrate to form a resist film on the substrate; subjecting the resist film to exposure, and subjecting the resist film to alkali developing to form a resist pattern.

Each of the steps in the method for forming a resist pattern according to the present invention can be conducted by using conventional techniques with the exception that the resist composition of the present invention is used, and can be performed, for example, as follows. Firstly, a resist composition according to the present invention is applied onto a substrate using a spinner or the like, and a prebake (post applied bake (PAB)) is conducted at a temperature of about 80 to 150° C. for 40 to 120 seconds, preferably 60 to 90 seconds, to form a resist film. Following selective exposure of the thus formed resist film, either by exposure through a mask pattern using an exposure apparatus such as an ArF exposure apparatus, an electron beam lithography apparatus or an EUV exposure apparatus; or by patterning via direct irradiation with an electron beam without using a mask pattern, post exposure baking (PEB) is conducted under temperature conditions of about 80 to 150° C. for 40 to 120 seconds, preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the developing.

In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

EXAMPLES

As follows is a more detailed description of the present invention based on a series of examples, although the scope of the present invention is by no way limited by these examples.

In the following Synthesis Examples, "room temperature" was 23° C.

Further, in the NMR analysis, tetramethylsilane (TMS) was used as an internal standard in $^1$H-NMR spectrometry, and hexafluorobenzene was used as an internal standard in $^{19}$F-NMR spectrometry (the peak of hexafluorobenzene was regarded as −160 ppm).

Synthesis Example 1-1

Precursor Compound: Synthesis of Anion-1

7.8 g of a compound represented by the chemical formula A shown below and 26 g of acetonitrile were placed in a flask under a nitrogen atmosphere and cooled to 5° C. An acetonitrile solution containing 6.7 g of 10-camphorsulfonyl chloride was added dropwise thereto over 10 minutes, followed by the dropwise addition of an acetonitrile solution containing 2 g of pyridine over 20 minutes while maintaining the temperature at 5° C. or less, and the resulting mixture was then stirred at 5° C. for 16 hours. Thereafter, the mixture was concentrated under reduced pressure, and the obtained concentrate was dissolved in 27 g of dichloromethane, and the organic phase (dichloromethane phase) was washed with water. The dichloromethane phase was collected and added dropwise to 350 g of t-butylmethyl ether. Then, the supernatant was removed by decantation, thereby obtaining 9.5 g of an objective compound (Anion-1) in the form of an oily substance.

The obtained compound was analyzed by NMR, and the structure thereof was identified based on the results shown below.

$^1$H-NMR (DMSO-d6, 400 MHz): δ (ppm)=15.52 (brs, 1H, NH), 8.96 (dd, 2H, pyridine), 8.67 (dt, 1H, pyridine), 8.13 (dt, 2H, pyridine), 4.50-4.54 (m, 4H, $OCH_2CH_2O$), 3.57 (d, 1H, $CH_2SO_2$), 3.36 (sd, 1H, $CH_2SO_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, $CH_3$), 0.84 (s, 3H, $CH_3$)

$^{19}$F-NMR (DMSO-d6, 376 MHz): δ (ppm)=−106.5

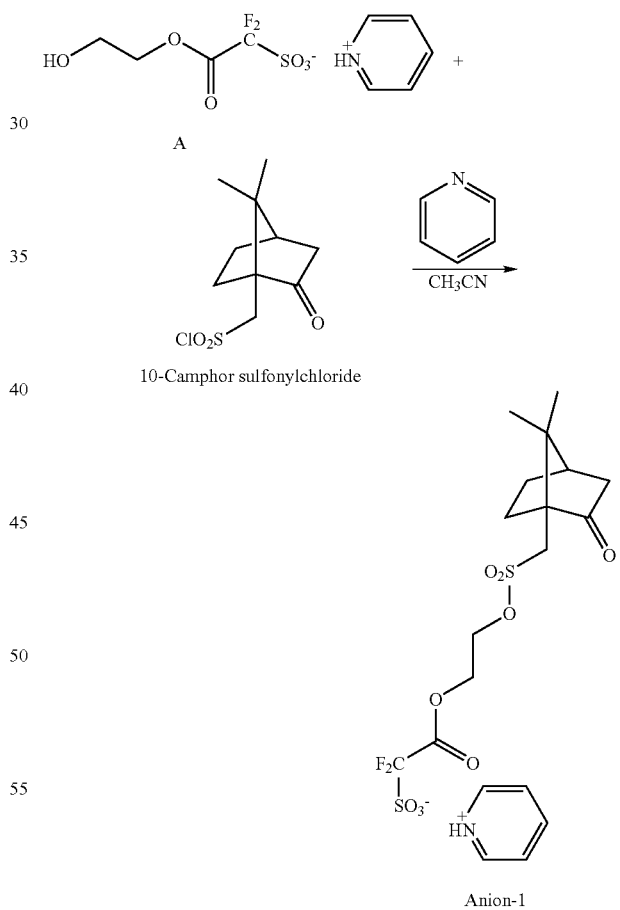

[Chemical Formula 58]

Synthesis Example 1-2

Precursor Compound: Synthesis of Anion-2

18.7 g of a compound represented by the chemical formula C shown below and 52 g of acetonitrile were placed in a flask under a nitrogen atmosphere and cooled to 5° C. An acetonitrile solution containing 10.3 g of 10-camphorsulfonyl chloride was added dropwise thereto over 10 minutes, followed by the dropwise addition of an acetonitrile solution containing 6.6 g of isoquinoline over 40 minutes while maintaining the temperature at 5° C. or less. Thereafter, the temperature was raised to room temperature, and the resulting mixture was stirred at room temperature for 21 hours. Then, the mixture was concentrated under reduced pressure, and the obtained concentrate was dissolved in 110 g of dichloromethane, and the organic phase (dichloromethane phase) was washed with water. The dichloromethane phase was collected and added dropwise to 550 g of t-butylmethyl ether, and the resulting supernatant was then removed by decantation. This operation was repeated twice and the resultant was then dried under reduced pressure, thereby obtaining 18.1 g of an objective compound (Anion-2) in the form of an oily substance.

The obtained compound was analyzed by NMR, and the structure thereof was identified based on the results shown below.

$^1$H-NMR (DMSO-d6, 400 MHz): δ (ppm)=15.60 (brs, 1H, NH), 9.87 (s, 1H, cation), 8.66 (d, 1H, cation), 8.52 (d, 1H, cation), 8.49 (d, 1H, cation), 8.31 (d, 1H, cation), 8.19 (t, 1H, cation), 8.01 (t, 1H, cation), 4.50-4.54 (m, 4H, OCH$_2$CH$_2$O), 3.57 (d, 1H, CH$_2$SO$_2$), 3.36 (d, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.4

Synthesis Example 1-3

Precursor Compound: Synthesis of Anion-3

8.6 g of a compound represented by the chemical formula D shown below and 26 g of acetonitrile were placed in a flask under a nitrogen atmosphere and cooled to 5° C. An acetonitrile solution containing 6.7 g of 10-camphorsulfonyl chloride was added dropwise thereto over 10 minutes, followed by the dropwise addition of an acetonitrile solution containing 2.6 g of triethylamine over 30 minutes while maintaining the temperature at 5° C. or less. Thereafter, the temperature was raised to room temperature, and the resulting mixture was stirred at room temperature for 21 hours. Then, the mixture was concentrated under reduced pressure, and the obtained concentrate was dissolved in 140 g of dichloromethane, and the organic phase (dichloromethane phase) was washed with water. The dichloromethane phase was collected and added dropwise to 700 g of t-butylmethyl ether, and the resulting supernatant was then removed by decantation. This operation was repeated twice and the resultant was then dried under reduced pressure, thereby obtaining 7.6 g of an objective compound (Anion-3) in the form of an oily substance.

The obtained compound was analyzed by NMR, and the structure thereof was identified based on the results shown below.

$^1$H-NMR (DMSO-d6, 400 MHz): δ (ppm)=4.50-4.54 (m, 4H, OCH$_2$CH$_2$O), 3.57 (d, 1H, CH$_2$SO$_2$), 3.36 (d, 1H, CH$_2$SO$_2$), 3.14 (q, 6H, CH$_2$-cation), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.22 (t, 9H, CH$_3$-cation), 1.04 (s, 3H, CH$_3$), 0.84 (s, 3H, CH$_3$)

$^{19}$F-NMR (DMSO-d6, 376 MHz): δ (ppm)=−106.4

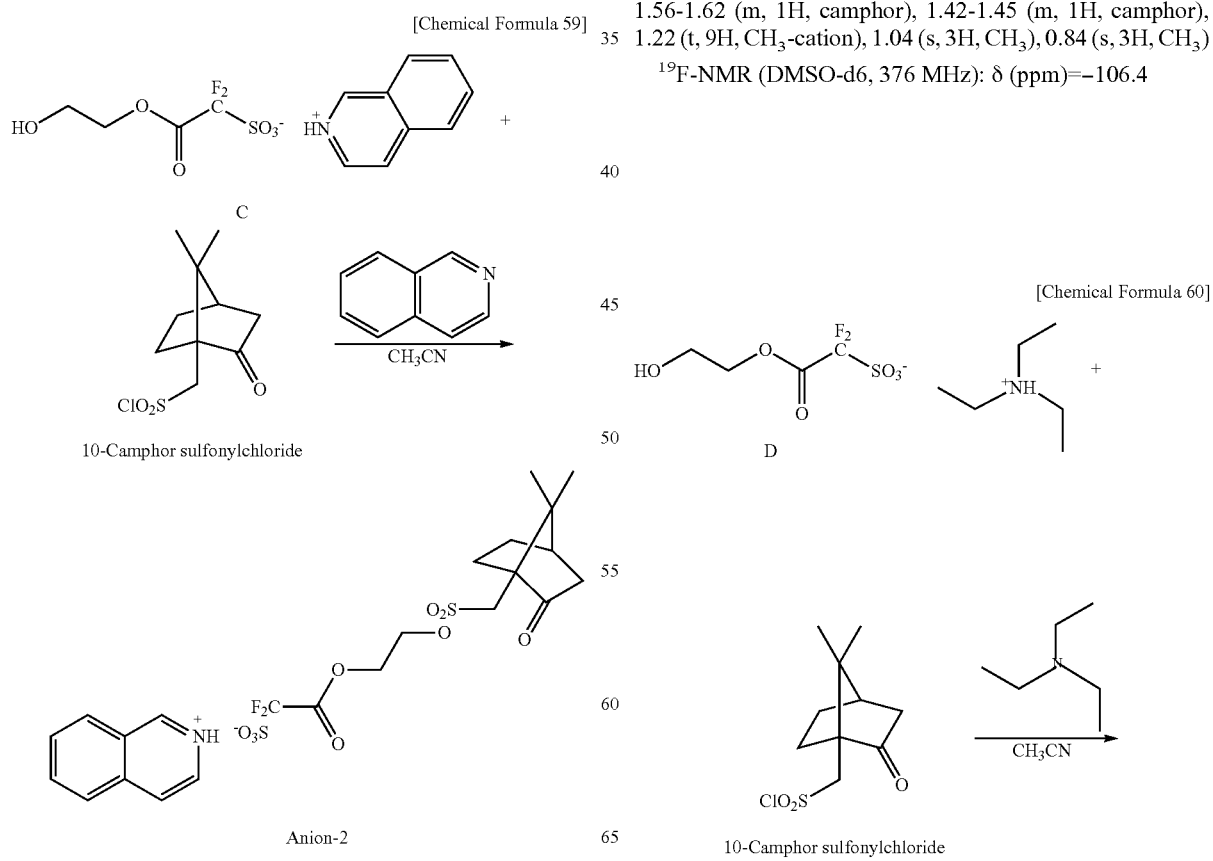

-continued

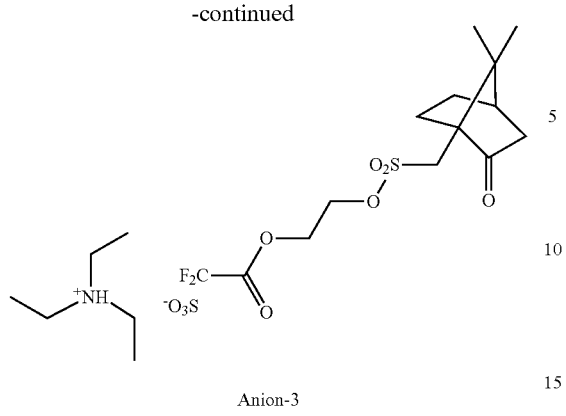

Anion-3

Synthesis Example 2-1

Compound: Synthesis of PAG-1

2.1 g of a compound represented by chemical formula B shown below, 2.6 g of the aforementioned Anion-1, 25 g of dichloromethane and 18 g of pure water were added into an eggplant-shaped flask, and the mixture was stirred at room temperature for 3 hours. Thereafter, the resulting organic phase (dichloromethane phase) was washed with 18 g of 1% hydrochloric acid water, and then washed repeatedly with 18 g of pure water until the organic phase became neutral. Then, the resulting organic phase was concentrated under reduced pressure, thereby obtaining 3.4 g of an objective compound (PAG-1) in the form of a white solid.

The obtained compound was analyzed by NMR, and the structure thereof was identified based on the results shown below.

$^1$H-NMR (DMSO-d6, 400 MHz): δ (ppm)=7.75-7.89 (m, 12H, ArH), 7.62 (d, 2H, ArH), 4.50-4.54 (m, 4H, OCH$_2$CH$_2$O), 3.57 (d, 1H, CH$_2$SO$_2$), 3.36 (m, 4H, CH$_2$SO$_2$, +cation-CH$_3$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR. (DMSO-d6, 376 MHz): δ (ppm)=−106.5

[Chemical Formula 61]

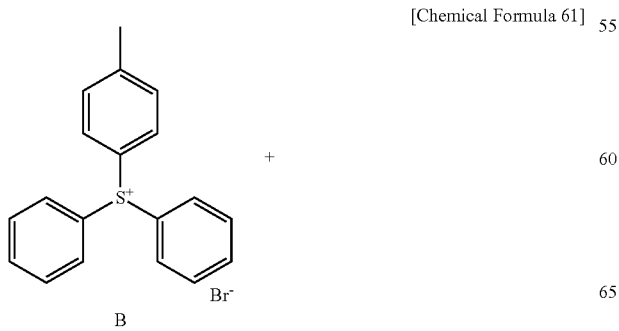

B

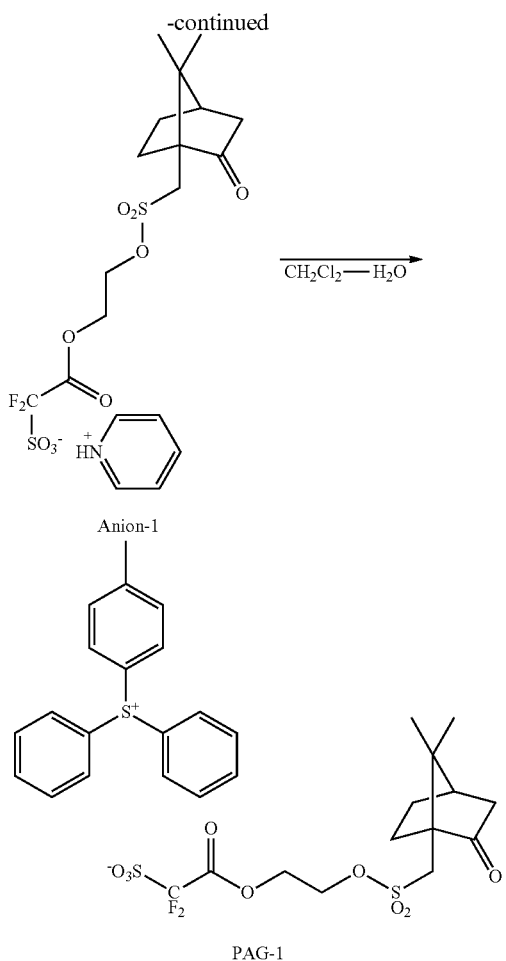

PAG-1

Synthesis Example 2-2

Compound: Synthesis of PAG-2

11.63 g of a compound represented by chemical formula E shown below, 10.3 g of the aforementioned Anion-1, 179.0 g of dichloromethane and 89.5 g of pure water were added into an eggplant-shaped flask, and the mixture was stirred at room temperature for 3 hours. Thereafter, the resulting organic phase (dichloromethane phase) was washed with 89.5 g of 1% hydrochloric acid water, and then washed repeatedly with 89.5 g of pure water until the organic phase became neutral. Then, the resulting organic phase was concentrated under reduced pressure, thereby obtaining 16.3 g of an objective compound (PAG-3) in the form of a white solid. The compound represented by chemical formula E shown below was synthesized in accordance with Japanese Unexamined Patent Application, First Publication No. 2009-019028.

The obtained compound was analyzed by NMR, and the structure thereof was identified based on the results shown below.

$^1$H-NMR (DMSO-d6, 400 MHz): δ (ppm)=7.77-7.89 (m, 10H, ArH), 7.64 (s, 2H, ArH), 4.61 (s, 2H, CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.28-2.38 (m, 8H, Cation–CH$_3$+camphor), 1.92-2.09 (m, 7H, Cation–ethylcyclopentyl+camphor), 1.57-1.69 (m, 7H, Cation–ethylcyclopentyl+camphor), 1.42-1.45 (m, 1H, camphor), 1.04 (s, 3H, camphor–CH$_3$), 0.83-0.86 (m, 6H, Cation–ethylcyclopentyl+camphor —CH$_3$)

$^{19}$F-NMR (DMSO-d6, 376 MHz): δ (ppm)=−106.4

Synthesis Example 2-3

Compound: Synthesis of PAG-3

The same operations as those described in the aforementioned Synthesis Example 2-2 were carried out with the exception that a bromine salt represented in chemical formula shown below was used instead of the compound represented by chemical formula E, thereby obtaining an objective compound (PAG-3).

The obtained compound was analyzed by NMR, and the structure thereof was identified based on the results shown below.

$^1$H-NMR (DMSO-d6, 400 MHz): δ (ppm)=7.74-7.90 (m, 15H, Phenyl), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 62]

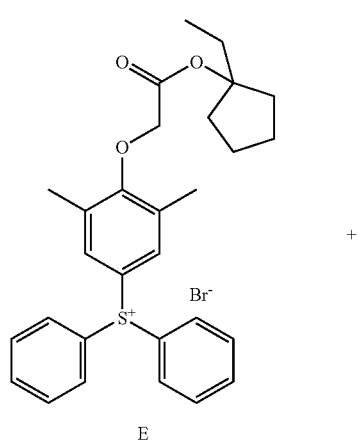

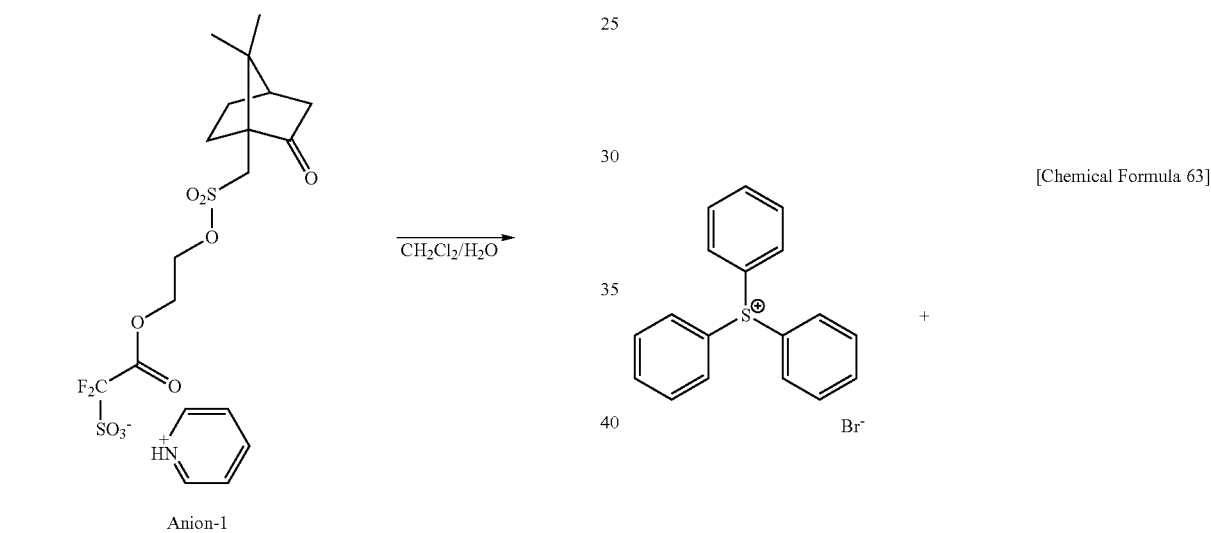

[Chemical Formula 63]

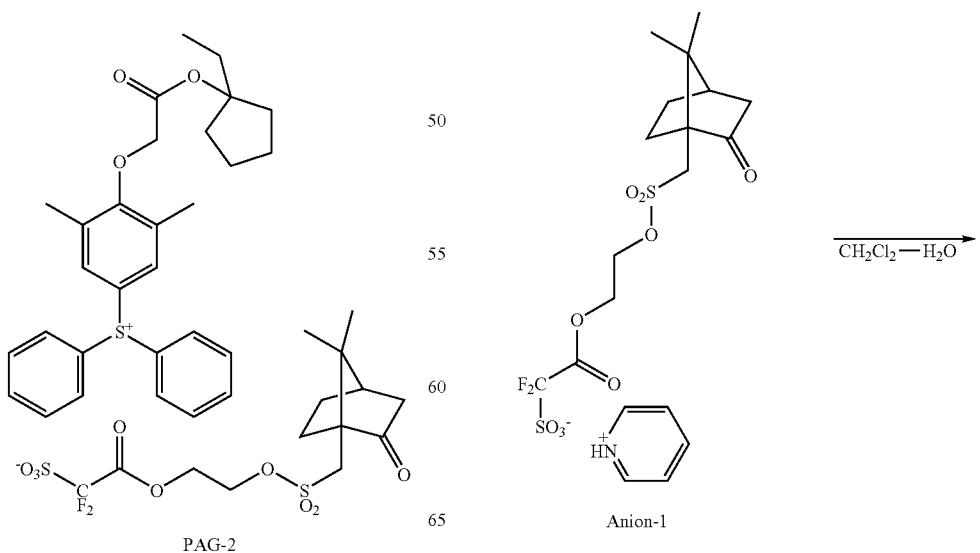

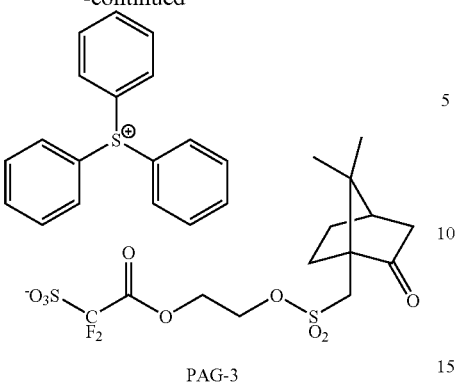

PAG-3

Synthesis Example 2-4

Compound: Synthesis of PAG-4

The same operations as those described in the aforementioned Synthesis. Example 2-2 were carried out with the exception that a bromine salt represented in chemical formula shown below was used instead of the compound represented by chemical formula E, thereby obtaining an objective compound (PAG-4).

The obtained compound was analyzed by NMR, and the structure thereof was identified based on the results shown below.

$^1$H-NMR (DMSO-d6, 400 MHz): δ (ppm)=8.50 (d, 2H, ArH), 8.37 (d, 2H, ArH), 7.93 (t, 2H, ArH), 7.55-7.75 (m, 7H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 64]

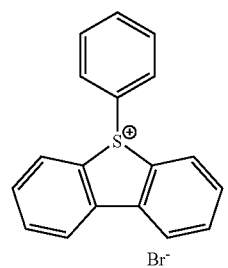

+

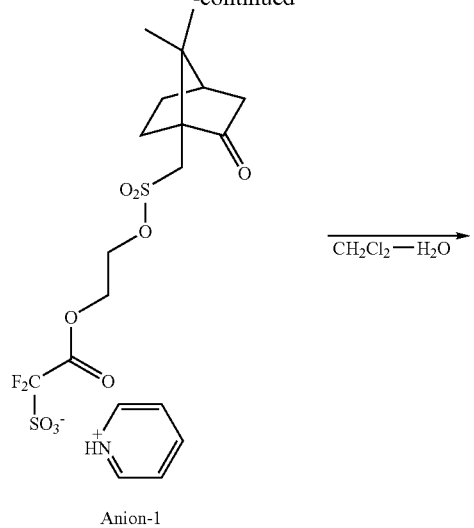

Anion-1

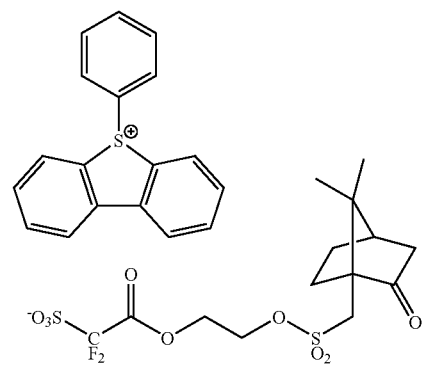

PAG-4

Synthesis Example 2-5

Compound: Synthesis of PAG-5

The same operations as those described in the aforementioned Synthesis Example 2-2 were carried out with the exception that a bromine salt represented in chemical formula shown below was used instead of the compound represented by chemical formula E, thereby obtaining an objective compound (PAG-5). The bromine salt represented in chemical formula shown below was synthesized in accordance with Japanese Unexamined Patent Application, First Publication No. 2009-019028.

The obtained compound was analyzed by NMR, and the structure thereof was identified based on the results shown below.

$^1$H-NMR (DMSO-d6, 400 MHz): δ (ppm)=7.75-7.86 (m, 10H, ArH), 7.61 (s, 2H, ArH), 4.62 (s, 2H, CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 8H, camphor+Cation−CH$_3$), 2.07 (t, 1H, camphor), 1.49-1.99 (m, 20H, camphor+Adamantane), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 65]

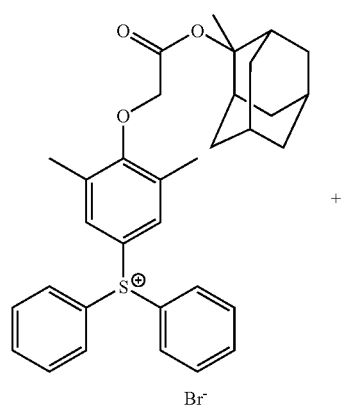

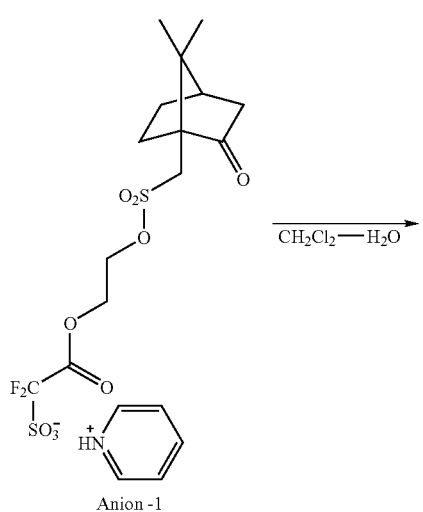

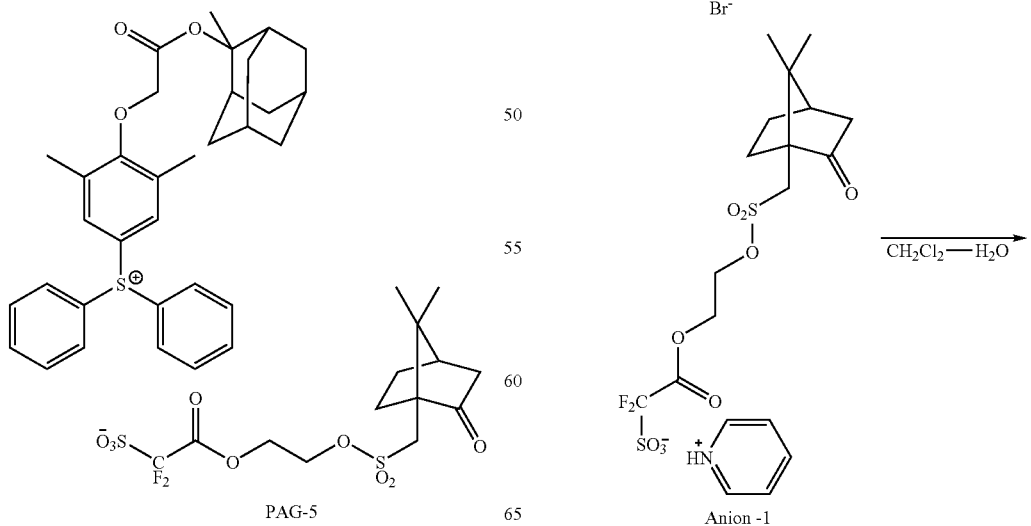

Synthesis Example 2-6

Compound: Synthesis of PAG-6

The same operations as those described in the aforementioned Synthesis Example 2-2 were carried out with the exception that a bromine salt represented in chemical formula shown below was used instead of the compound represented by chemical formula E, thereby obtaining an objective compound (PAG-6). The bromine salt represented in chemical formula shown below was synthesized in accordance with Japanese Unexamined Patent Application, First Publication No. 2009-019028.

The obtained compound was analyzed by NMR, and the structure thereof was identified based on the results shown below.

$^1$H-NMR. (DMSO-d6, 400 MHz): δ (ppm)=7.76-7.82 (m, 10H, ArH), 7.59 (s, 2H, ArH), 4.55 (s, 2H, CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 8H, camphor+Cation–CH$_3$), 2.07 (t, 1H, camphor), 1.90-2.06 (m, 4H, camphor+Cation–cyclopentyl), 1.48-1.75 (m, 10H, camphor+cyclopentyl), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 66]

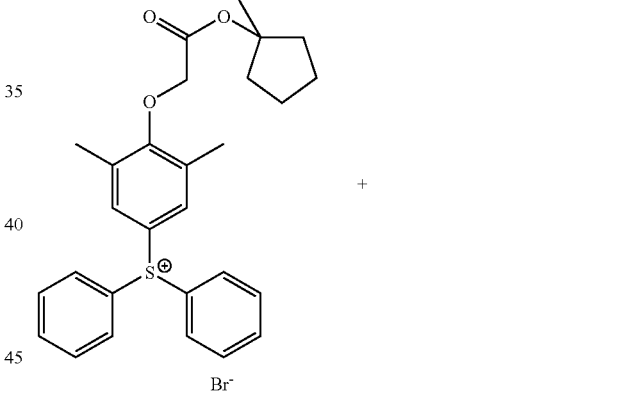

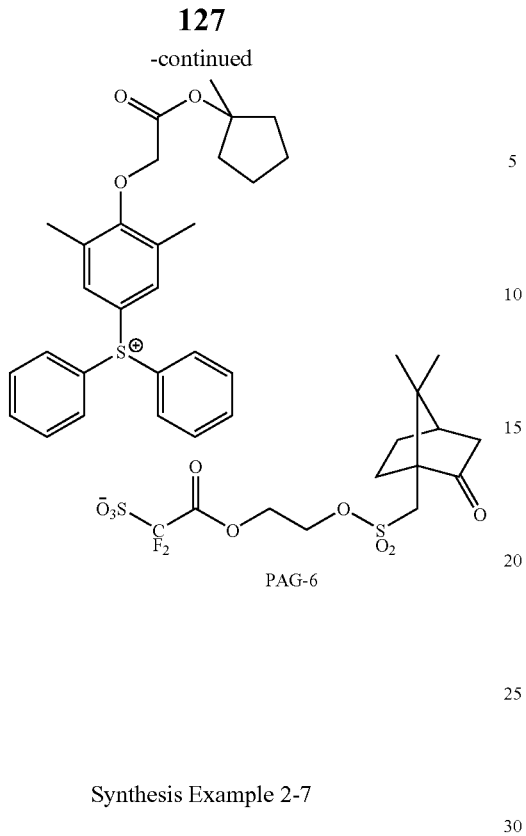

PAG-6

Synthesis Example 2-7

Compound: Synthesis of PAG-7

The same operations as those described in the aforementioned Synthesis Example 2-2 were carried out with the exception that a methane sulfonic acid salt represented in chemical formula shown below was used instead of the compound represented by chemical formula E, thereby obtaining an objective compound (PAG-7).

The obtained compound was analyzed by NMR, and the structure thereof was identified based on the results shown below.

$^1$H-NMR (DMSO-d6, 400 MHz): δ (ppm)=10.05 (s, 1H, OH), 7.64-7.87 (m, 10H, ArH), 7.56 (s, 2H, ArH), 4.50=4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.22 (m, 6H, CH$_3$), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 67]

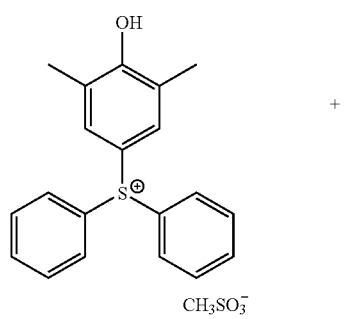

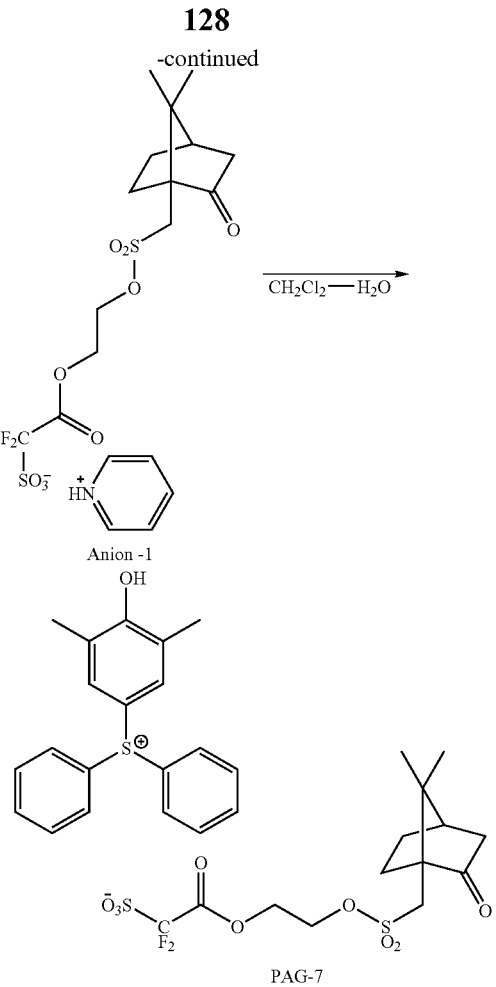

PAG-7

Synthesis Example 2-8

Compound: Synthesis of PAG-8

The same operations as those described in the aforementioned Synthesis Example 2-2 were carried out with the exception that a bromine salt represented in chemical formula shown below was used instead of the compound represented by chemical formula E, thereby obtaining an objective compound (PAG-8). The bromine salt represented in chemical formula shown below was synthesized by deprotecting a protecting group (i.e., a 2-methyl-2-adamantyl group) of a compound (b1-14-503) in Example 7 disclosed in Japanese Unexamined Patent Application, First Publication No. 2009-019028.

The obtained compound was analyzed by NMR, and the structure thereof was identified based on the results shown below.

$^1$H-NMR (DMSO-d6, 400 MHz): δ (ppm)=7.71-7.89 (m, 10H, ArH), 7.59 (s, 2H, ArH), 4.50-4.54 (m, 6H, cation−CH$_2$+OCH$_2$CH$_2$O), 3.57 (d, 1H, CH$_2$SO$_2$), 3.36 (s, 1H, CH$_2$SO$_2$), 3.30 (brs, 1H, OH), 2.24-2.34 (m, 8H, cation−CH$_3$+camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

Synthesis Example 2-9

Compound: Synthesis of PAG-9

The same operations as those described in the aforementioned Synthesis Example 2-2 were carried out with the exception that a bromine salt represented in chemical formula shown below was used instead of the compound represented by chemical formula E, thereby obtaining an objective compound (PAG-9). The bromine salt represented in chemical formula shown below was synthesized in accordance with Japanese Unexamined Patent Application, First Publication No. Hei 8-157451.

The obtained compound was analyzed by NMR, and the structure thereof was identified based on the results shown below.

$^1$H-NMR (DMSO-d6, 400 MHz): δ (ppm)=7.75-7.86 (m, 10H, ArH), 7.63 (s, 2H, ArH), 4.55 (s, 2H, CO—CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 8H, camphor+Cation–CH$_3$), 2.07 (t, 1H, camphor), 1.92-1.99 (m, 2H, camphor), 1.56-1.62 (m, 1H, camphor), 1.42-1.45 (m, 10H, camphor+t-Butyl), 1.04 (s, 3H, CH$_3$), 0.84 (s, 3H, CH$_3$)

$^{19}$F-NMR (DMSO-d6, 376 MHz): δ (ppm)=−106.5

[Chemical Formula 68]

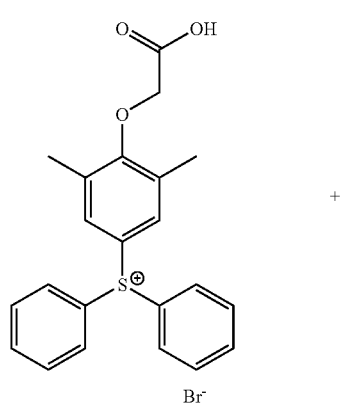

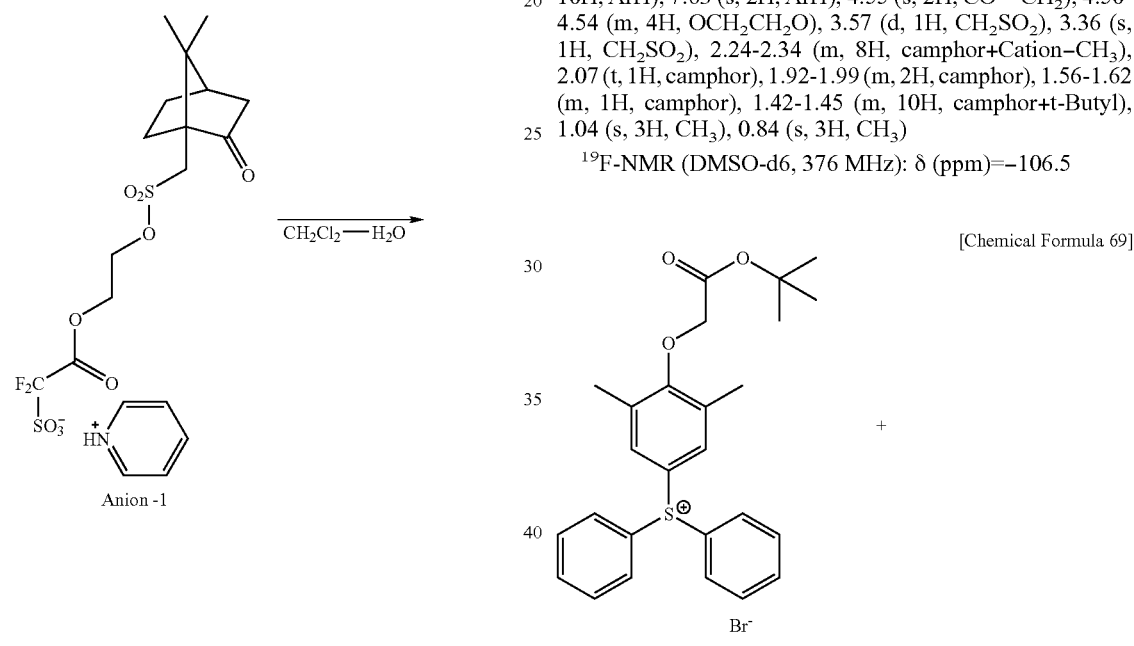

[Chemical Formula 69]

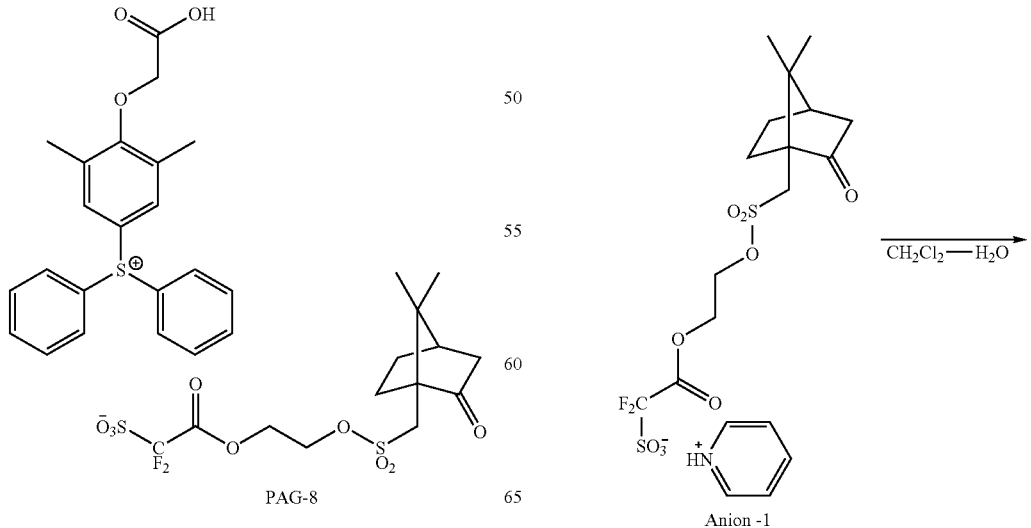

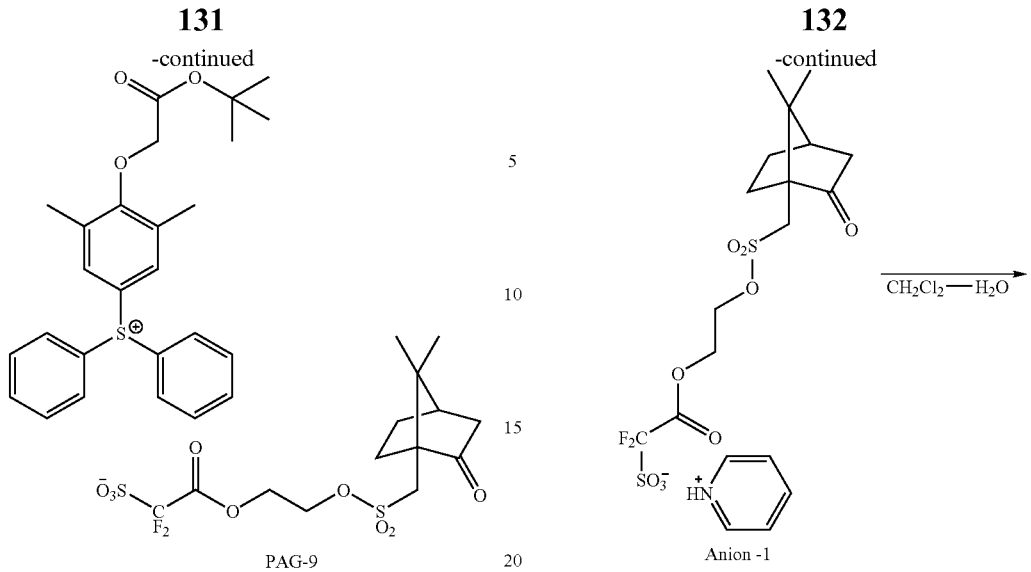

PAG-9

Synthesis Example 2-10

Compound: Synthesis of PAG-10

The same operations as those described in the aforementioned Synthesis Example 2-2 were carried out with the exception that a bromine salt represented in chemical formula shown below was used instead of the compound represented by chemical formula E, thereby obtaining an objective compound (PAG-10).

The obtained compound was analyzed by NMR, and the structure thereof was identified based on the results shown below.

$^1$H-NMR. (DMSO-d6, 400 MHz): δ (ppm)=7.75-7.87 (m, 10H, ArH), 7.63 (s, 2H, ArH), 4.94 (t, 2H, OCH$_2$CF$_2$), 4.84 (s, 2H, OCH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.37 (s, 6H, cation–CH$_3$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−80.4, −106.5, −119.7

[Chemical Formula 70]

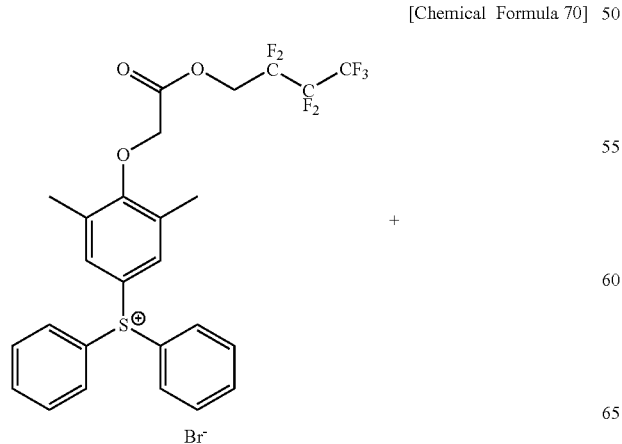

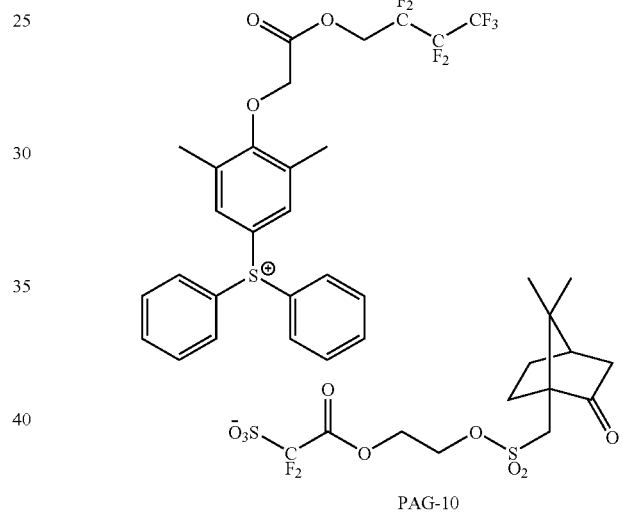

PAG-10

The bromine salt used in Synthesis Example 2-10 was synthesized by the following procedures.

5.00 g of a compound (10a) shown below and 50.0 g of dichloromethane were added to a three-necked flask under a nitrogen atmosphere to completely dissolve the compound, and the resulting solution was cooled to 5° C. or less. 0.28 g of N,N-dimethylaminopyridine (DMAP) was then added thereto, followed by stirring at 10° C. or less for 5 minutes, and 5.46 g of 1-ethyl-3-(3-dimethylaminopropyl)carbodiimide hydrochloride was then gradually added thereto. After stirring the resulting mixture for 10 minutes, 1.37 g of 1H,1H-pentafluoropropanol was gradually dropwise added thereto. After completion of the addition, the temperature was raised to room temperature, and the resulting mixture was stirred at room temperature for 30 hours. After completion of the reaction, the dichloromethane phase obtained by liquid separation was washed with diluted hydrochloric acid, and then washed repeatedly with pure water until the dichloromethane phase became neutral. Thereafter, dichloromethane was distilled off under reduced pressure, and the resulting viscous solid was dried, thereby obtaining 3.72 g of an objective bromine salt.

[Chemical Formula 71]

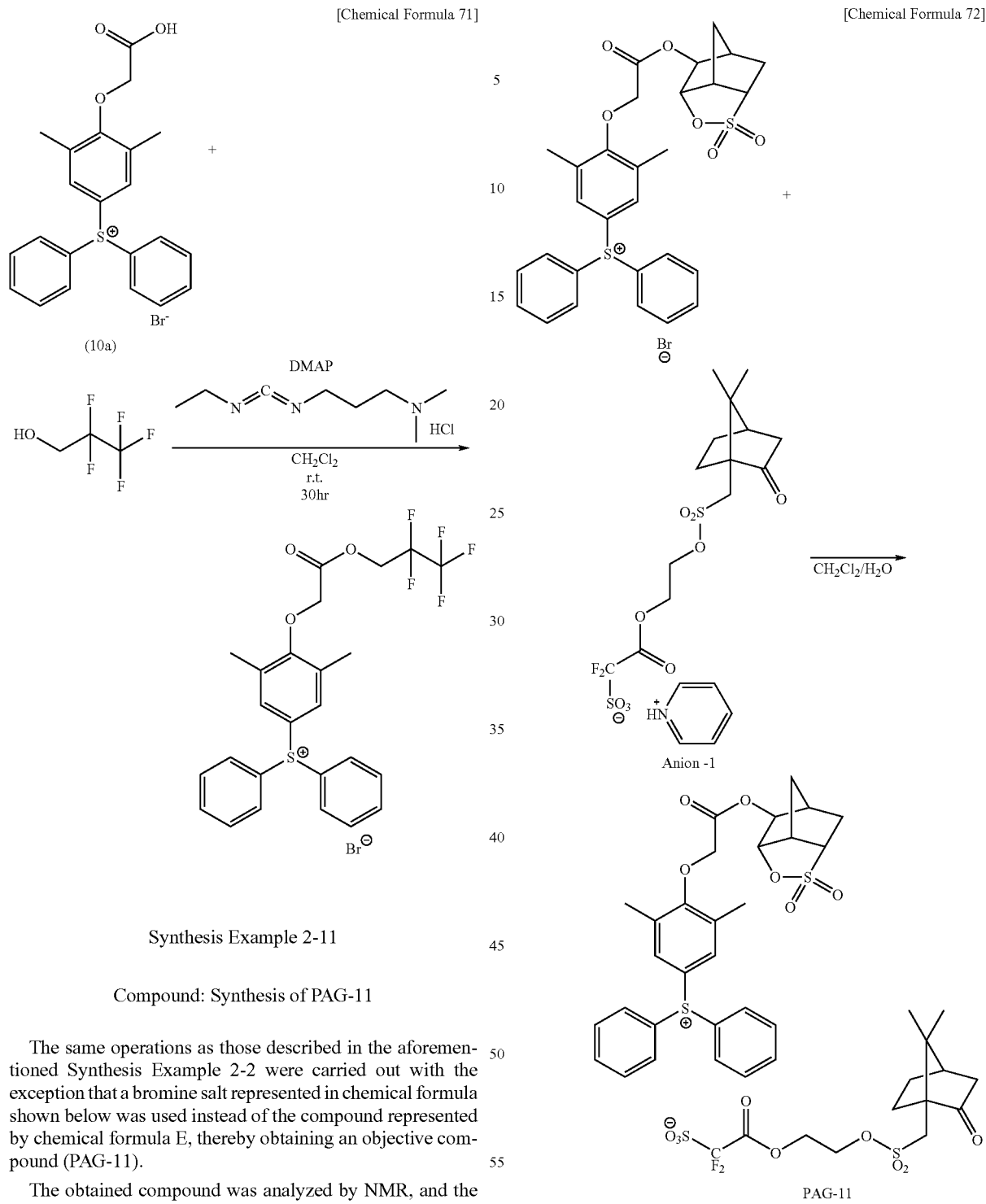

Synthesis Example 2-11

Compound: Synthesis of PAG-11

The same operations as those described in the aforementioned Synthesis Example 2-2 were carried out with the exception that a bromine salt represented in chemical formula shown below was used instead of the compound represented by chemical formula E, thereby obtaining an objective compound (PAG-11).

The obtained compound was analyzed by NMR, and the structure thereof was identified based on the results shown below.

$^1$H-NMR (DMSO-d6, 400 MHz): δ (ppm)=7.72-7.83 (m, 10H, ArH), 7.59 (s, 2H, ArH), 4.90 (m, 1H, sultone), 4.62-4.68 (m, 3H, CH$_2$, sultone), 4.50-4.54 (m, 4H, OCH$_2$CH$_2$O), 3.83-3.89 (m, 1H, sultone), 3.57 (d, 1H, CH$_2$SO$_2$), 3.43 (m, 1H, sultone), 3.36 (s, 1H, CH$_2$SO$_2$), 1.75-2.49 (m, 16H, camphor+sultone), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

The bromine salt used in Synthesis Example 2-11 was synthesized by the following procedures.

10 g of a compound (11a) shown below and 100 g of dichloromethane were added to a three-necked flask under a nitrogen atmosphere, and the resulting mixture was cooled to 5° C. or less. 0.56 g of N,N-dimethylaminopyridine (DMAP) was then added thereto, followed by stirring at 5° C. or less for 5 minutes. Then, 4.8 g of 1-ethyl-3-(3-dimethylaminopropyl) carbodiimide hydrochloride was added thereto. Thereafter, the resulting mixture was stirred for 10 minutes, and 3.5 g of a compound (11b) was then added thereto. After completion of the addition, the temperature was raised to room temperature, and the resulting mixture was stirred at room temperature for 15 hours. Then, the resultant was washed with diluted hydrochloric acid, and then washed repeatedly with pure water. The resulting organic phase was then dropwise added to 1,100 g of n-hexane to reprecipitate, thereby obtaining 10.9 g of an objective bromine salt.

norbornane), 4.50-4.54 (m, 4H, OCH$_2$CH$_2$O), 3.57 (d, 1H, CH$_2$SO$_2$), 3.36 (s, 1H, CH$_2$SO$_2$), 2.69-2.73 (m, 1H, oxo-norbornane), 2.20-2.41 (m, 8H, camphor+cation–CH$_3$), 2.06-2.16 (m, 3H, camphor+oxo-norbornane), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

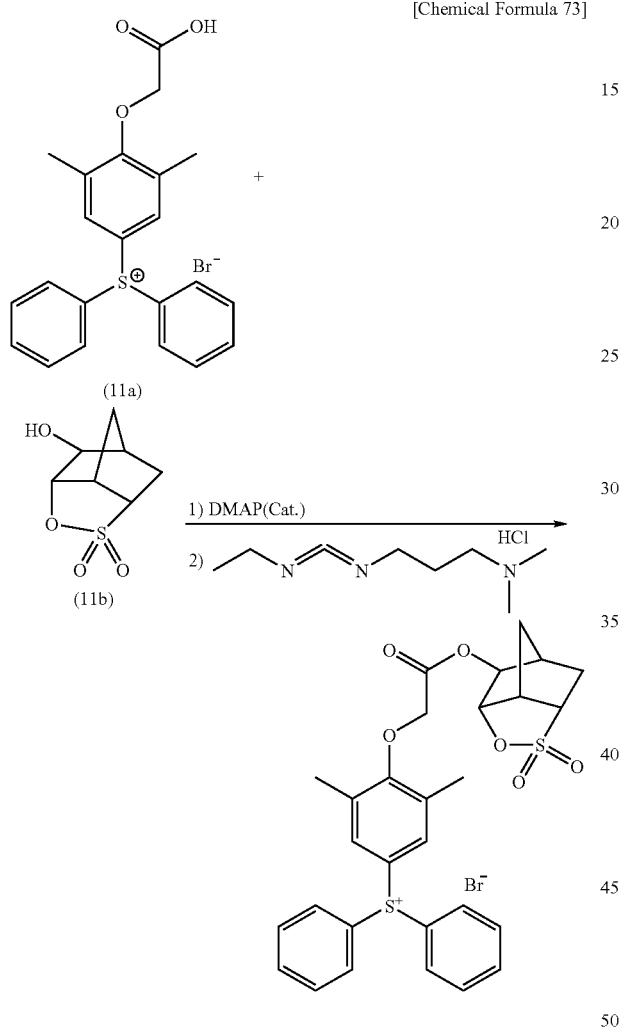

[Chemical Formula 73]

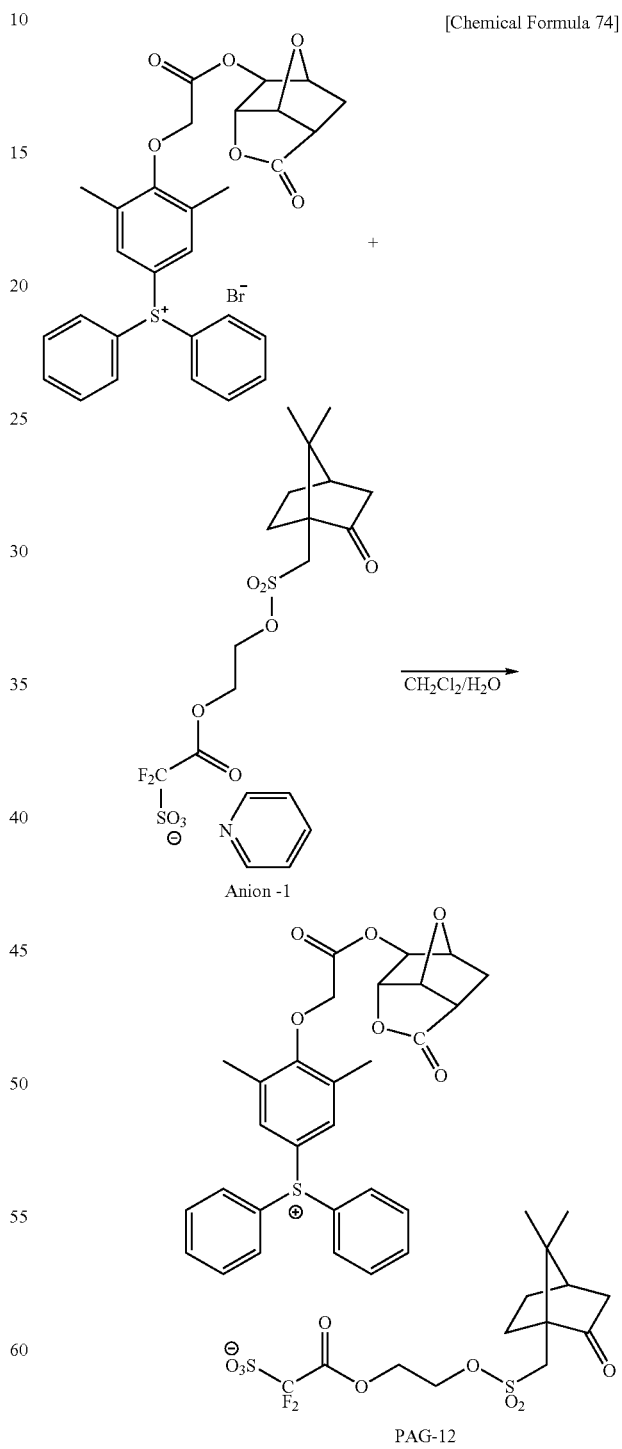

[Chemical Formula 74]

Synthesis Example 2-12

Compound: Synthesis of PAG-12

The same operations as those described in the aforementioned Synthesis Example 2-2 were carried out with the exception that a bromine salt represented in chemical formula shown below was used instead of the compound represented by chemical formula E, thereby obtaining an objective compound (PAG-12).

The obtained compound was analyzed by NMR, and the structure thereof was identified based on the results shown below.

$^1$H-NMR (DMSO-d6, 400 MHz): δ (ppm)=7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH$_2$+oxo- The bromine salt used in Synthesis Example 2-12 was synthesized by the following procedures.

15 g of a compound (12a) and 150 g of dichloromethane were added to a three-necked flask under a nitrogen atmosphere, and the resulting mixture was cooled to 5° C. or less. 0.84 g of N,N-dimethylaminopyridine (DMAP) was then added thereto, followed by stirring at 5° C. or less for 5 minutes. Then, 7.2 g of 1-ethyl-3-(3-dimethylaminopropyl) carbodiimide hydrochloride was added thereto. Thereafter, the resulting mixture was stirred for 10 minutes, and 4.3 g of a compound (12b) was then added thereto. After completion of the addition, the temperature was raised to room temperature, and the resulting mixture was stirred at room temperature for 15 hours. Then, the resultant was washed with diluted hydrochloric acid, and then washed repeatedly with pure water. The resulting organic phase was then dropwise added to 1,100 g of n-hexane to reprecipitate, thereby obtaining 10.1 g of an objective bromine salt.

The obtained compound was analyzed by NMR, and the structure thereof was identified based on the results shown below.

$^1$H-NMR (DMSO-d6, 400 MHz): δ (ppm)=7.73-7.85 (m, 10H, ArH), 7.59 (s, 2H, ArH), 4.50-4.54 (m, 4H, OCH$_2$CH$_2$O), 3.83 (t, 2H, CH$_2$), 3.57 (d, 1H, CH$_2$SO$_2$), 3.36 (s, 1H, CH$_2$SO$_2$), 2.24-2.34 (m, 8H, camphor+cation–CH$_3$), 2.07 (t, 1H, camphor), 1.92-1.99 (m, 2H, camphor), 1.56-1.62 (m, 1H, camphor), 1.42-1.45 (m, 5H, camphor+cation–CH$_2$), 1.29 (m, 4H, cation–CH$_2$), 1.04 (s, 3H, CH$_3$), 0.87 (t, 3H, CH$_3$) 0.84 (s, 3H, CH$_3$)

$^{19}$F-NMR (DMSO-d6, 376 MHz): δ (ppm)=−106.5

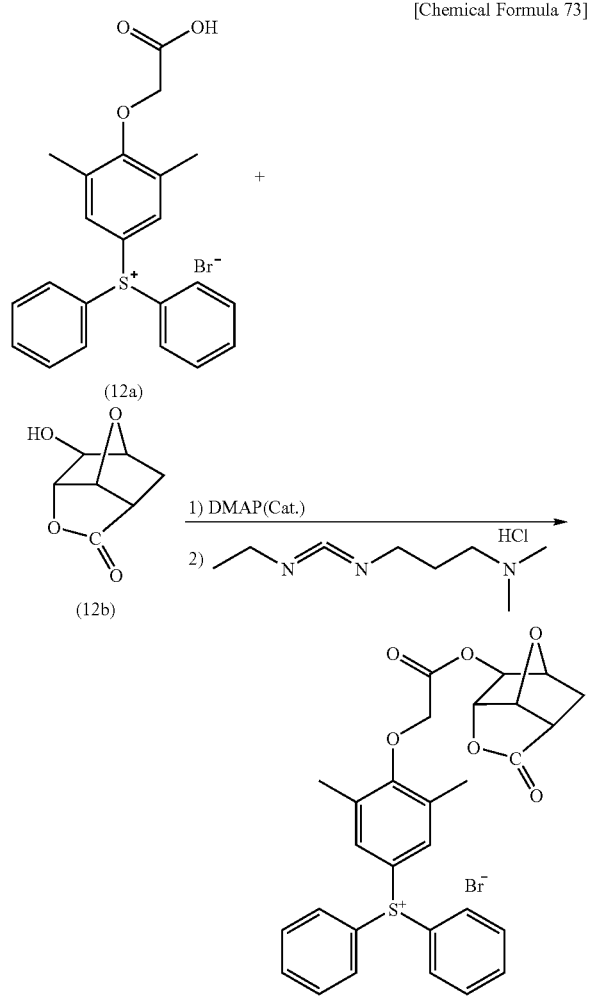

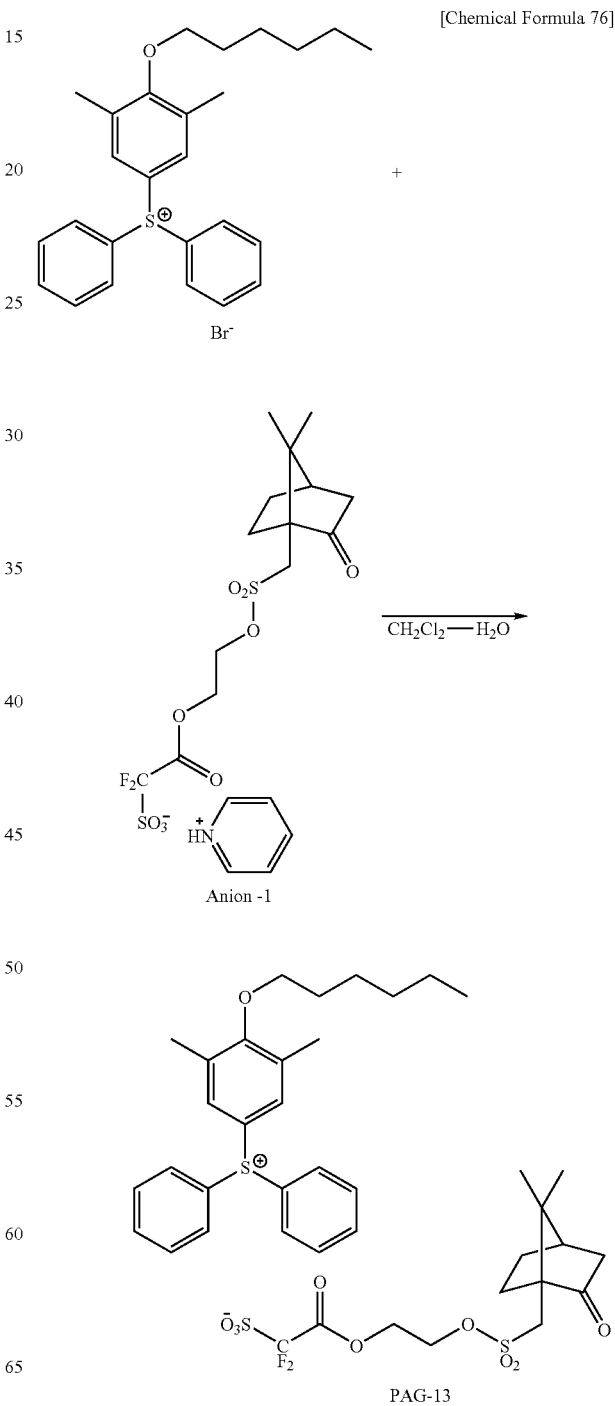

Synthesis Example 2-13

Compound: Synthesis of PAG-13

The same operations as those described in the aforementioned Synthesis Example 2-2 were carried out with the exception that a bromine salt represented in chemical formula shown below was used instead of the compound represented by chemical formula E, thereby obtaining an objective compound (PAG-13).

Synthesis Example 2-14

Compound: Synthesis of PAG-14

The same operations as those described in the aforementioned Synthesis Example 2-2 were carried out with the exception that a bromine salt represented in chemical formula shown below was used instead of the compound represented by chemical formula E, thereby obtaining an objective compound (PAG-14).

The obtained compound was analyzed by NMR, and the structure thereof was identified based on the results shown below.

$^1$H-NMR (DMSO-d6, 400 MHz): δ (ppm)=8.53 (d, 2H, ArH), 8.27 (d, 2H, ArH), 7.95 (t, 2H, ArH), 7.74 (t, 2H, ArH), 7.20 (s, 1H, ArH), 6.38 (s, 1H, ArH), 4.50-4.54 (m, 4H, OCH$_2$CH$_2$O), 4.05 (t, 2H, cation —OCH$_2$), 3.57 (d, 1H, CH$_2$SO$_2$), 3.36 (s, 1H, CH$_2$SO$_2$), 2.86 (s, 3H, ArCH$_3$), 2.24-2.34 (m, 2H, camphor), 2.07 (t, 1H, camphor), 1.92-1.99 (m, 2H, camphor), 1.84 (s, 3H, ArCH$_3$), 1.69 (quin, 2H, cation–CH$_2$), 1.56-1.62 (m, 1H, camphor), 1.42-1.45 (m, 1H, camphor), 1.37 (quin, 2H, cation–CH$_2$), 1.24-1.26 (m, 4H, cation–CH$_2$), 1.04 (s, 3H, CH$_3$), 0.84 (s, 3H, CH$_3$), 0.82 (t, 3H, cation–CH$_3$)

$^{19}$F-NMR (DMSO-d6, 376 MHz): δ (ppm)=−106.5

[Chemical Formula 77]

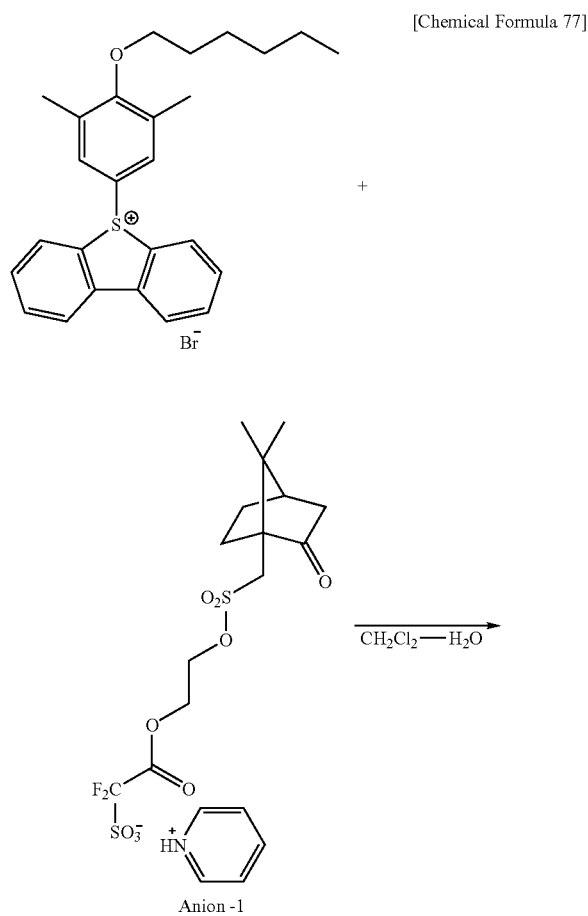

Anion -1

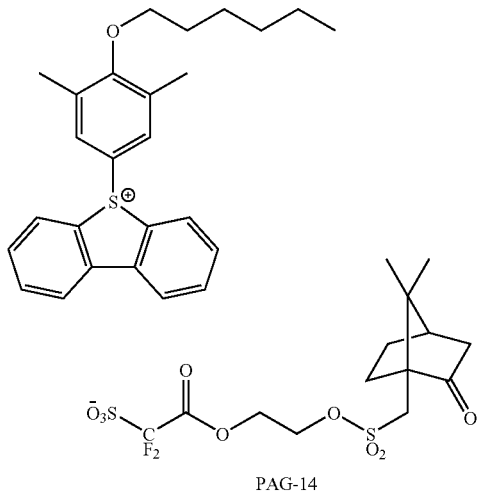

PAG-14

Synthesis Example 2-15

Compound: Synthesis of PAG-15

The same operations as those described in the aforementioned Synthesis Example 2-2 were carried out with the exception that a bromine salt represented in chemical formula shown below was used instead of the compound represented by chemical formula E, thereby obtaining an objective compound (PAG-15).

The obtained compound was analyzed by NMR, and the structure thereof was identified based on the results shown below.

$^1$H-NMR (DMSO-d6, 400 MHz): δ (ppm)=7.99-8.01 (d, 2H, Ar), 7.73-7.76 (t, 1H, Ar), 7.58-7.61 (t, 2H, Ar), 5.31 (s, 2H, SCH$_2$C=O), 4.50-4.54 (m, 4H, OCH$_2$CH$_2$O), 3.49-3.62 (m, 5H, cation–CH$_2$+CH$_2$SO$_2$), 3.36 (s, 1H, CH$_2$SO$_2$), 2.18-2.49 (m, 6H, camphor+cation–CH$_2$S), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR. (DMSO-d6, 376 MHz): δ (ppm)=−106.5

[Chemical Formula 78]

[Chemical Formula 79]

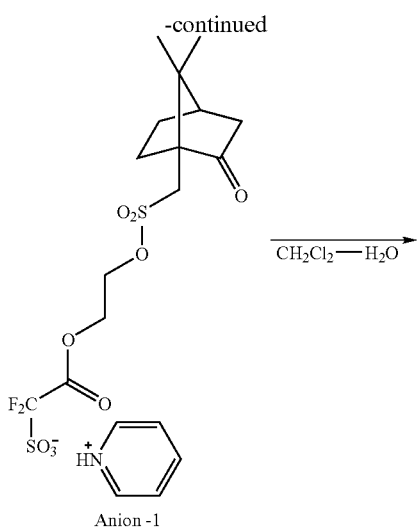

Anion -1

PAG-15

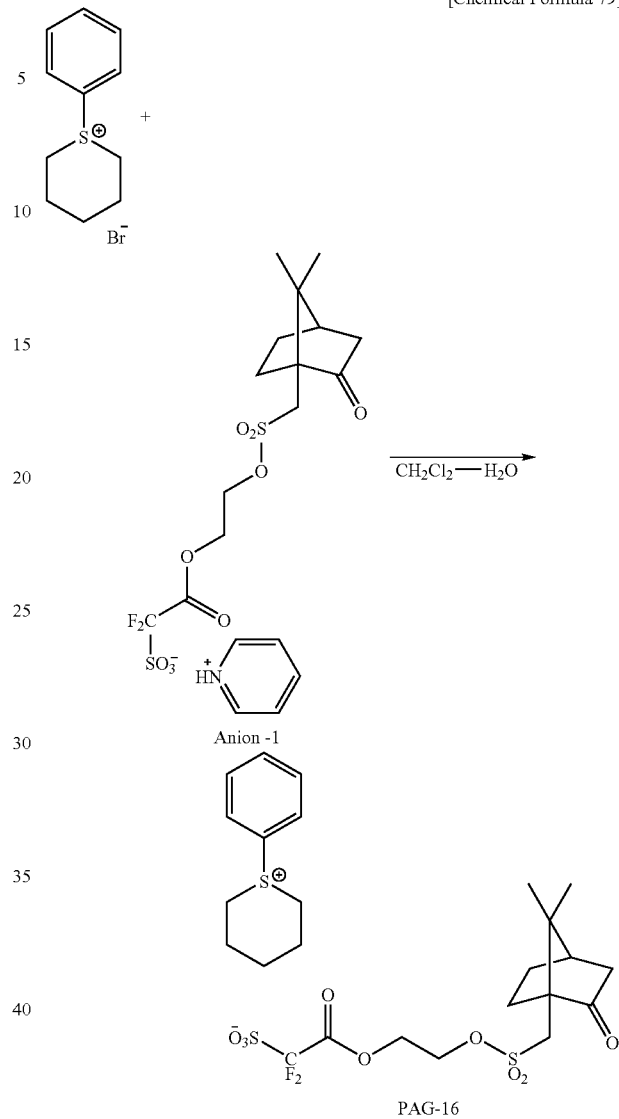

Anion -1

PAG-16

Synthesis Example 2-16

Compound: Synthesis of PAG-16

The same operations as those described in the aforementioned Synthesis Example 2-2 were carried out with the exception that a bromine salt represented in chemical formula shown below was used instead of the compound represented by chemical formula E, thereby obtaining an objective compound (PAG-16).

The obtained compound was analyzed by NMR, and the structure thereof was identified based on the results shown below.

$^1$H-NMR (DMSO-d6, 400 MHz): δ (ppm)=8.02-8.05 (m, 2H, Phenyl), 7.61-7.73 (m, 3H, Phenyl), 4.50-4.54 (m, 4H, OCH$_2$CH$_2$O), 3.76-3.86 (m, 4H, cation —SCH$_2$), 3.57 (d, 1H, CH$_2$SO$_2$), 3.36 (s, 1H, CH$_2$SO$_2$), 2.24-2.34 (m, 2H, camphor), 2.09-2.12 (m, 2H, cation–CH$_2$), 2.07 (t, 1H, camphor), 1.94-1.99 (m, 2H, camphor), 1.84-1.93 (m, 2H, cation–CH$_2$), 1.63-1.70 (m, 2H, cation–CH$_2$), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

Synthesis Example 2-17

Compound: Synthesis of PAG-17

The same operations as those described in the aforementioned Synthesis Example 2-2 were carried out with the exception that a bromine salt represented in chemical formula shown below was used instead of the compound represented by chemical formula E, thereby obtaining an objective compound (PAG-17).

The obtained compound was analyzed by NMR, and the structure thereof was identified based on the results shown below.

$^1$H-NMR (DMSO-d6, 400 MHz): δ (ppm)=8.04-8.09 (m, 2H, Phenyl), 7.69-7.79 (m, 3H, Phenyl), 4.50-4.54 (m, 4H, OCH$_2$CH$_2$O), 3.57 (d, 1H, CH$_2$SO$_2$), 3.36 (s, 1H, CH$_2$SO$_2$), 3.29 (s, 6H, cation–CH$_3$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 80]

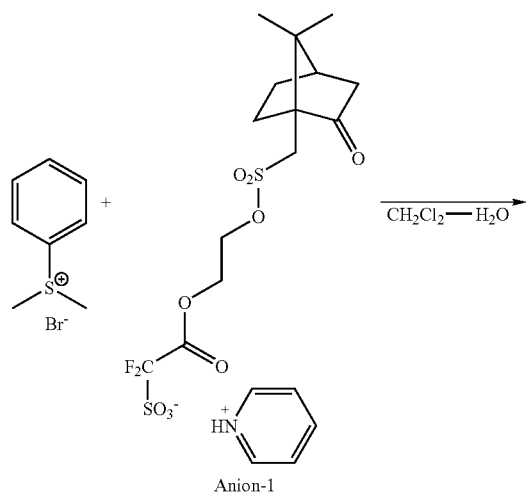

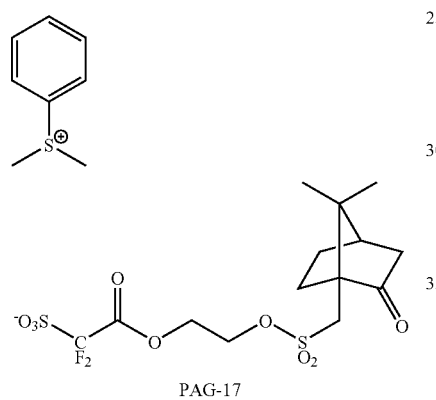

PAG-17

Synthesis Example 2-18

Compound: Synthesis of PAG-18

The same operations as those described in the aforementioned Synthesis Example 2-2 were carried out with the exception that a bromine salt represented in chemical formula shown below was used instead of the compound represented by chemical formula E, thereby obtaining an objective compound (PAG-18).

The obtained compound was analyzed by NMR, and the structure thereof was identified based on the results shown below.

$^1$H-NMR (DMSO-d6, 400 MHz): δ (ppm)=8.07 (d, 2H, Phenyl), 7.81 (d, 2H, Phenyl), 4.50-4.54 (m, 4H, OCH$_2$CH$_2$O), 4.10 (t, 2H, cation–CH$_2$), 3.59 (d, 2H, cation–CH$_2$), 3.57 (d, 1H, CH$_2$SO$_2$), 3.36 (s, 1H, CH$_2$SO$_2$), 2.24-2.34 (m, 2H, camphor), 2.20 (d, 2H, cation–CH$_2$), 1.71-2.19 (m, 7H, camphor+cation–CH$_2$), 1.56-1.62 (m, 1H, camphor), 1.42-1.45 (m, 1H, camphor), 1.23 (s, 9H, t-Bu), 1.04 (s, 3H, CH$_3$), 0.84 (s, 3H, CH$_3$)

$^{19}$F-NMR (DMSO-d6, 376 MHz): δ (ppm)=−106.5

[Chemical Formula 81]

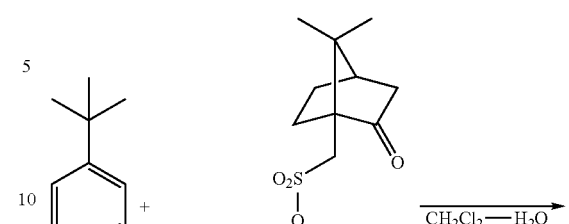

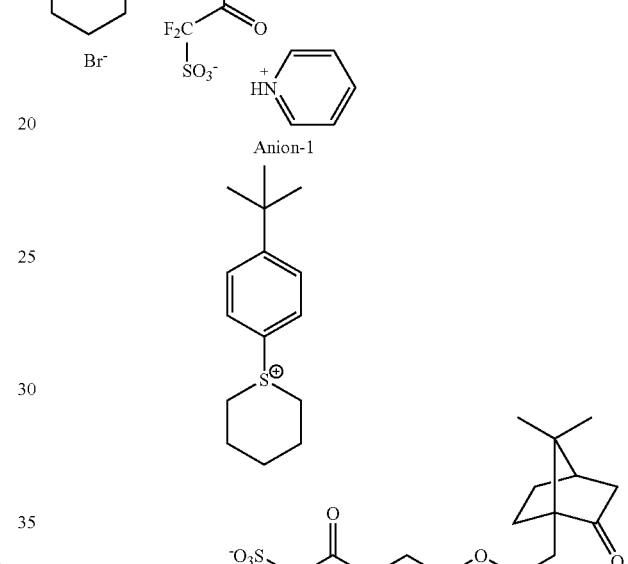

PAG-18

Synthesis Example 2-19

Compound: Synthesis of PAG-19

The same operations as those described in the aforementioned Synthesis Example 2-2 were carried out with the exception that a bromine salt represented in chemical formula shown below was used instead of the compound represented by chemical formula E, thereby obtaining an objective compound (PAG-19).

The obtained compound was analyzed by NMR, and the structure thereof was identified based on the results shown below.

$^1$H-NMR (DMSO-d6, 400 MHz): δ (ppm)=7.77-7.89 (m, 10H, ArH), 7.70 (s, 2H, ArH), 5.10 (s, 2H, OCOCH$_2$O), 4.50-4.54 (m, 411, OCH$_2$CH$_2$O), 3.57 (d, 1H, CH$_2$SO$_2$), 3.36 (s, 1H, CH$_2$SO$_2$), 2.24-2.34 (m, 2H, camphor), 2.08-2.19 (m, 9H, cation–CH$_3$), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 82]

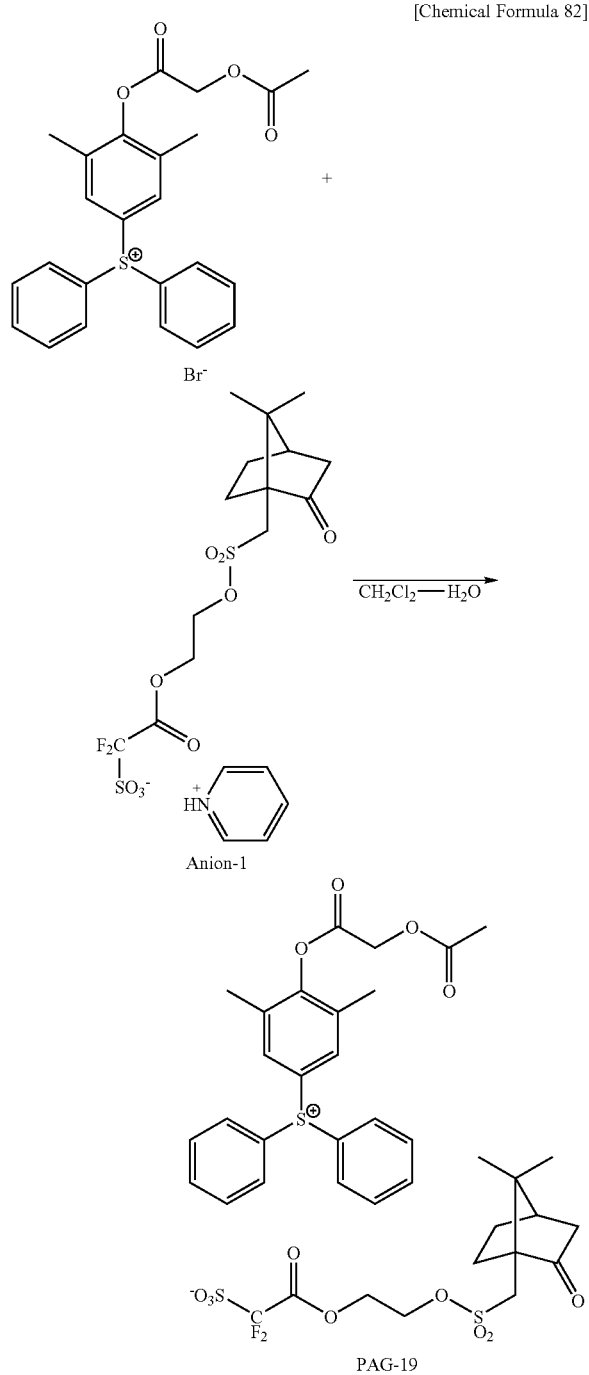

PAG-19

The bromine salt used in Synthesis Example 2-19 was synthesized by the following procedures.

3.82 g of a compound (19a) and 28.0 g of dichloromethane were added to a three-necked flask and stirred therein under a nitrogen atmosphere, and 1.31 g of triethylamine diluted with 4.00 g of dichloromethane was then dropwise added thereto. While holding the temperature of the reaction system at 10° C. or less, 1.63 g of acetoxyacetyl chloride diluted with 8.00 g of dichloromethane was dropwise added thereto over 15 minutes. Thereafter, a reaction was conducted at room temperature for 3 hours. After completion of the reaction, the dichloromethane phase was washed with diluted hydrochloric acid, and then with water. Thereafter, dichloromethane was distilled off under reduced pressure, and the resulting oily substance was dried, thereby obtaining 2.76 g of an objective bromine salt.

[Chemical Formula 83]

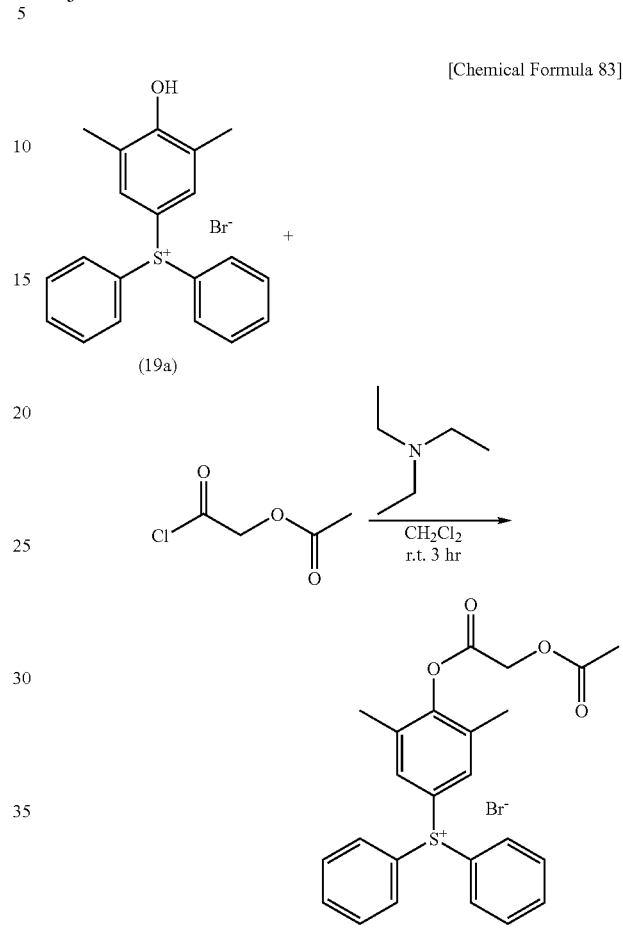

Synthesis Example 2-20

Compound: Synthesis of PAG-20

The same operations as those described in the aforementioned Synthesis Example 2-2 were carried out with the exception that a bromine salt represented in chemical formula shown below was used instead of the compound represented by chemical formula E, thereby obtaining an objective compound (PAG-20).

The obtained compound was analyzed by NMR, and the structure thereof was identified based on the results shown below.

$^1$H-NMR (DMSO-d6, 400 MHz): δ (ppm)=7.84 (d, 6H, ArH), 7.78 (d, 6H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.33 (s, 27H, tBu —CH$_3$), 1.04 (s, 3H, CH$_3$), 0.84 (s, 3H, CH$_3$)

$^{19}$F-NMR (DMSO-d6, 376 MHz): δ (ppm)=−106.5

[Chemical Formula 84]

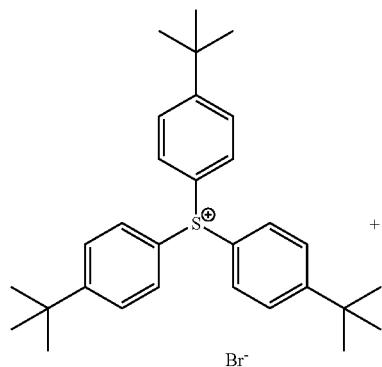

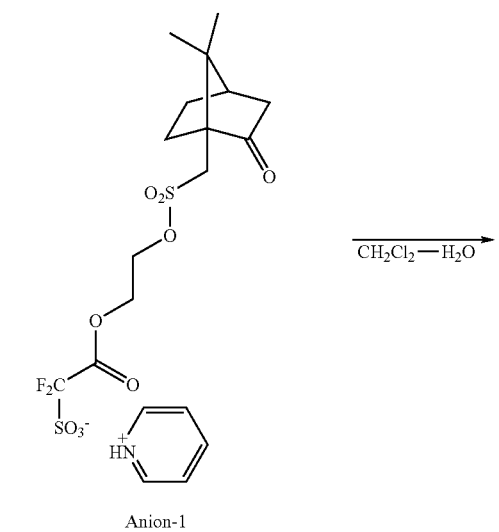

Synthesis Example 2-21

Compound: Synthesis of PAG-21

The same operations as those described in the aforementioned Synthesis Example 2-2 were carried out with the exception that a bromine salt represented in chemical formula shown below was used instead of the compound represented by chemical formula E, thereby obtaining an objective compound (PAG-21). The bromine salt represented in chemical formula shown below was synthesized in accordance with Published Japanese Translation No. 2009-515944 of the PCT International Publication.

The obtained compound was analyzed by NMR, and the structure thereof was identified based on the results shown below.

$^1$H-NMR (DMSO-d6, 400 MHz): δ (ppm)=7.73-7.89 (m, 12H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.38 (s, 6H, cation–CH$_3$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=–70.2, –106.5

[Chemical Formula 85]

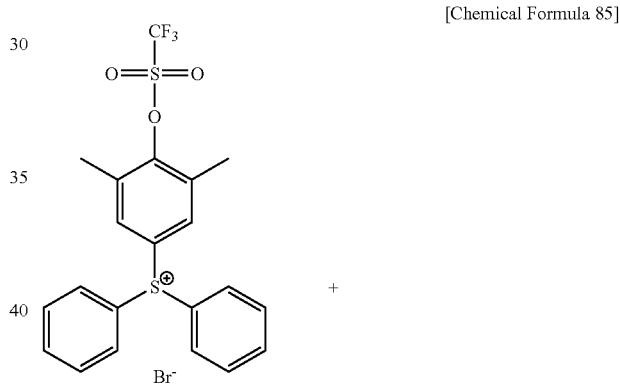

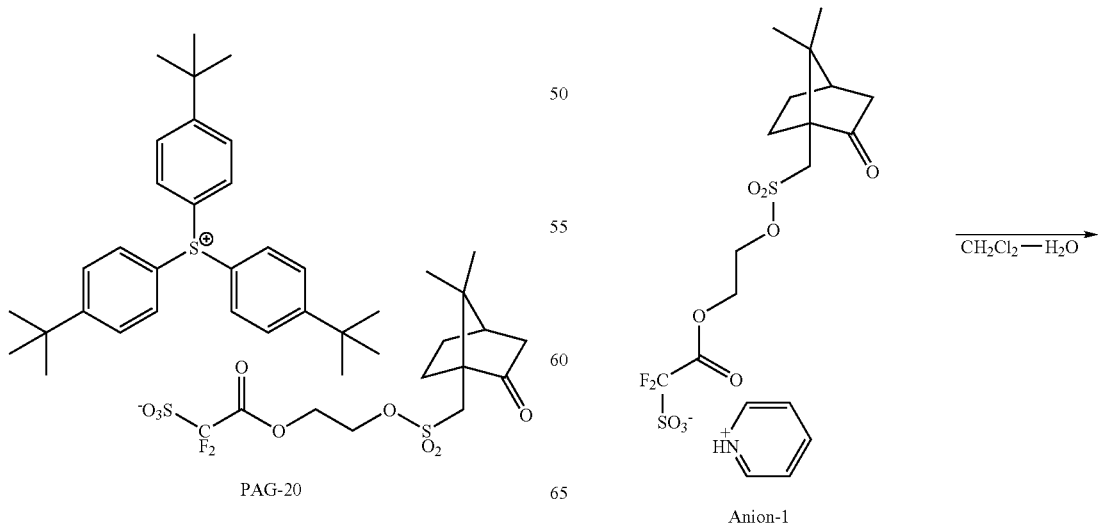

-continued

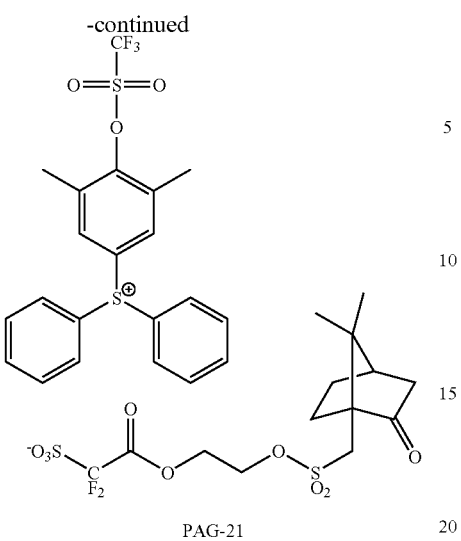

PAG-21

Synthesis Example 2-22

Compound: Synthesis of PAG-22

The same operations as those described in the aforementioned Synthesis Example 2-2 were carried out with the exception that a bromine salt represented in chemical formula shown below was used instead of the compound represented by chemical formula E, thereby obtaining an objective compound (PAG-22).

The obtained compound was analyzed by NMR, and the structure thereof was identified based on the results shown below.

$^1$H-NMR (DMSO-d6, 400 MHz): δ (ppm)=7.69-7.85 (m, 10H, ArH), 7.56 (s, 2H, ArH), 4.75 (s, 4H, cation–CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 8H, camphor+ArCH$_3$), 2.19 (m, 2H, Adamantane), 2.07 (t, 1H, camphor), 1.47-1.99 (m, 18H, camphor+Adamantane), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 86]

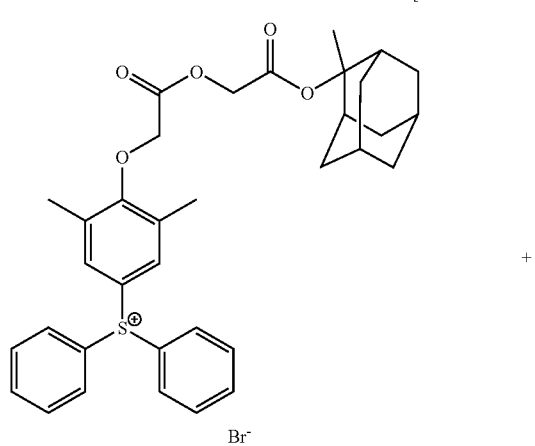

+

-continued

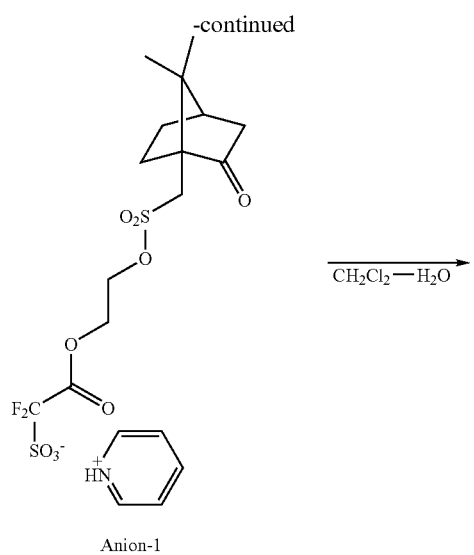

Anion-1

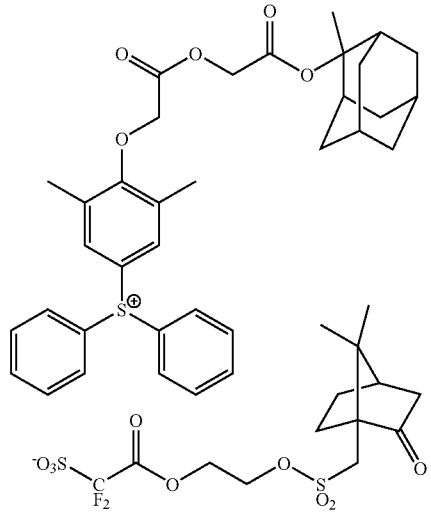

PAG-22

The bromine salt used in Synthesis Example 2-22 was synthesized by the following procedures.

21.7 g of a compound (22a) was dissolved in 108.5 g of acetonitrile, and 6.00 g of triethylamine was then added thereto, thereby obtaining a uniform solution. 57.6 g of a 25% by weight acetonitrile solution of a compound (22b) was then dropwise added thereto, and a reaction was conducted at a reflux temperature for 2 hours, Thereafter, acetonitrile was removed from the reaction mixture, and the resultant was dissolved in 300 g of pure water. Then, the resulting solution was washed twice with 150 g of a 1:1 (wt/wt) mixed solvent of n-hexane and TBME. 300 g of methylene chloride and 30 g of sodium chloride were then added thereto, followed by stirring. Then, the resulting organic phase was collected, and washed once with 150 g of a 10% aqueous sodium chloride solution and once with pure water. Thereafter, the organic phase was concentrated and solidified, thereby obtaining 20.9 g of an objective bromine salt in the form of a white solid.

[Chemical Formula 87]

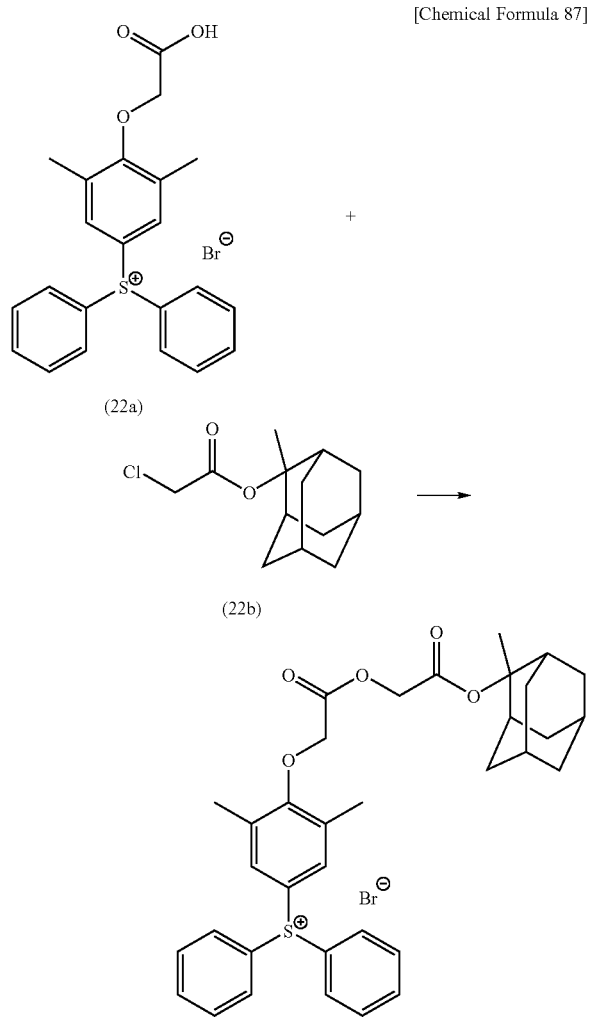

Synthesis Example 2-23

Compound: Synthesis of PAG-23

The same operations as those described in the aforementioned Synthesis Example 2-2 were carried out with the exception that a bromine salt represented in chemical formula shown below was used instead of the compound represented by chemical formula E, thereby obtaining an objective compound (PAG-23).

The obtained compound was analyzed by NMR, and the structure thereof was identified based on the results shown below.

$^1$H-NMR (DMSO-d6, 400 MHz): δ (ppm)=7.72-7.84 (m, 10H, ArH), 7.59 (s, 2H, ArH), 4.56 (s, 2H, cation–CH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.49 (m, 2H, Adamantane), 2.24-2.34 (m, 15H, camphor+Adamantane+ArCH$_3$), 2.07 (t, 1H, camphor), 1.92-1.99 (m, 4H, camphor+Adamantane), 1.72-1.79 (m, 2H, Adamantane), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 88]

PAG-23

The bromine salt used in Synthesis Example 2-23 was synthesized by the following procedures.

13.2 g of a compound (23a) and 132 g of dichloromethane were added to a three-necked flask under a nitrogen atmosphere, and the resulting mixture was cooled to 5° C. or less. 0.73 g of N,N-dimethylaminopyridine (DMAP) was then added thereto, followed by stirring at 5° C. or less for 5 minutes. Then, 14.4 g of 1-ethyl-3-(3-dimethylaminopropyl)carbodiimide hydrochloride was added thereto. After stirring the resulting mixture for 10 minutes, 30 g of a dichloromethane solution containing 15 g of 5-hydroxy-2-adamantanone was gradually dropwise added thereto. After completion of the addition, the temperature was raised to room temperature, and the resulting mixture was stirred at room temperature for 31 hours. Then, the resultant was washed with diluted hydrochloric acid, and then washed repeatedly with pure water. The resulting organic phase was then dropwise added to 1,000 g of n-hexane to reprecipitate, thereby obtaining 12.3 g of an objective bromine salt.

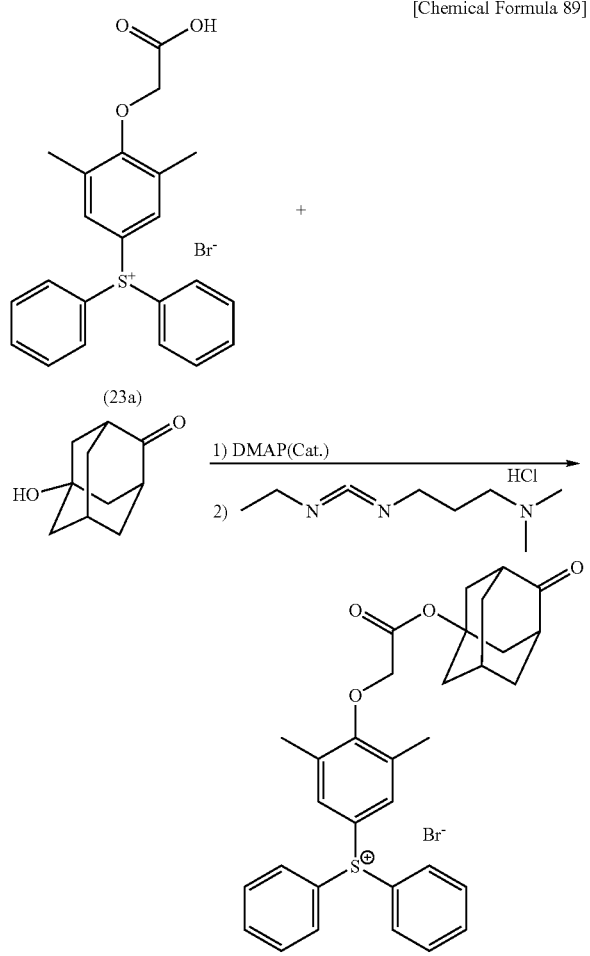

Synthesis Example 2-24

Compound: Synthesis of PAG-24

The same operations as those described in the aforementioned Synthesis Example 2-2 were carried out with the exception that a bromine salt represented in chemical formula shown below was used instead of the compound represented by chemical formula E, thereby obtaining an objective compound (PAG-24).

The obtained compound was analyzed by NMR, and the structure thereof was identified based on the results shown below.

$^1$H-NMR (DMSO-d6, 400 MHz): δ (ppm)=7.72-7.84 (m, 10H, ArH), 7.59 (s, 2H, ArH), 4.64 (s, 2H, cation–CH$_2$), 4.50-4.54 (m, 4H, OCH$_2$CH$_2$O), 3.70 (s, 31-1, OCH$_3$), 3.57 (d, 1H, CH$_2$SO$_2$), 3.36 (s, 1H, CH$_2$SO$_2$), 2.24-2.34 (m, 8H, camphor+ArCH$_3$), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

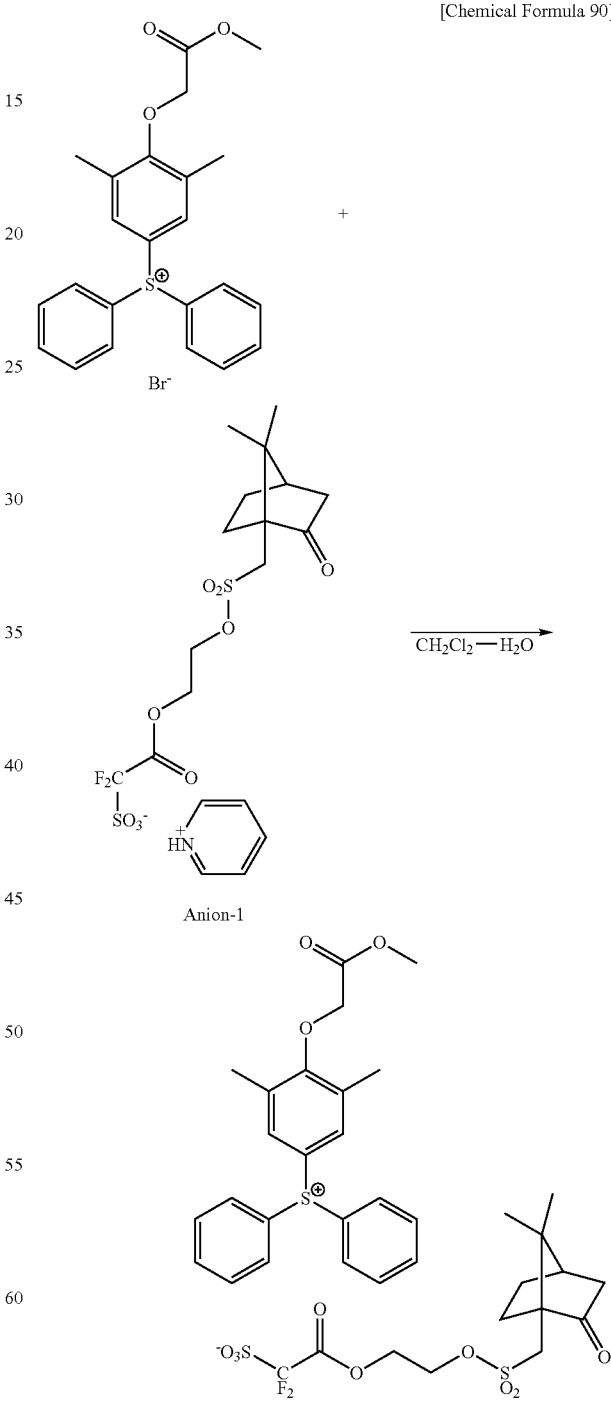

Synthesis Example 2-25

Compound: Synthesis of PAG-25

The same operations as those described in the aforementioned Synthesis Example 2-2 were carried out with the exception that a bromine salt represented in chemical formula shown below was used instead of the compound represented by chemical formula E, thereby obtaining an objective compound (PAG-25).

The obtained compound was analyzed by NMR, and the structure thereof was identified based on the results shown below.

$^1$H-NMR (DMSO-d6, 400 MHz): δ (ppm)=7.78-7.89 (m, 10H, ArH), 7.64 (s, 2H, ArH), 4.50-4.54 (m, 4H, OCH$_2$CH$_2$O), 3.79 (s, 3H, OCH$_3$), 3.57 (d, 1H, CH$_2$SO$_2$), 3.36 (s, 1H, CH$_2$SO$_2$), 2.24-2.34 (m, 8H, camphor+ArCH$_3$), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

[Chemical Formula 91]

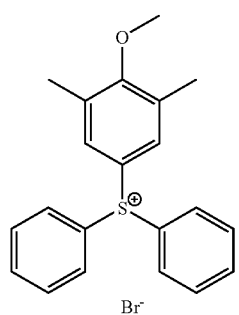

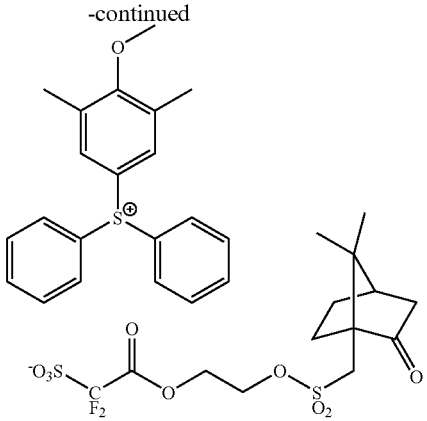

PAG-25

Synthesis Example 2-26

Compound: Synthesis of PAG-26

The same operations as those described in the aforementioned Synthesis Example 2-2 were carried out with the exception that a compound (26a) represented by chemical formula (26a) shown below was used instead of the compound represented by chemical formula E, thereby obtaining an objective compound (PAG-26).

The obtained compound was analyzed by NMR, and the structure thereof was identified based on the results shown below.

$^1$H-NMR (DMSO-d6, 400 MHz): δ (ppm)=8.44 (s, 4H, ArH in ArC=O), 7.78-7.90 (m, 24H, ArH), 4.50-4.54 (m, 8H, OCH$_2$CH$_2$O), 3.57 (d, 2H, CH$_2$SO$_2$), 3.36 (s, 2H, CH$_2$SO$_2$), 2.24-2.34 (m, 4H, camphor), 2.23 (s, 12H, ArCH$_3$), 2.07 (t, 2H, camphor), 1.92-1.99 (m, 4H, camphor), 1.56-1.62 (m, 2H, camphor), 1.42-1.45 (m, 2H, camphor), 1.04 (s, 6H, CH$_3$), 0.84 (s, 6H, CH$_3$)

$^{19}$F-NMR (DMSO-d6, 376 MHz): δ (ppm)=−106.5

[Chemical Formula 92]

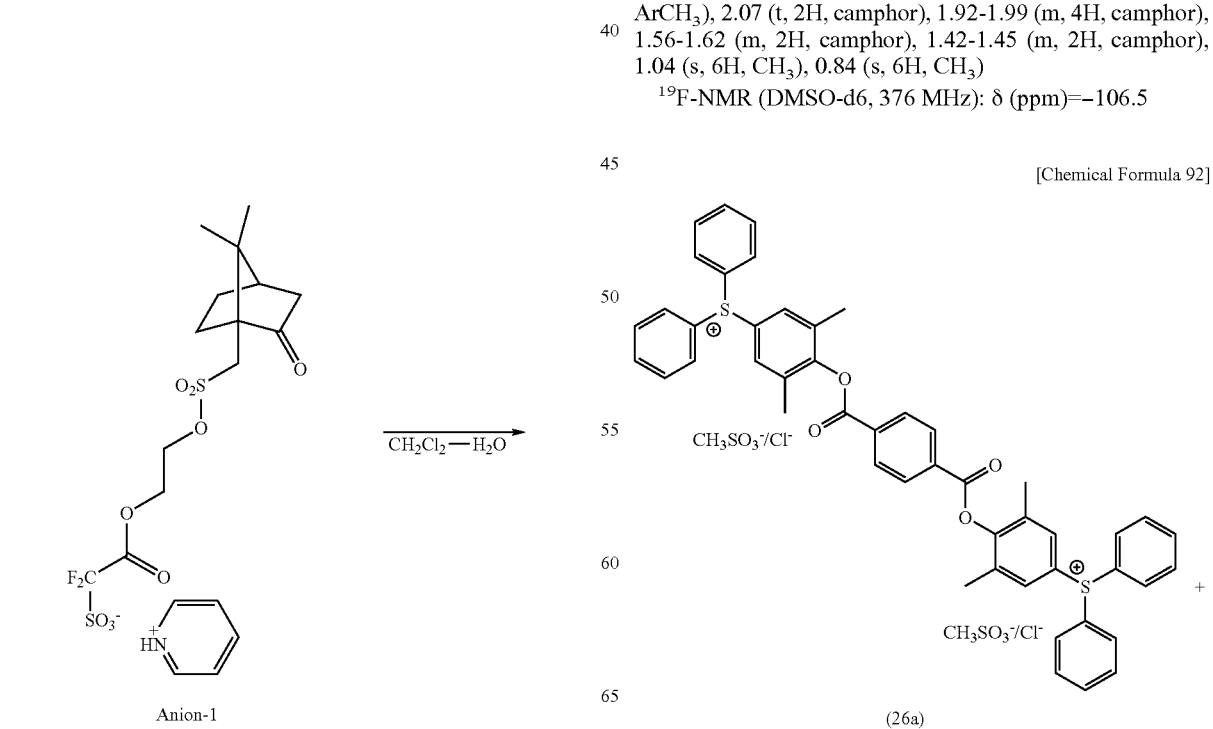

Anion-1

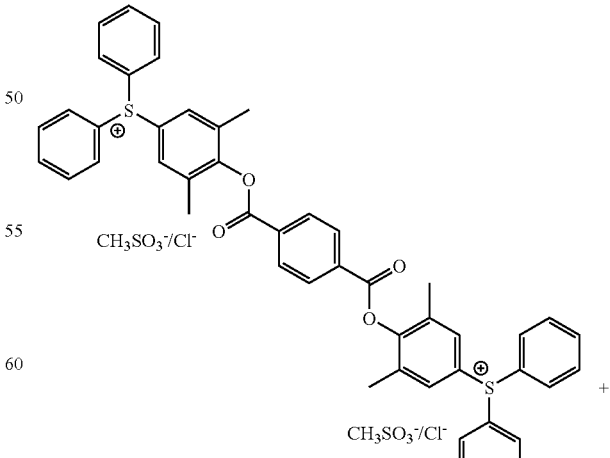

(26a)

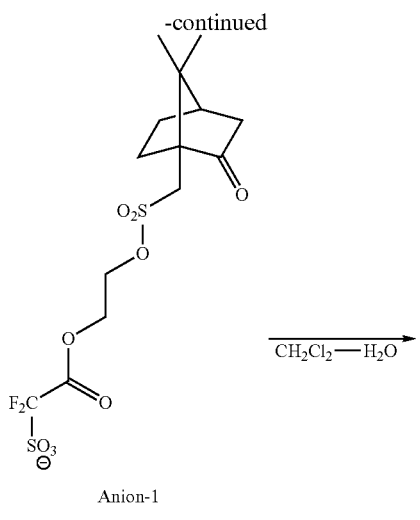

Anion-1

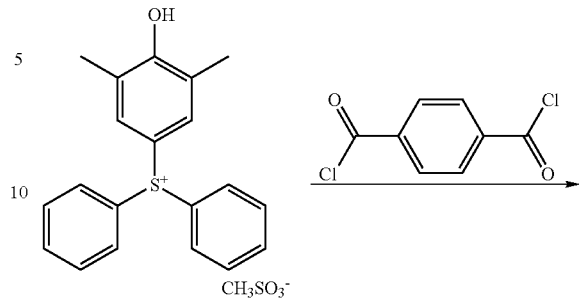

(5)

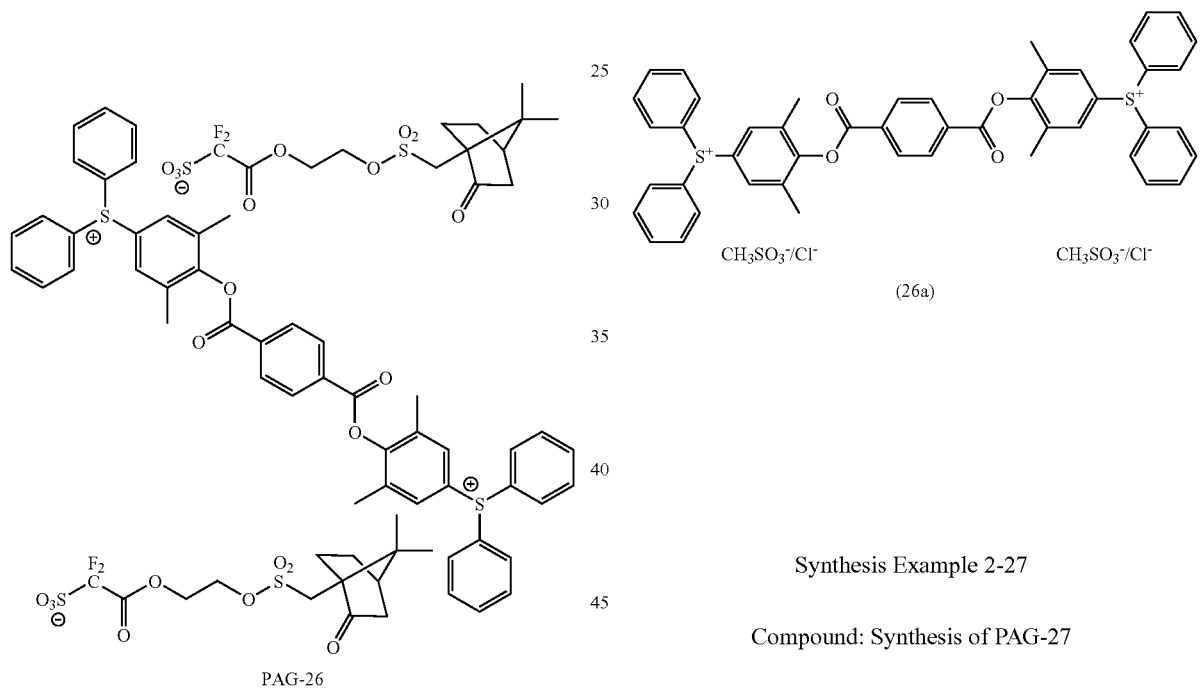

PAG-26

(26a)

The compound (26a) used in Synthesis Example 2-26 was synthesized by the following procedures.

16.1 g of a compound (5), 4.1 g of terephthalic acid chloride, and 350 g of dichloromethane were added to a reaction vessel under a nitrogen atmosphere and cooled to 10° C. or less. A dichloromethane solution containing 4.5 g of triethylamine was then gradually dropwise added thereto. After completion of the addition, the temperature was raised to room temperature, and the resulting mixture was stirred for 10 minutes. Thereafter, the resulting organic phase was washed by adding diluted hydrochloric acid to the resulting reaction solution, followed by washing with pure water. Then, 1,050 g of hexane was dropwise added to the resulting dichloromethane solution to crystallize, thereby obtaining 13 g of an objective bromine salt. The resultant was analyzed by ion chromatography (IC). As a result, the molar ratio of counter anions was $CH_3SO_3^-/Cl^-=45.9/54.1$.

Synthesis Example 2-27

Compound: Synthesis of PAG-27

The same operations as those described in the aforementioned Synthesis Example 2-2 were carried out with the exception that a compound (27a) represented by chemical formula (27a) shown below was used instead of the compound represented by chemical formula E, thereby obtaining an objective compound (PAG-27).

The obtained compound was analyzed by NMR, and the structure thereof was identified based on the results shown below.

$^1$H-NMR (DMSO-d6, 400 MHz): δ (ppm)=8.90 (s, 1H, ArH in ArC=O), 8.60 (dd, 2H, ArH in ArC=O), 7.77-7.96 (m, 25H, ArH in cation ArH in ArC=O), 4.50-4.54 (m, 8H, OCH$_2$CH$_2$O), 3.57 (d, 2H, CH$_2$SO$_2$), 3.36 (s, 2H, CH$_2$SO$_2$), 2.24-2.34 (m, 16H, camphor+ArCH$_3$), 2.07 (t, 2H, camphor), 1.92-1.99 (m, 4H, camphor), 1.56-1.62 (m, 2H, camphor), 1.42-1.45 (m, 2H, camphor), 1.04 (s, 6H, CH$_3$), 0.84 (s, 6H, CH$_3$)

$^{19}$F-NMR (DMSO-d6, 376 MHz): δ (ppm)=−106.5

[Chemical Formula 94]

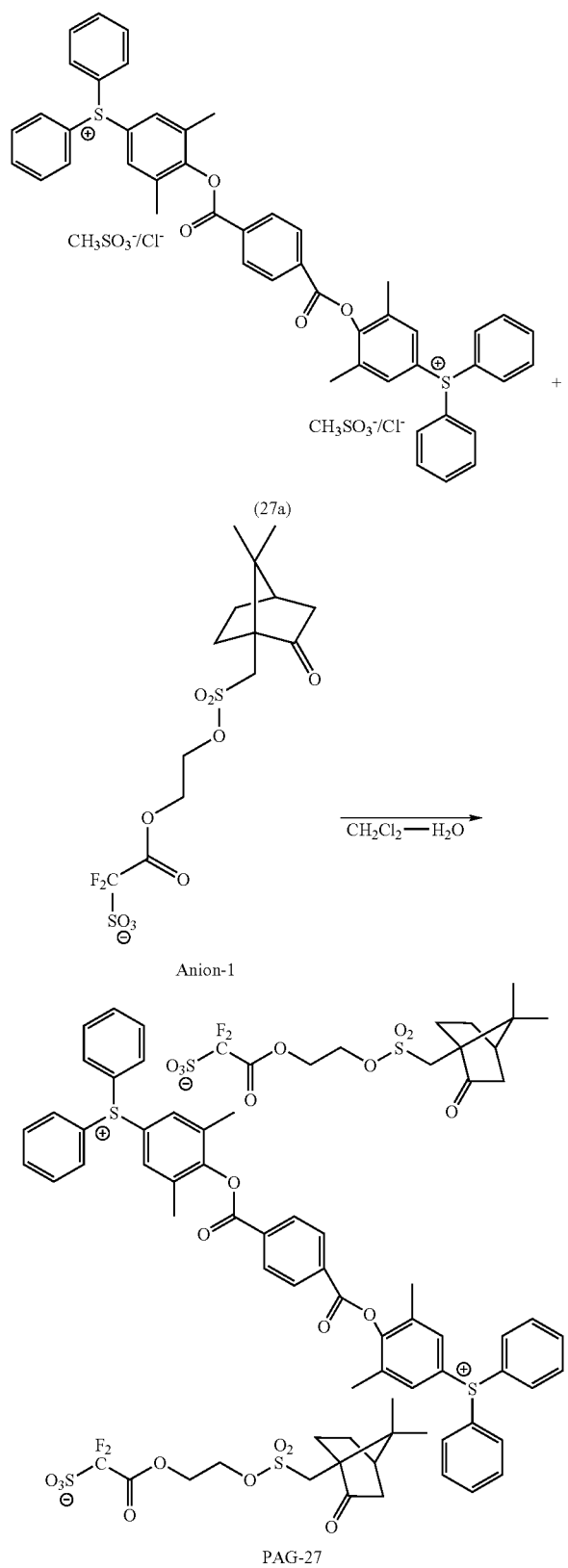

The compound (27a) used in Synthesis Example 2-27 was synthesized by the following procedures.

16.1 g of a compound (5), 4.1 g of isophthalic acid chloride, and 187 g of dichloromethane were added to a reaction vessel under a nitrogen atmosphere and cooled to 10° C. or less. A dichloromethane solution containing 4.5 g of triethylamine was then gradually dropwise added thereto. After completion of the addition, the temperature was raised to room temperature, and the resulting mixture was stirred for 10 minutes. Thereafter, the resulting organic phase was washed by adding diluted hydrochloric acid to the resulting reaction solution, followed by washing with pure water. Then, 1,050 g of hexane was dropwise added to the resulting dichloromethane solution to crystallize, thereby obtaining 14 g of an objective bromine salt. The resultant was analyzed by ion chromatography (IC). As a result, the molar ratio of counter anions was $CH_3SO_3^-/Cl^- = 43.4/56.6$.

[Chemical Formula 95]

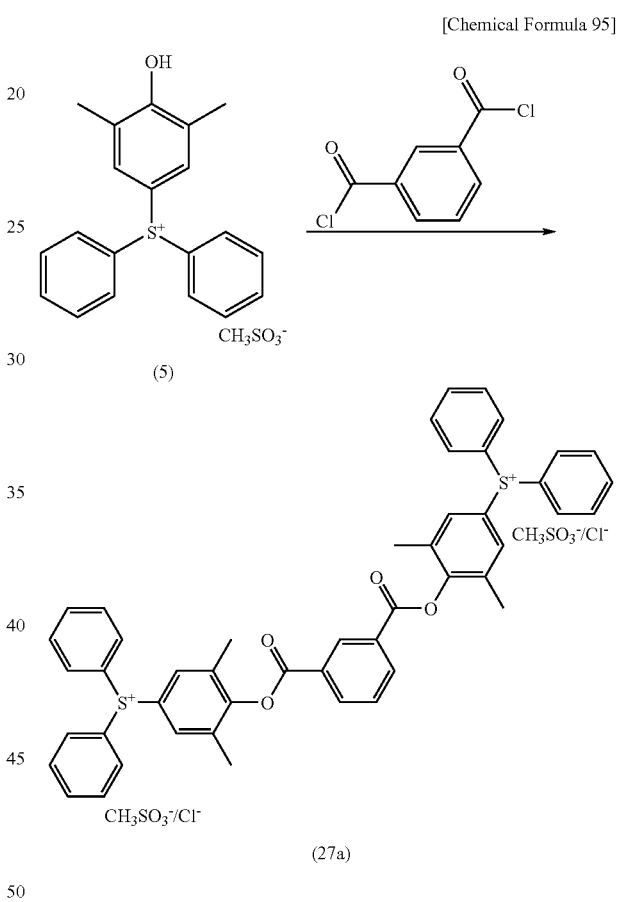

Synthesis Example 2-28

Compound: Synthesis of PAG-28

The same operations as those described in the aforementioned Synthesis Example 2-2 were carried out with the exception that a bromine salt represented in chemical formula shown below was used instead of the compound represented by chemical formula E, thereby obtaining an objective compound (PAG-28). The bromine salt represented in chemical formula shown below was synthesized in accordance with Japanese Unexamined Patent Application, First Publication No. 2008-107377.

The obtained compound was analyzed by NMR, and the structure thereof was identified based on the results shown below.

¹H-NMR (DMSO-d6, 400 MHz): δ (ppm)=7.76-7.87 (m, 10H, ArH), 7.69 (s, 2H, ArH), 4.50-4.54 (m, 4H, OCH₂CH₂O), 3.57 (d, 1H, CH₂SO₂), 3.36 (s, 1H, CH₂SO₂), 2.24-2.34 (m, 2H, camphor), 2.13 (s, 6H, ArCH₃), 2.07 (t, 1H, camphor), 1.62-2.03 (m, 18H, camphor+Adamantane), 1.42-1.45 (m, 1H, camphor), 1.04 (s, 3H, CH₃), 0.84 (s, 3H, CH₃)

¹⁹F-NMR (DMSO-d6, 376 MHz): δ (ppm)=−106.5

[Chemical Formula 96]

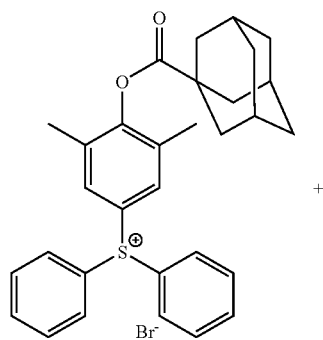

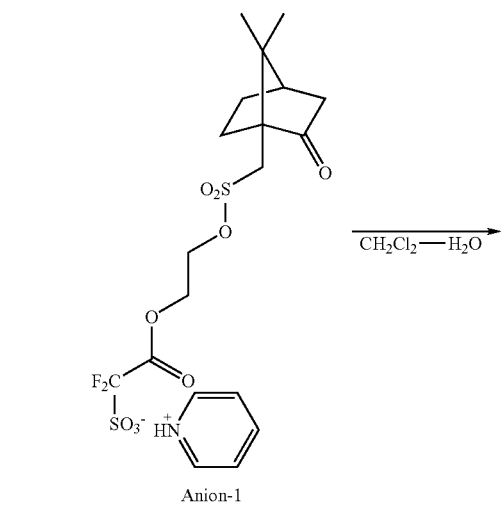

PAG-28

Synthesis Example 2-29

Compound: Synthesis of PAG-29

The same operations as those described in the aforementioned Synthesis Example 2-2 were carried out with the exception that a bromine salt represented in chemical formula shown below was used instead of the compound represented by chemical formula E, thereby obtaining an objective compound (PAG-29).

The obtained compound was analyzed by NMR, and the structure thereof was identified based on the results shown below.

¹H-NMR (DMSO-d6, 400 MHz): δ (ppm)=7.79-7.93 (m, 12H, ArH), 4.50-4.54 (m, 4H, OCH₂CH₂O), 3.57 (d, 1H, CH₂SO₂), 3.36 (s, 1H, CH₂SO₂), 2.73 (t, 2H, cation —COCH₂), 2.24-2.34 (m, 2H, camphor), 2.19 (s, 6H, ArCH₃), 2.07 (t, 1H, camphor), 1.92-1.99 (m, 2H, camphor), 1.56-1.72 (m, 3H, camphor+cation–CH₂), 1.42-1.45 (m, 1H, camphor), 1.25-1.38 (m, 14H, cation–CH₂), 1.04 (s, 3H, CH₃), 0.84 (m, 6H, anion —CH₃+cation–CH₃)

¹⁹F-NMR (DMSO-d6, 376 MHz): δ (ppm)=−106.5

[Chemical Formula 97]

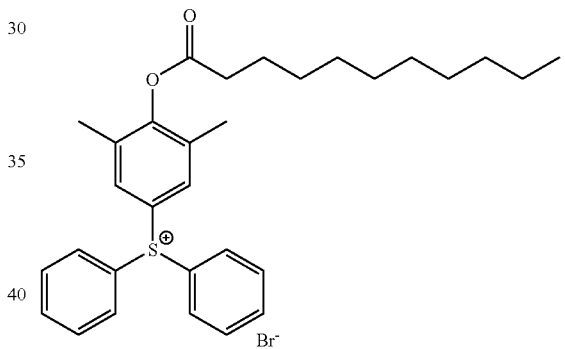

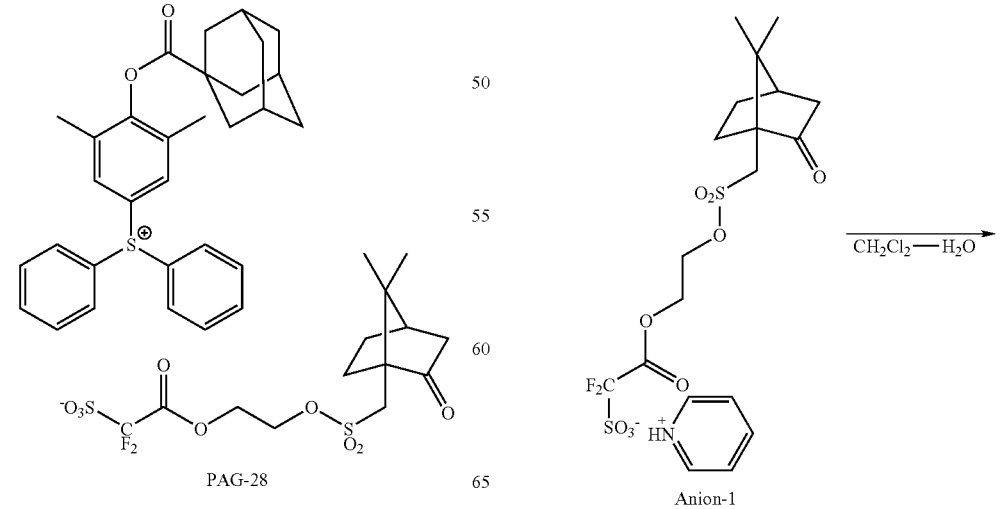

Anion-1

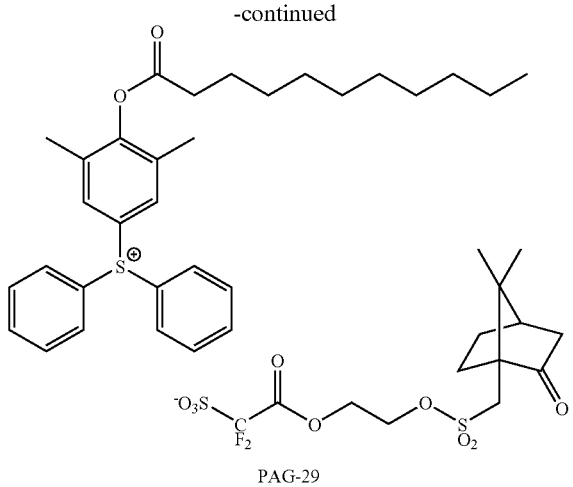

PAG-29

The bromine salt used in Synthesis Example 2-29 was synthesized by the following procedures.

28.98 g of a compound (29a), 289.80 g of dichloromethane, and 9.47 g of triethylamine were mixed and cooled to 10° C. while stirring. Then, 17.69 g of undecane acid chloride was dropwise added thereto, and after raising the temperature to room temperature, the resulting mixture was stirred for 1 hour. Then, the reaction solution was washed twice with 109.36 g of a saturated sodium bromide aqueous solution and 4 times with 109.36 g of pure water, and the resulting organic phase was then concentrated, thereby obtaining 38 g of an objective bromine salt.

Synthesis Example 2-30

Compound: Synthesis of PAG-30

The same operations as those described in the aforementioned Synthesis Example 2-2 were carried out with the exception that a compound (30a) represented by chemical formula (30a) shown below was used instead of the compound represented by chemical formula E, thereby obtaining an objective compound (PAG-30).

The obtained compound was analyzed by NMR, and the structure thereof was identified based on the results shown below.

$^1$H-NMR (DMSO-d6, 400 MHz): δ (ppm)=8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 31-1, CH$_3$)

$^{19}$F-NMR (DMSO-d6, 376 MHz): δ (ppm)=−62.1, −106.5

[Chemical Formula 98]

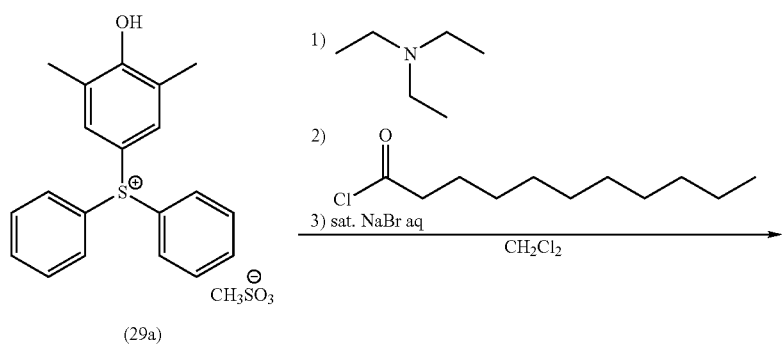

(29a)

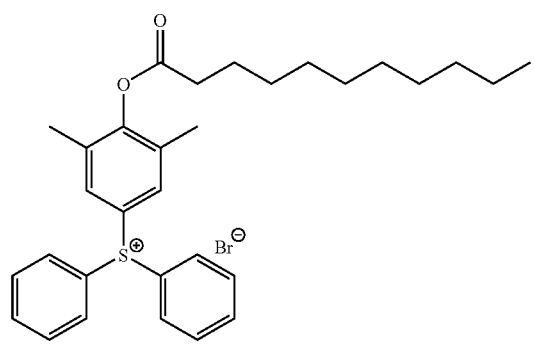

[Chemical Formula 99]

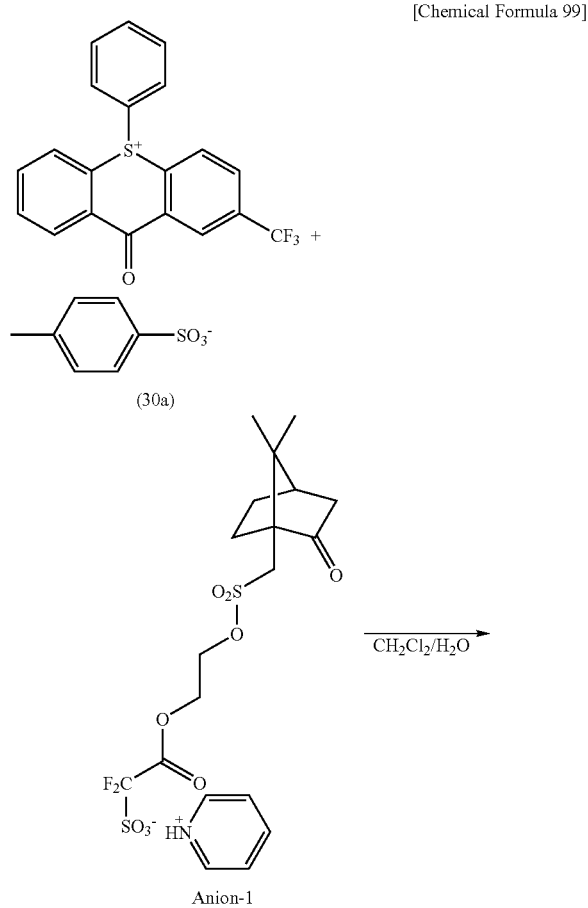

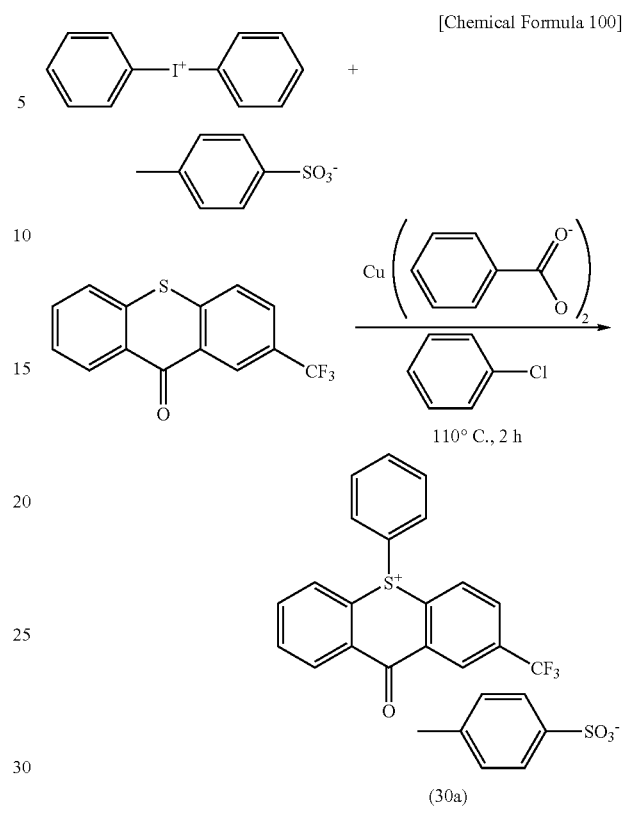

Synthesis Example 2-31

Compound: Synthesis of PAG-31

The same operations as those described in the aforementioned Synthesis Example 2-2 were carried out with the exception that an n-butyl sulfate represented in chemical formula shown below was used instead of the compound represented by chemical formula E, thereby obtaining an objective compound (PAG-31).

The obtained compound was analyzed by NMR, and the structure thereof was identified based on the results shown below.

$^1$H-NMR (DMSO-d6, 400 MHz): δ (ppm)=4.50-4.54 (m, 4H, OCH$_2$CH$_2$O), 3.57 (d, 1H, CH$_2$SO$_2$), 3.36 (m, 7H, CH$_2$SO$_2$+cation–CH$_2$), 2.24-2.34 (m, 2H, camphor), 2.07 (t, 1H, camphor), 1.92-1.99 (m, 2H, camphor), 1.68 (quintet, 6H, cation–CH$_2$), 1.56-1.62 (m, 1H, camphor), 1.35-1.45 (m, 7H, camphor-1–cation–CH$_2$), 1.04 (s, 3H, CH$_3$), 0.81-0.93 (m, 12H, anion —CH$_3$+cation–CH$_3$)

$^{19}$F-NMR (DMSO-d6, 376 MHz): δ (ppm)=−106.5

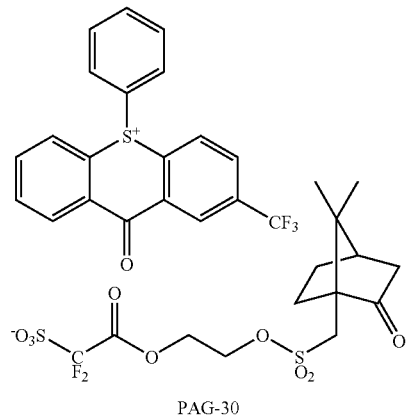

PAG-30

The compound (30a) used in Synthesis Example 2-30 was synthesized by the following procedures.

34.10 g of diphenyliodonium p-toluenesulfonate, 51.00 g of chlorobenzene, 17.60 g of 2-(trifluoromethyl)thioxanten-9-one, and 0.463 g of copper (II) benzoate were placed in a reaction vessel and stirred therein at 110° C. for 2 hours, and the reaction solution was then cooled to 50° C., followed by the dropwise addition of 200 g of t-butylmethyl ether thereto. The obtained solid was redissolved in 164 g of dichloromethane, washed with 16.5 g of 1% NH$_3$ aq., and then washed 4 times with 16.5 g of pure water. Thereafter, the resulting organic phase was concentrated and dried under reduced pressure, thereby obtaining 6.6 g of an objective compound (30a).

[Chemical Formula 101]

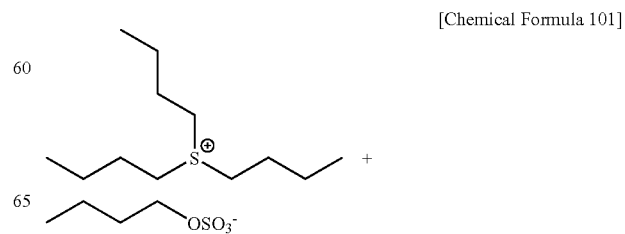

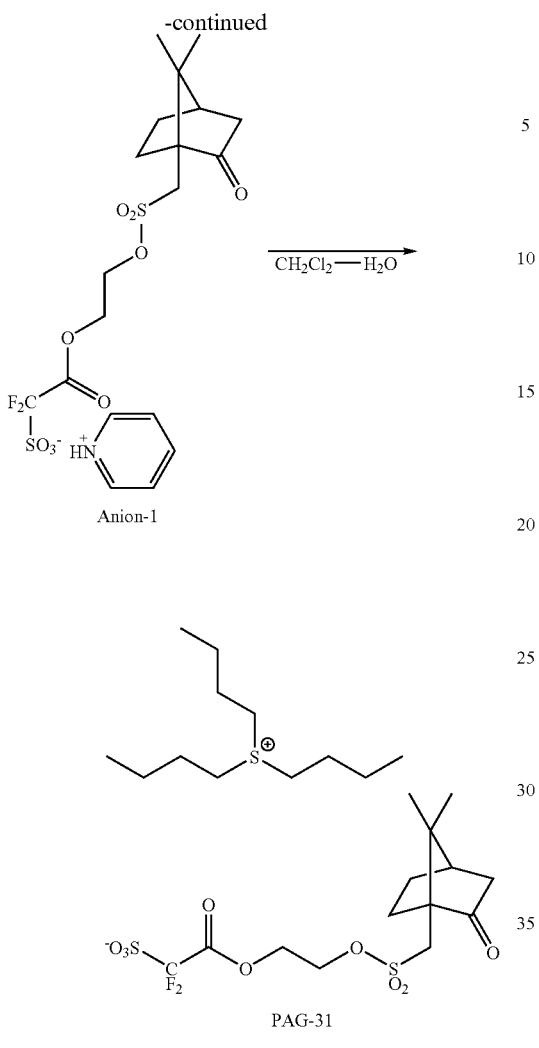

Synthesis Example 2-32

Compound: Synthesis of PAG-32

The same operations as those described in the aforementioned Synthesis Example 2-2 were carried out with the exception that a bromine salt represented in chemical formula shown below was used instead of the compound represented by chemical formula E, thereby obtaining an objective compound (PAG-32). The bromine salt represented in chemical formula shown below was synthesized in accordance with Japanese Unexamined Patent Application, First Publication No. 2001-255647.

The obtained compound was analyzed by NMR, and the structure thereof was identified based on the results shown below.

$^1$H-NMR. (DMSO-d6, 400 MHz): δ (ppm)=8.29 (d, 4H, ArH), 7.93-8.09 (m, 6H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−47.9, −106.5

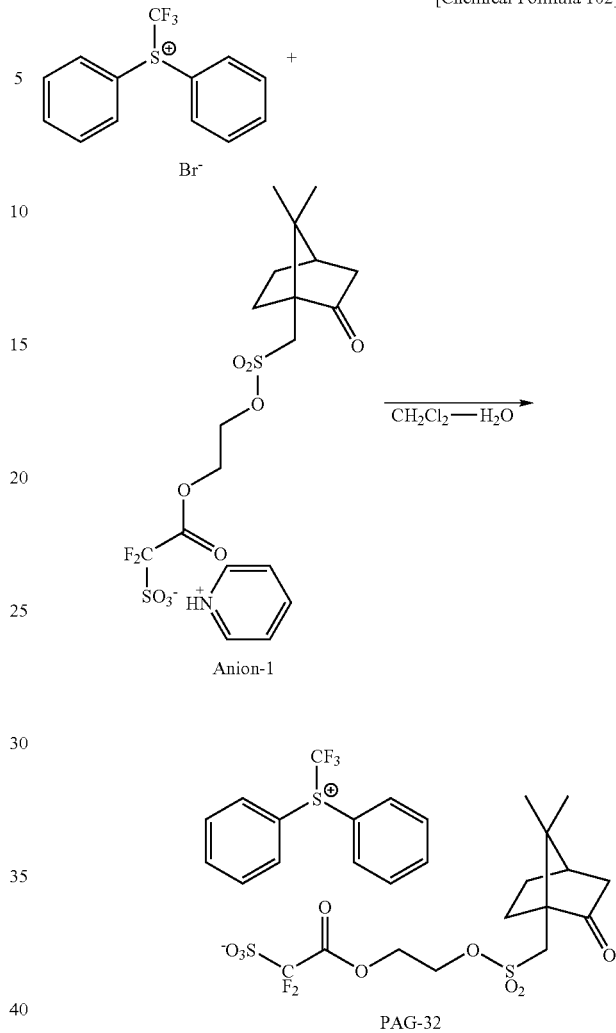

[Chemical Formula 102]

Synthesis Example 2-33

Compound: Synthesis of PAG-33

The same operations as those described in the aforementioned Synthesis Example 2-2 were carried out with the exception that a bromine salt represented in chemical formula shown below was used instead of the compound represented by chemical formula E, thereby obtaining an objective compound (PAG-33).

The obtained compound was analyzed by NMR, and the structure thereof was identified based on the results shown below.

$^1$H-NMR (DMSO-d6, 400 MHz): δ (ppm)=7.90-8.24 (m, 7H, ArH), 4.50-4.54 (m, 4H, OCH$_2$CH$_2$O), 3.85 (s, 3H, OCH$_3$), 3.57 (d, 1H, CH$_2$SO$_2$), 3.36 (s, 1H, CH$_2$SO$_2$), 2.40 (s, ArCH$_3$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−48.8, −106.5

[Chemical Formula 103]

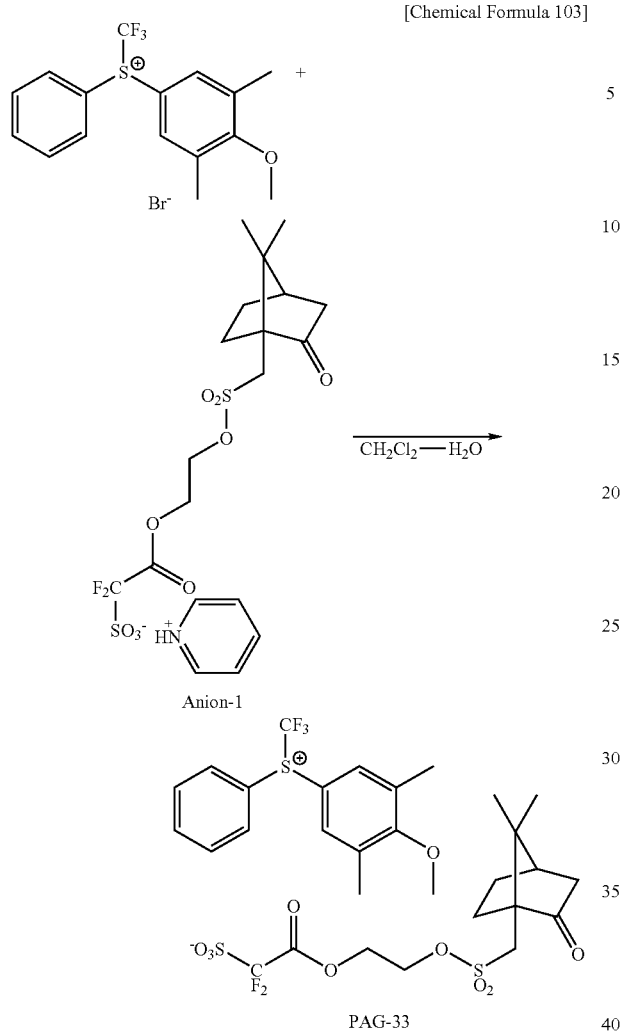

[Chemical Formula 104]

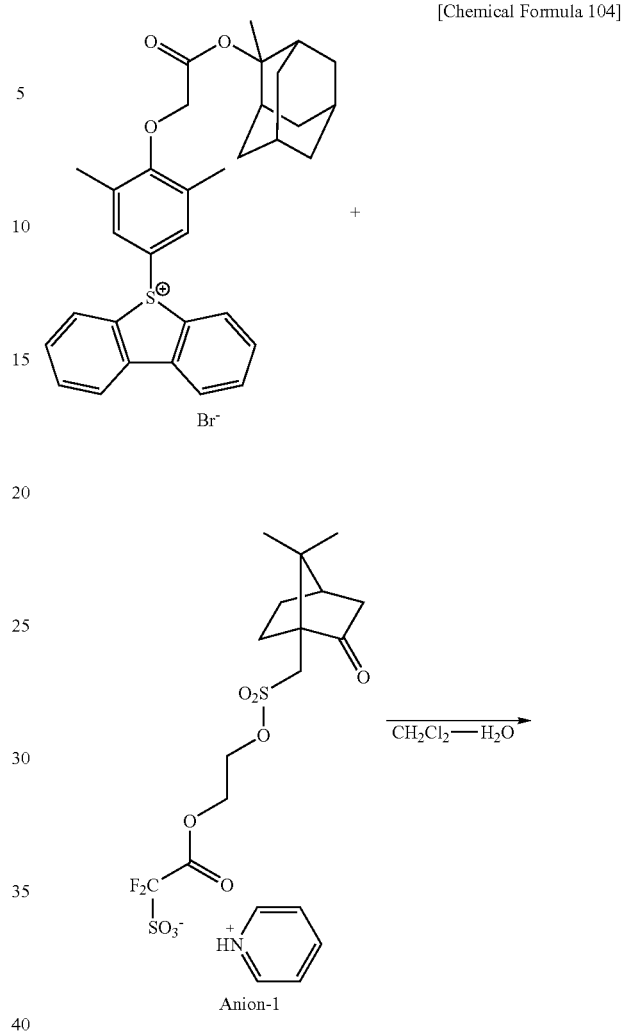

Synthesis Example 2-34

Compound: Synthesis of PAG-34

The same operations as those described in the aforementioned Synthesis Example 2-2 were carried out with the exception that a bromine salt represented in chemical formula shown below was used instead of the compound represented by chemical formula E, thereby obtaining an objective compound (PAG-34). The bromine salt represented in chemical formula shown below was synthesized in accordance with U.S. Patent Application, No. 2008-0248422.

The obtained compound was analyzed by NMR, and the structure thereof was identified based on the results shown below.

$^1$H-NMR (DMSO-d6, 400 MHz): δ (ppm)=8.49 (d, 2H, ArH), 8.30 (d, 2H, ArH), 7.93 (t, 2H, ArH), 7.73 (t, 2H, ArH), 7.30 (s, 2H, ArH), 4.50-4.54 (m, 6H, OCH$_2$CH$_2$CH$_2$O+cation–OCH$_2$), 3.57 (d, 1H, CH$_2$SO$_2$), 3.36 (s, 1H, CH$_2$SO$_2$), 2.24-2.34 (m, 2H, camphor), 2.16-2.23 (m, 8H, ArCH$_3$ Adamantane), 2.07 (t, 1H, camphor), 1.92-1.99 (m, 2H, camphor), 1.42-1.91 (m, 17H, Adamantane camphor), 1.04 (s, 3H, CH$_3$), 0.84 (s, 3H, CH$_3$)

$^{19}$F-NMR (DMSO-d6, 376 MHz): δ (ppm)=−106.5

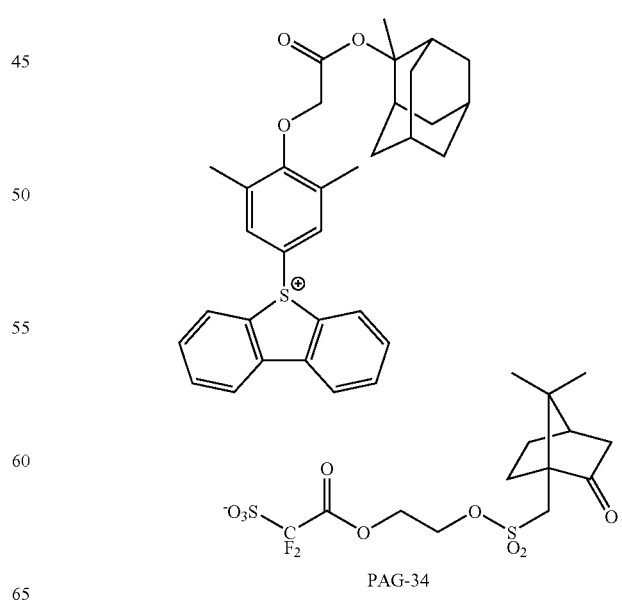

Synthesis Example 2-35

Compound: Synthesis of PAG-35

The same operations as those described in the aforementioned Synthesis Example 2-2 were carried out with the exception that a bromine salt represented in chemical formula shown below was used instead of the compound represented by chemical formula E, thereby obtaining an objective compound (PAG-35).

The obtained compound was analyzed by NMR, and the structure thereof was identified based on the results shown below.

$^1$H-NMR (DMSO-d6, 400 MHz): δ (ppm)=9.73 (brs, 1H, OH), 8.47 (d, 2H, ArH), 8.24 (d, 2H, ArH), 7.91 (t, 2H, ArH), 7.71 (t, 2H, ArH), 7.18 (s, 2H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.10 (s, 6H, ArCH$_3$), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR. (DMSO-d6, 376 MHz): δ (ppm)=−106.5

[Chemical Formula 105]

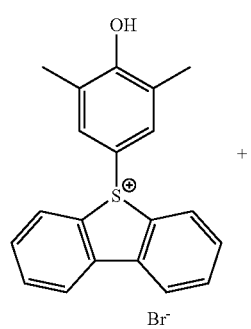

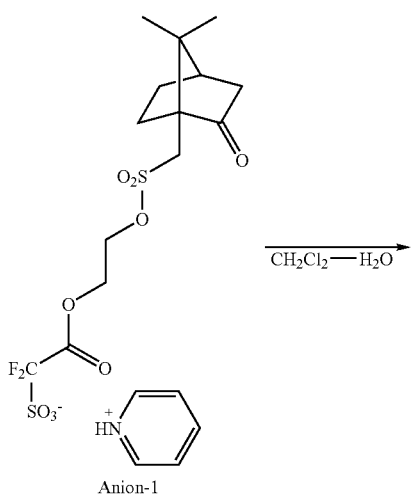

Anion-1

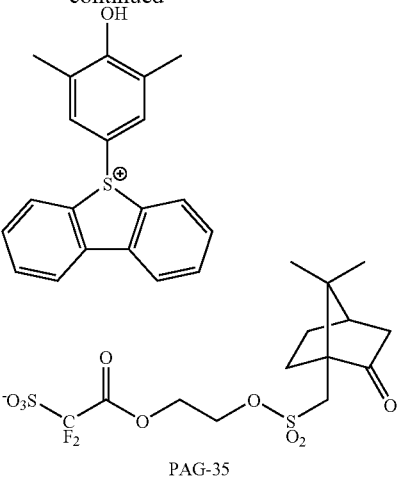

PAG-35

Synthesis Example 2-36

Compound: Synthesis of PAG-36

The same operations as those described in the aforementioned Synthesis Example 2-2 were carried out with the exception that a compound (36b) represented by chemical formula (36b) shown below was used instead of the compound represented by chemical formula E, thereby obtaining an objective compound (PAG-36).

The obtained compound was analyzed by NMR, and the structure thereof was identified based on the results shown below.

$^1$H-NMR (DMSO-d6, 400 MHz): δ (ppm)=735-7.87 (m, 10H, ArH), 7.62 (s, 2H, ArH), 4.50-4.54 (m, 4H, OCH$_2$CH$_2$O), 3.97 (t, 2H, cation–CH$_2$), 3.57 (d, 1H, CH$_2$SO$_2$), 3.36 (s, 1H, CH$_2$SO$_2$), 2.03-2.56 (m, 1311, camphor+cation–CH$_2$+ArCH$_3$), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−78.3, −106.5, −111.6, −121.8, −123.5

[Chemical Formula 106]

(36b)

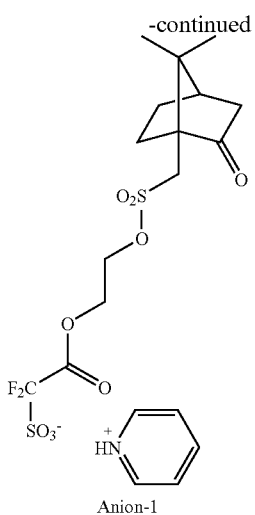

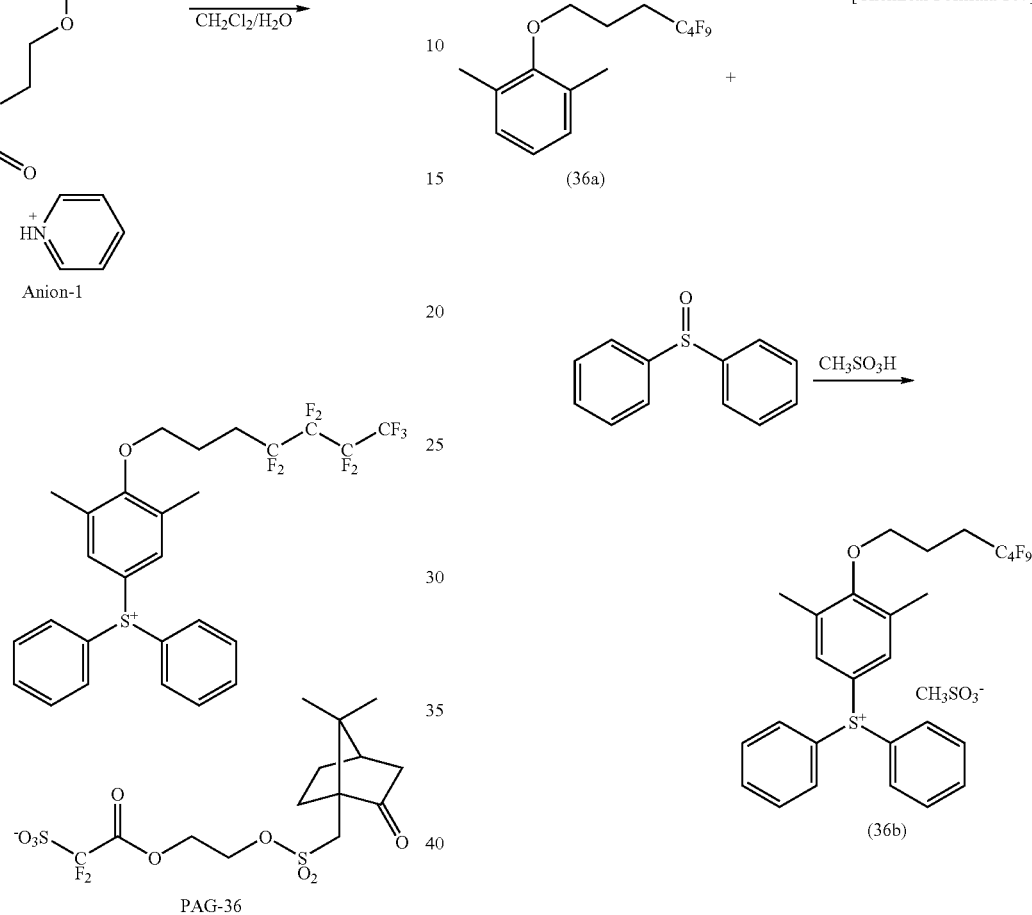

Synthesis Example 2-37

Compound: Synthesis of PAG-37

The same operations as those described in the aforementioned Synthesis Example 2-2 were carried out with the exception that a compound (37b) represented by chemical formula (37b) shown below was used instead of the compound represented by chemical formula E, thereby obtaining an objective compound (PAG-37).

The obtained compound was analyzed by NMR, and the structure thereof was identified based on the results shown below.

$^1$H-NMR (DMSO-d6, 400 MHz): δ (ppm)=7.77-7.89 (m, 10H, ArH), 7.71 (s, 2H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.51 (s, 2H, cation–CH$_2$), 2.24-2.34 (m, 2H, camphor), 2.20 (s, 6H, ArCH$_3$), 2.07 (t, 1H, camphor), 1.92-1.99 (m, 5H, camphor+Adamantane), 1.63-1.73 (m, 12H, Adamantane), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

The compound (36b) used in Synthesis Example 2-36 was synthesized by the following procedures.

3.63 g of 2,6-dimethylphenol and 72.65 g of acetone were added to a three-necked flask, and 12.34 g of potassium carbonate was then added thereto. After stirring the resulting mixture for 30 minutes, 23.22 g of 4,4,5,5,6,6,7,7,7-nonafluoroheptyliodide was added thereto, and a reaction was conducted at 40° C. for 19 hours. The reaction solution was cooled to room temperature and then filtered, and the resulting filtrate was dried and solidified. 11.37 g of t-butylmethyl ether (TBME) was added to the obtained solid, and the resultant was washed 4 times with 11.37 g of pure water. Thereafter, an organic layer was recovered by separation, concentrated, and was then purified by distillation, thereby obtaining 8.88 g of a compound (36a).

Subsequently, 2.64 g of diphosphorus pentaoxide was added to 38.4 g of methanesulfonic acid with stirring, and 8.55 g of the compound (36a) and 1.88 g of diphenylsufoxide were gradually added thereto while being cooled with ice. After stirring the mixture at room temperature for 24 hours, the resulting reaction solution was gradually dropwise added to a mixed solvent containing 91.3 g of pure water and 152.1 g of TBME. An aqueous phase was recovered by separation, and the aqueous phase was washed twice with 91.3 g of TBME and then extracted twice with 91.3 g of dichloromethane. The resulting dichloromethane phase was concentrated, thereby obtaining 7.4 g of a compound (36b) in the form of a viscous solid.

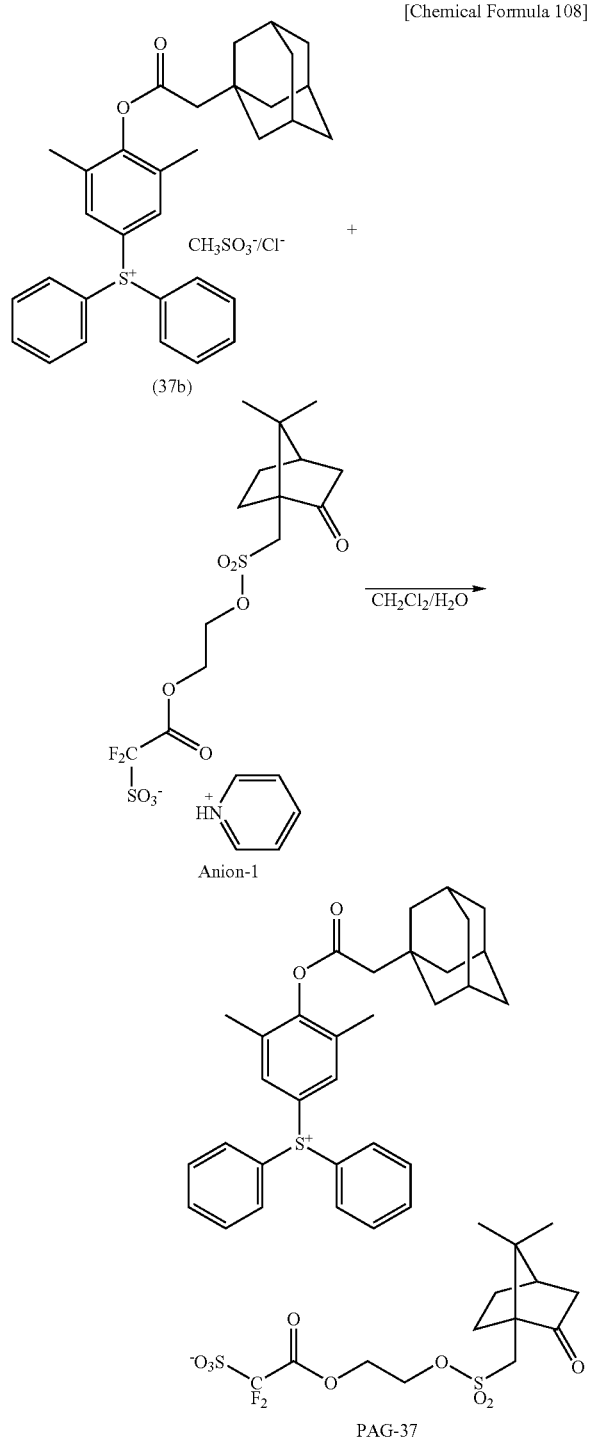

the resulting mixture was stirred at room temperature for 2 hours. The reaction solution was washed with 35.53 g of 1% HCl, and then washed three times with 35.53 g of pure water. The resulting reaction solution was then concentrated and dried, thereby obtaining 11.19 g of a compound (37b).

The compound (37b) used in Synthesis Example 2-37 was synthesized by the following procedures.

9.68 g of a compound (37a) and 67.77 g of dichloromethane were added to a three-necked flask under a nitrogen atmosphere, and the resulting mixture was cooled to 5° C. or less. 3.16 g of triethylamine was then added thereto, followed by stirring at 5° C. or less for 5 minutes, and 6.14 g of 1-adamantylacecyl chloride was then added thereto. Thereafter, the resulting mixture was stirred at 5° C. or less for 10 minutes, and the temperature was then gradually raised and Synthesis Example 2-38

Compound: Synthesis of PAG-38

The same operations as those described in the aforementioned Synthesis Example 2-2 were carried out with the exception that a bromine salt represented in chemical formula shown below was used instead of the compound represented by chemical formula E, thereby obtaining an objective compound (PAG-38).

The obtained compound was analyzed by NMR, and the structure thereof was identified based on the results shown below.

$^1$H-NMR (DMSO-d6, 400 MHz): δ (ppm)=7.74-7.84 (m, 10H, ArH), 7.61 (s, 2H, ArH), 4.49-4.62 (m, 8H, norbornane+ OCH$_2$CH$_2$O), 3.57 (d, 1H, CH$_2$SO$_2$), 3.24 (m, 1H, norbornane), 3.36 (s, 1H, CH$_2$SO$_2$), 2.44-2.54 (m, 2H, norbornane), 2.37 (s, 6H, ArCH$_3$), 2.24-2.34 (m, 2H, camphor), 1.91-2.07 (m, 5H, camphor+norbornane), 1.56-1.67 (m, 3H, camphor+ norbornane), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

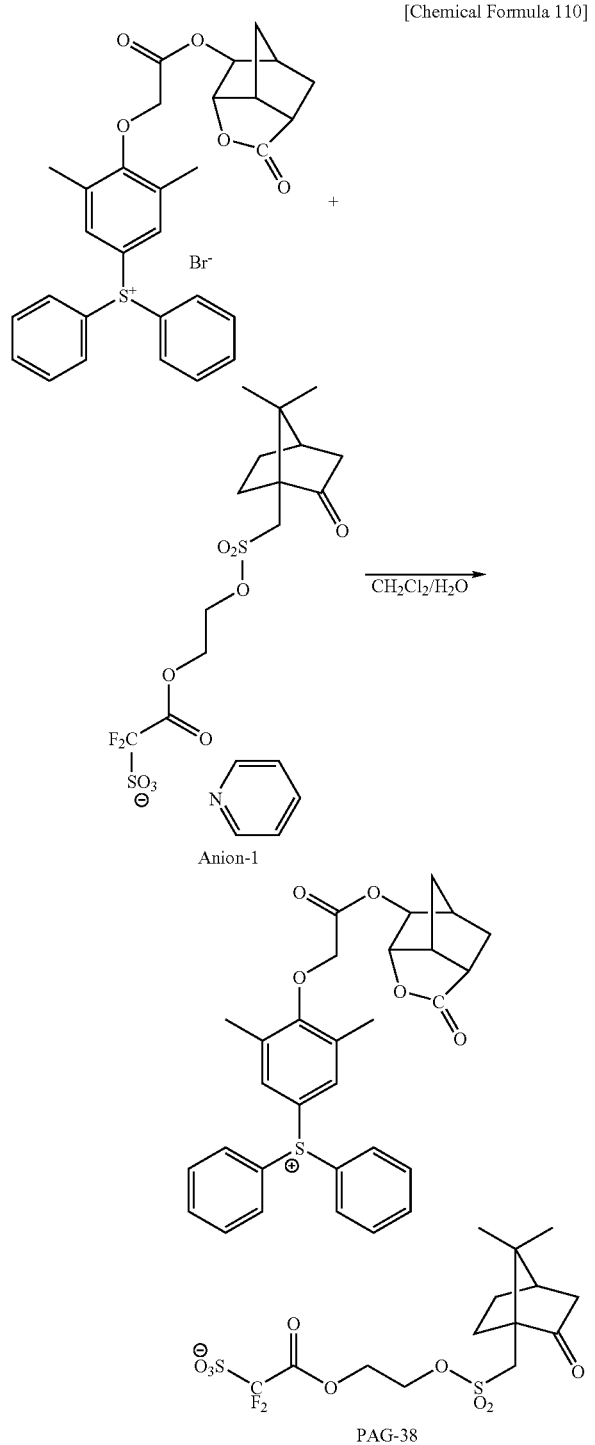

Anion-1

PAG-38

The bromine salt used in Synthesis Example 2-38 was synthesized by the following procedures.

15 g of a compound (38a) and 150 g of dichloromethane were added to a three-necked flask under a nitrogen atmosphere, and the resulting mixture was cooled to 5° C. or less. 0.84 g of N,N-dimethylaminopyridine (DMAP) was then added thereto, followed by stirring at 5° C. or less for 5 minutes. Then, 7.2 g of 1-ethyl-3-(3-dimethylaminopropyl) carbodiimide hydrochloride was added thereto. Thereafter, the resulting mixture was stirred for 10 minutes, and 4.3 g of a compound (38b) was then added thereto. After completion of the addition, the temperature was raised to room temperature, and the resulting mixture was stirred at room temperature for 15 hours. Then, the resultant was washed with diluted hydrochloric acid, and then washed repeatedly with pure water. The resulting organic phase was then dropwise added to 1,100 g of n-hexane to reprecipitate, thereby obtaining 10.1 g of an objective bromine salt.

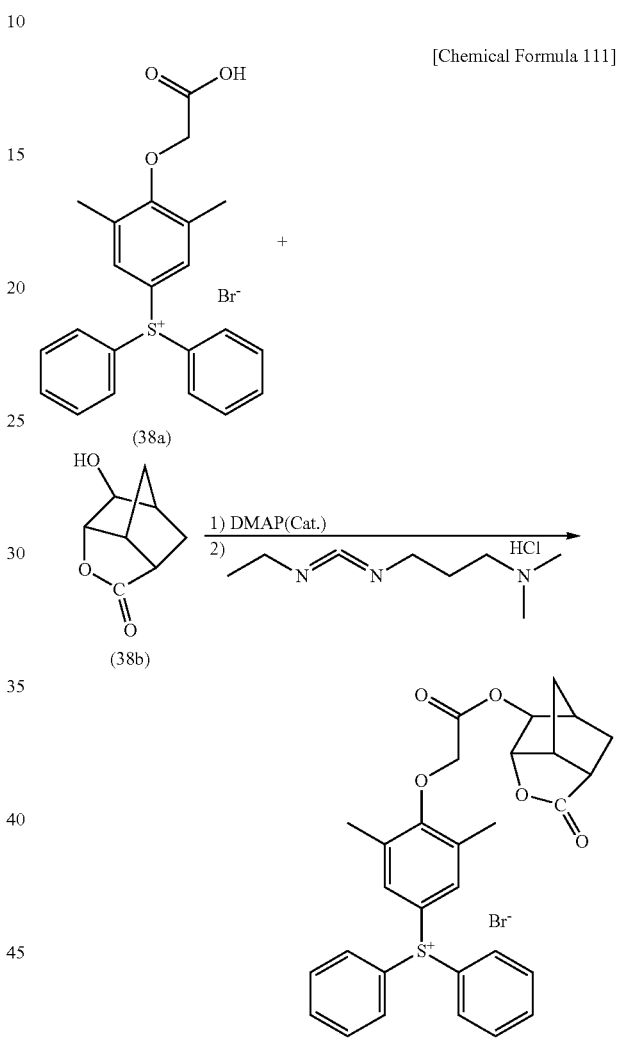

Synthesis Example 2-39

Compound: Synthesis of PAG-39

The same operations as those described in the aforementioned Synthesis Example 2-2 were carried out with the exception that a bromine salt represented in chemical formula shown below was used instead of the compound represented by chemical formula E, thereby obtaining an objective compound (PAG-39). The bromine salt represented in chemical formula shown below was synthesized in accordance with Japanese Unexamined Patent Application, First Publication No. 2009-019028.

The obtained compound was analyzed by NMR, and the structure thereof was identified based on the results shown below.

¹H-NMR (DMSO-d6, 400 MHz): δ (ppm)=7.80-7.92 (m, 10H, ArH), 7.67 (s, 2H, ArH), 4.66 (s, 2H, cation —OCH$_2$), 4.50-4.54 (m, 4H, OCH$_2$CH$_2$O), 3.57 (d, 1H, CH$_2$SO$_2$), 3.36 (s, 1H, CH$_2$SO$_2$), 2.37 (s, 6H, ArCH$_3$), 2.24-2.34 (m, 2H, camphor), 2.13-2.16 (m, 2H, cyclohexyl), 2.07 (t, 1H, camphor), 1.92-1.99 (m, 4H, camphor+cyclohexyl), 1.56-1.62 (m, 1H, camphor), 1.14-1.55 (m, 9H, camphor+cyclohexyl), 1.04 (s, 3H, CH$_3$), 0.84 (m, 6H, anion —CH$_3$+cyclohexyl —CH$_3$)

¹⁹F-NMR (DMSO-d6, 376 MHz): δ (ppm)=−106.5

[Chemical Formula 112]

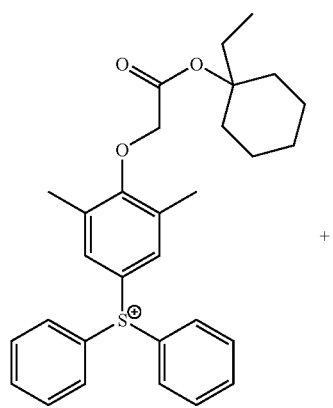

Br⁻

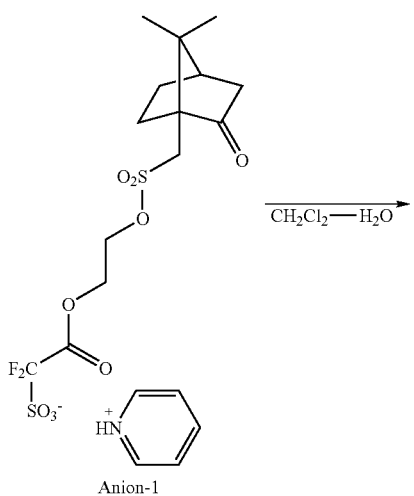

Anion-1

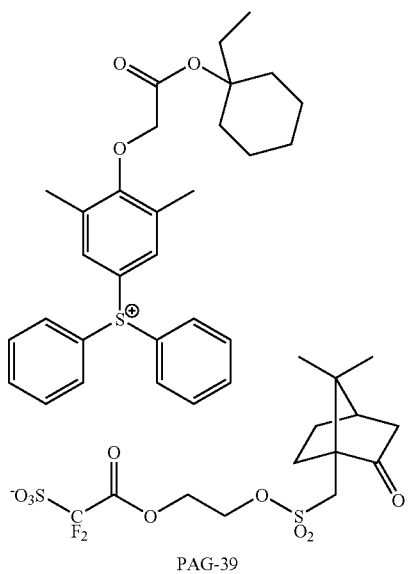

PAG-39

Synthesis Example 2-40

Compound: Synthesis of PAG-40

The same operations as those described in the aforementioned Synthesis Example 2-2 were carried out with the exception that a bromine salt represented in chemical formula shown below was used instead of the compound represented by chemical formula E, thereby obtaining an objective compound (PAG-40).

The obtained compound was analyzed by NMR, and the structure thereof was identified based on the results shown below.

¹H-NMR (DMSO-d6, 400 MHz): δ (ppm)=8.44 (d, 1H, ArH), 8.22 (m, 2H, ArH), 7.73-7.89 (m, 13H, ArH), 7.50 (d, 1H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

¹⁹F-NMR (DMSO-d6, 376 MHz): δ (ppm)=−106.5

[Chemical Formula 113]

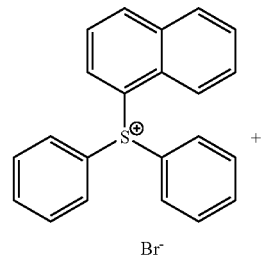

Br⁻

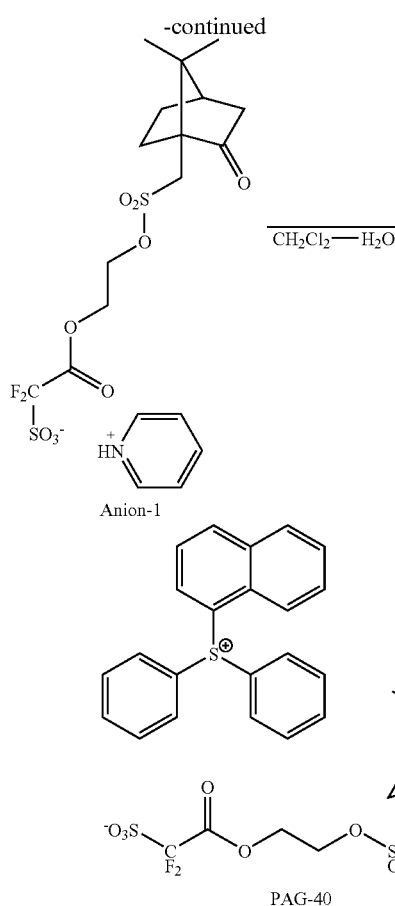

PAG-40

Synthesis Example 2-41

Compound: Synthesis of PAG-41

The same operations as those described in the aforementioned Synthesis Example 2-2 were carried out with the exception that a bromine salt represented in chemical formula shown below was used instead of the compound represented by chemical formula E, thereby obtaining an objective compound (PAG-41).

The obtained compound was analyzed by NMR, and the structure thereof was identified based on the results shown below.

$^1$H-NMR (DMSO-d6, 400 MHz): δ (ppm)=8.55 (d, 2H, ArH), 8.38 (d, 2H, ArH), 8.32 (d, 2H, ArH), 8.03 (d, 2H, ArH), 7.93-7.97 (m, 1H, ArH), 7.82-7.88 (m, 8H, ArH), 7.55 (d, 2H, ArH), 4.50-4.54 (m, 4H, OCH$_2$CH$_2$O), 3.57 (d, 1H, CH$_2$SO$_2$), 3.36 (s, 1H, CH$_2$SO$_2$), 2.24-2.34 (m, 2H, camphor), 2.07 (t, 1H, camphor), 1.92-1.99 (m, 2H, camphor), 1.56-1.62 (m, 1H, camphor), 1.42-1.45 (m, 1H, camphor), 1.04 (s, 3H, CH$_3$), 0.84 (s, 3H, CH$_3$)

$^{19}$F-NMR (DMSO-d6, 376 MHz): δ (ppm)=−106.5

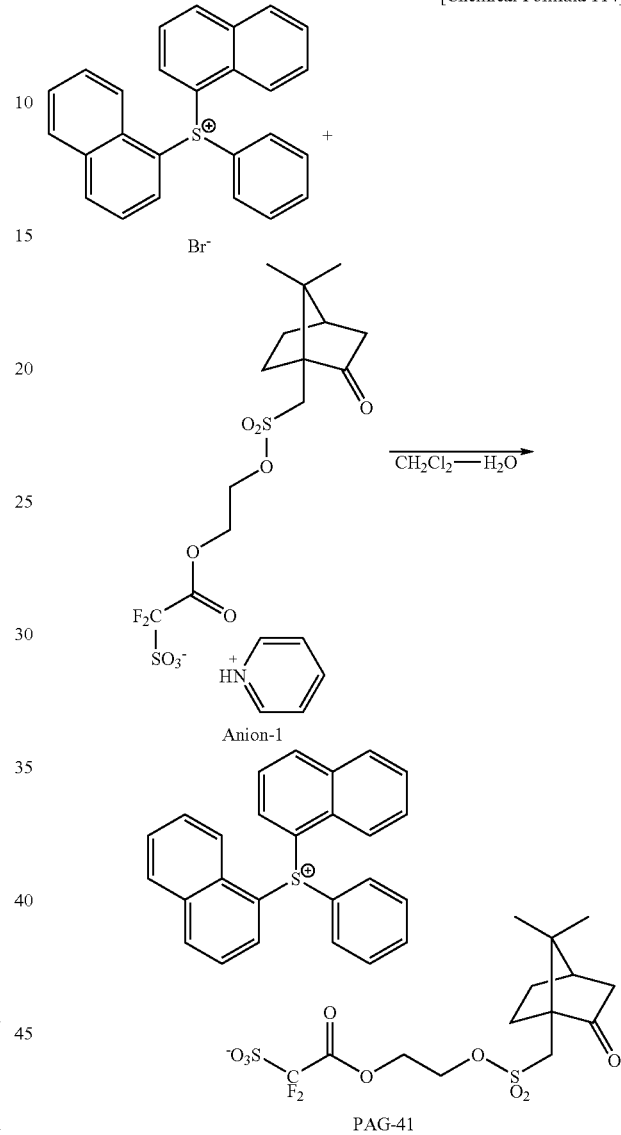

PAG-41

Examples 1 to 4, Comparative Example 1

The components shown in Table 1 were mixed together and dissolved to obtain positive resist composition solutions.

TABLE 1

|  | Component (A) | Component (B) | Component (D) | Component (E) | Component (S) | |
|---|---|---|---|---|---|---|
| Example 1 | (A)-1 | (B)-1 | (D)-1 | (E)-1 | (S)-1 | (S)-2 |
|  | [100] | [9.86] | [1.20] | [1.32] | [10] | [2,200] |
| Example 2 | (A)-1 | (B)-2 | (D)-1 | (E)-1 | (S)-1 | (S)-2 |
|  | [100] | [12.45] | [1.20] | [1.32] | [10] | [2,200] |
| Example 3 | (A)-1 | (B)-5 | (D)-1 | (E)-1 | (S)-1 | (S)-2 |
|  | [100] | [13.20] | [1.20] | [1.32] | [10] | [2,200] |
| Example 4 | (A)-1 | (B)-6 | (D)-1 | (E)-1 | (S)-1 | (S)-2 |
|  | [100] | [12.20] | [1.20] | [1.32] | [10] | [2,200] |

TABLE 1-continued

| | Component (A) | Component (B) | Component (D) | Component (E) | Component (S) | |
|---|---|---|---|---|---|---|
| Comparative Example 1 | (A)-1 [100] | (B')-1 [8.00] | (D)-1 [1.20] | (E)-1 [1.32] | (S)-1 [10] | (S)-2 [2,200] |

In Table 1, the reference characters indicate the following. Further, the values in brackets [ ] in Table 1 indicate the amount (in terms of parts by weight) of the component added. The amount of the component (B) added in Example 1 is the molar equivalent to the amount of the component (B) added in Comparative Example 1.

(A)-1: a copolymer represented by chemical formula (A)-1 shown below (wherein l/m/n=45/35/20 (molar ratio)) with Mw=7,000 and Mw/Mn=1.8

(B)-1: a compound represented by chemical formula (B)-1 shown below (i.e., PAG-1 obtained in Synthesis Example 2-1)

(B)-2: a compound represented by chemical formula (B)-2 shown below (i.e., PAG-2 obtained in Synthesis Example 2-2)

(B)-5: a compound represented by chemical formula (B)-5 shown below (i.e., PAG-5 obtained in Synthesis Example 2-5)

(B)-6: a compound represented by chemical formula (B)-6 shown below (i.e., PAG-6 obtained in Synthesis Example 2-6)

(B')-1: a compound represented by chemical formula (B')-1 shown below (D)-1: tri-n-pentylamine (E)-1: salicylic acid (5)-1: γ-butyrolactone (S)-2: PGME

[Chemical Formula 115]

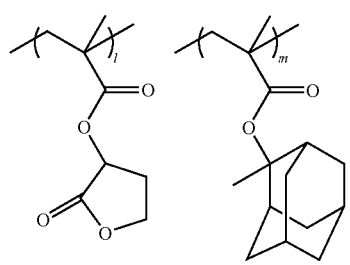

(A)-1

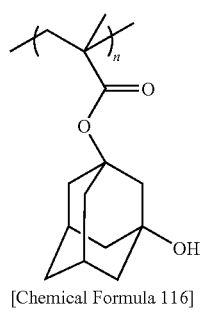

[Chemical Formula 116]

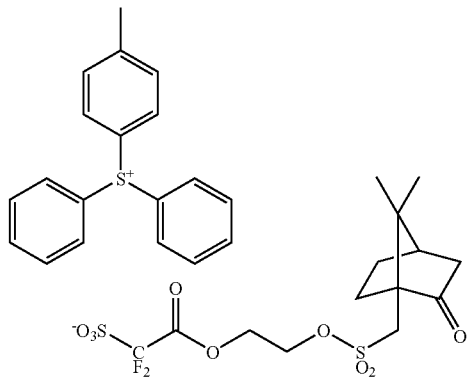

(B)-1

(B')-1

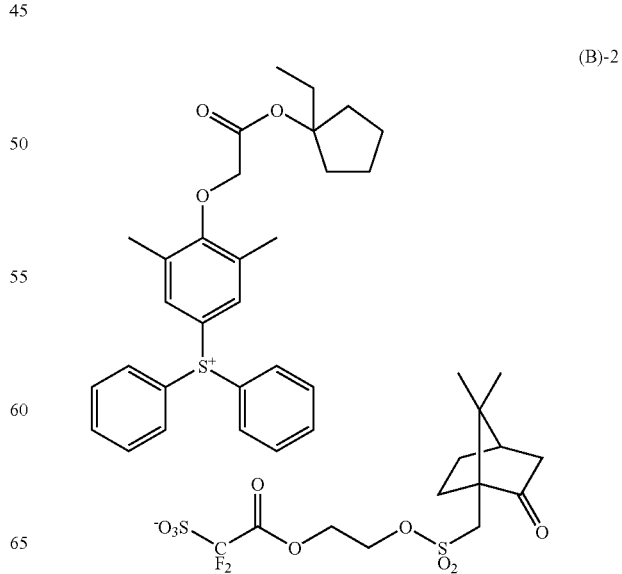

(B)-2

-continued

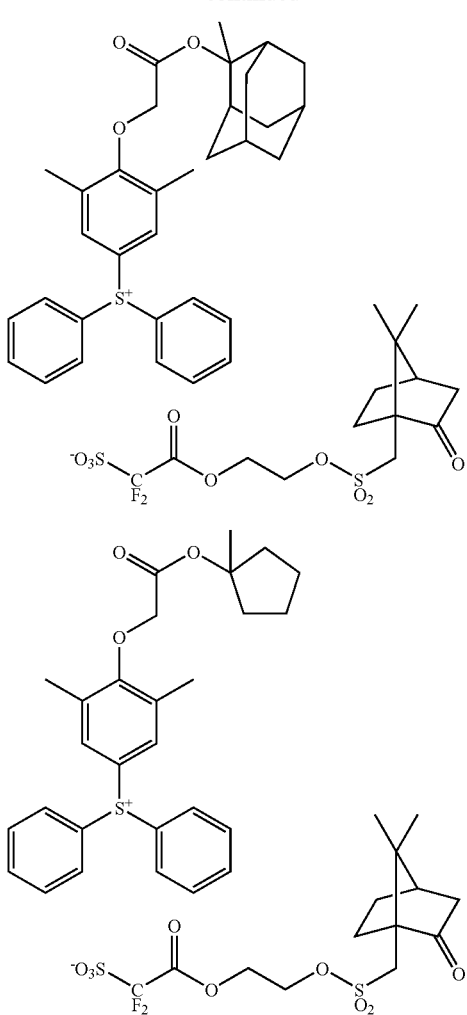

Using the obtained resist compositions, the following evaluations were conducted.
[Formation of Resist Pattern]
An organic antireflection film composition (product name: ARC29, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 82 nm. Then, each of the resist compositions obtained above was applied onto the antireflection film using a spinner, and was then prebaked (PAB) on a hotplate at 110° C. for 60 seconds and dried, thereby forming a resist film having a film thickness of 150 nm.

Subsequently, the resist film was selectively irradiated with an ArF excimer laser (193 nm) through a mask pattern targeting a line and space pattern (hereafter referred to as "L/S pattern") having a line width of 120 nm and a pitch of 240 nm, using an ArF exposure apparatus NSR-S302 (manufactured by Nikon Corporation, NA (numerical aperture)=0.60, ⅔ annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was washed for 30 seconds with pure water, followed by drying by shaking.

As a result, in each of the examples, an L/S pattern having a line width of 120 nm and a pitch of 240 nm was formed on the resist film.
[Evaluation of Pattern Shape]
The cross sectional shape of the L/S pattern having a line width of 120 nm and a pitch of 240 nm formed as described in the above [Formation of resist pattern] section was observed using a scanning electron microscope (SEM) (product name: S-9220, manufactured by Hitachi, Ltd.).

As a result, the resist pattern obtained in Comparative Example 1 had a line with a rounded top, whereas the resist pattern obtained in Example 1 had an excellent shape exhibiting a high level of rectangularity in the cross sectional shape of the line top portion.
[Evaluation of Mask Error Factor (MEF)]
L/S patterns were formed in the same manner as described in the above [Formation of resist pattern] section with the exception that the exposure dose was fixed to the above-mentioned Eop, and a mask pattern targeting an L/S pattern having a line width of 130 nm and a pitch of 260 nm and a mask pattern targeting an L/S pattern having a line width of 120 nm and a pitch of 260 nm were used.

With respect to the formed L/S patterns, the line width was measured using a SEM and the MEF was determined by the following formula. The results are shown in Table 2.

$$MEF = |CD_{130} - CD_{120}| / |MD_{130} - MD_{120}|$$

In this formula, $CD_{130}$ and $CD_{120}$ represent the respective line widths (nm) of the actual L/S patterns respectively formed using the mask pattern targeting a line width of 130 nm and the mask pattern targeting a line width of 120 nm, and $MD_{130}$ and $MD_{120}$ represent the respective target line widths (nm), meaning $MD_{130}$=130 and $MD_{120}$ 120. The closer the MEF value is to 1, the better the mask reproducibility of the resist pattern formed.
[Evaluation of EL Margin]
L/S patterns with a target dimension of a line width of 120 nm and a pitch of 240 nm were formed by the same procedure as described in the above [Formation of resist pattern] section with the exception that the exposure dose was changed.

The exposure dose with which an L/S pattern with lines having a target dimension (line width of 120 nm)±5% (i.e., 114 to 126 nm) was formed was determined, and the EL margin (unit: %) was determined by the following formula. The results are shown in Table 2.

$$EL\ margin\ (\%) = (|E1 - E2| / Eop) \times 100$$

[In the formula, E1 represents the exposure dose (mJ/cm²) for forming an L/S pattern having a line width of 114 nm, and E2 represents the exposure dose (mJ/cm²) for forming an L/S pattern having a line width of 126 nm.]

TABLE 2

|  | Example 1 | Example 2 | Example 3 | Example 4 | Comparative Example 1 |
| --- | --- | --- | --- | --- | --- |
| MEF | 2.33 | 2.10 | 2.21 | 2.08 | 2.67 |
| EL (%) | 8.76 | 9.05 | 8.50 | 9.00 | 6.54 |

From the results shown above, it was confirmed that the resist compositions obtained in Examples 1 to 4 exhibited excellent lithography properties.

What is claimed is:
1. A resist composition comprising:
a base material component (A) which exhibits changed solubility in an alkali developing solution under action of acid; and an acid generator component (B) which generates acid upon exposure, said acid generator component (B) including an acid generator (B1) consisting of a compound represented by general formula (b1-1) shown below:

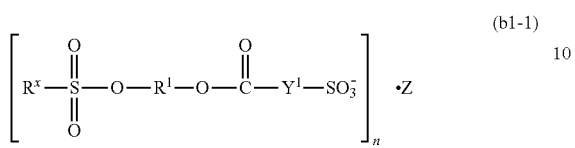

wherein $R^x$ represents a hydrocarbon group which may have a hetero atom; $R^1$ represents a divalent linking group; $Y^1$ represents an alkylene group of 1 to 4 carbon atoms or a fluorinated alkylene group of 1 to 4 carbon atoms; n represents an integer of 1 to 3; and Z represents an organic cation (exclusive of an amine ion and a quaternary ammonium ion) having a valence of n.

2. The resist composition according to claim 1,
wherein said base material component (A) is a base material component which exhibits increased solubility in an alkali developing solution under action of acid.

3. The resist composition according to claim 2,
wherein said base material component (A) comprises a resin component (A1) which exhibits increased solubility in an alkali developing solution under action of acid, and
said resin component (A1) comprises a structural unit (a1) derived from an acrylate ester containing an acid dissociable, dissolution inhibiting group.

4. The resist composition according to claim 3,
wherein said resin component (A1) further comprises a structural unit (a2) derived from an acrylate ester containing a lactone-containing cyclic group.

5. The resist composition according to claim 3,
wherein said resin component (A1) further comprises a structural unit (a3) derived from an acrylate ester containing a polar group-containing aliphatic hydrocarbon group.

6. The resist composition according to claim 1, which further comprises a nitrogen-containing organic compound (D).

7. A method of forming a resist pattern, comprising:
applying a resist composition of claim 1 to a substrate to form a resist film on the substrate;
subjecting said resist film to exposure; and
subjecting said resist film to alkali developing to form a resist pattern.

* * * * *

UNITED STATES PATENT AND TRADEMARK OFFICE
CERTIFICATE OF CORRECTION

PATENT NO. : 8,415,082 B2  Page 1 of 4
APPLICATION NO. : 12/765590
DATED : April 9, 2013
INVENTOR(S) : Yoshiyuki Utsumi et al.

It is certified that error appears in the above-identified patent and that said Letters Patent is hereby corrected as shown below:

In the Specification

In Column 2, Line 27, Change "241385" to --241385.--.

In Column 2, Line 29, Change "037888" to --037888.--.

In Column 12, Line 41, Change "N=or" to --N=, or--.

In Column 12, Line 44, Change "isooxazol," to --isoxazole,--.

In Column 18, Line 36, Change "hydroxylalkyl" to --hydroxyalkyl--.

In Column 19, Line 17, Change "$(CF_2)_e$—" to --$(CF_2)_f$— --.

In Column 28, Line 23, Change "$R^{1'''}$" to --$R^{1''}$--.

In Column 30, Line 3, Change "C—)" to --C—),--.

In Column 32, Line 20 (Approx.), Change "quinoxazoline" to --quinazoline--.

In Column 32, Line 37, Change "thereof" to --thereof.--.

In Column 35, Line 30, Change "pyrrazole," to --pyrazole,--.

In Column 35, Line 36, Change "benztriazole," to --benzotriazole,--.

In Column 37, Line 2, Change "analysis," to --analysis.--.

In Column 49, Line 41, Change "$R^{h}$" to --$R^{1'}$--.

In Column 49, Line 58, Change "$R^{h}$," to --$R^{1'}$,--.

In Column 51, Line 30, Change "(a10-1)" to --(a1-0-1)--.

Signed and Sealed this
Twenty-eighth Day of January, 2014

Michelle K. Lee
*Deputy Director of the United States Patent and Trademark Office*

In Column 54, Line 30, Change "$R^h$," to --$R^{1\prime}$,--.

In Column 95, Lines 40-47 (Approx.),

Change " 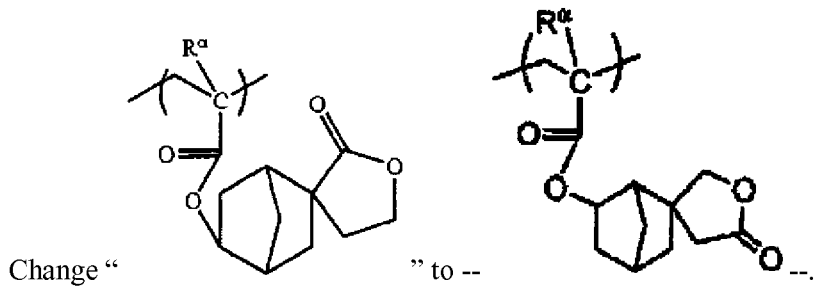 " to -- --.

In Column 95, Lines 48-56 (Approx.),

Change " 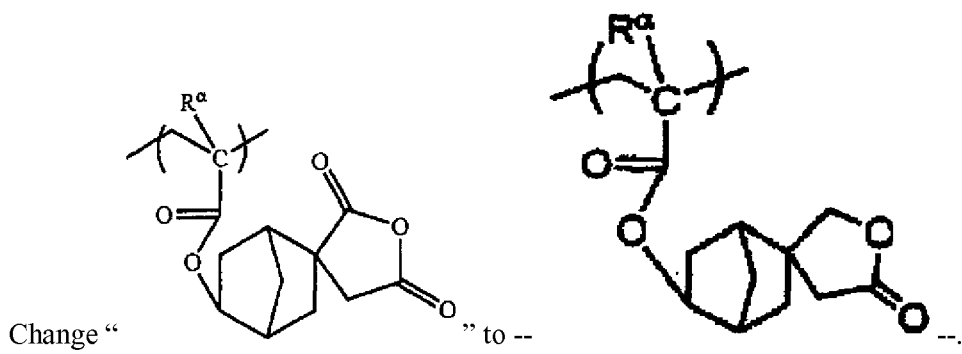 " to -- --.

In Column 103, Line 22, Change "(4' hydroxyphenyl)" to --(4'-hydroxyphenyl)--.

In Column 104, Line 59, Change "$R^{4\prime\prime}$" to --$R^{4\prime\prime}$--.

In Column 107, Line 11, Change "in" to --In--.

In Column 110, Line 39, Change "diazornethanes," to --diazomethanes,--.

In Column 111, Line 28, Change "laurildiethanolamine." to --lauryldiethanolamine.--.

In Column 115, Line 17, Change "at" to --as--.

In Column 119, Line 46 (Approx.), Change "NMR." to --NMR--.

In Column 126, Line 19, Change "NMR." to --NMR--.

In Column 131, Line 39, Change "NMR." to --NMR--.

CERTIFICATE OF CORRECTION (continued)
U.S. Pat. No. 8,415,082 B2

In Column 133, Lines 1-16 (Approx.),

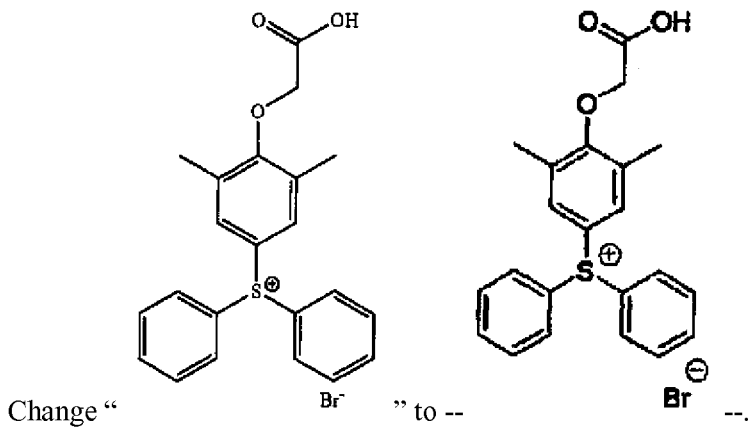

Change " " to -- --.

In Column 135, Lines 11-25 (Approx.),

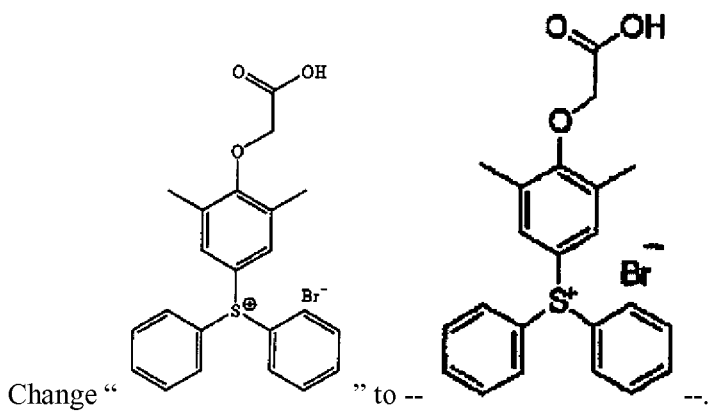

Change " " to -- --.

In Column 140, Line 54 (Approx.), Change "NMR." to --NMR--.

In Column 153, Lines 37-52 (Approx.),

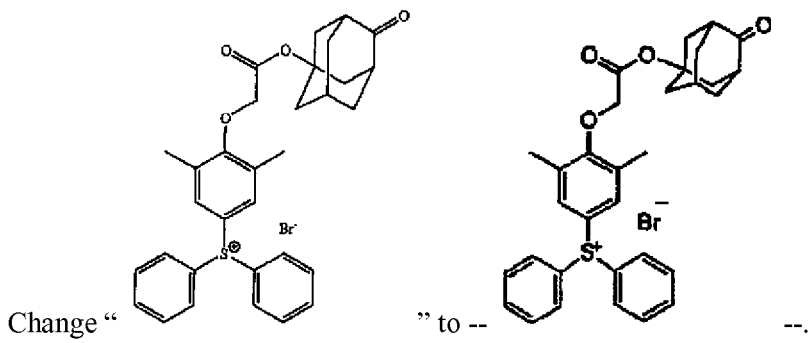

Change " " to -- --.

In Column 154, Line 3, Change "31-1," to --3H,--.

In Column 165, Line 57, Change "thioxanten-" to --thioxanthene- --.

In Column 167, Line 60 (Approx.), Change "NMR." to --NMR--.

In Column 169, Line 61, Change "CH₂CH₂O+" to --CH₂O+--.

In Column 171, Line 25, Change "NMR." to --NMR--.

In Column 172, Line 41 (Approx.), Change "1311," to --13H,--.

In Column 173, Line 62, Change "diphenylsufoxide" to --diphenylsulfoxide--.

In Column 175, Line 65, Change "adamantylacecyl" to --adamantylacetyl--.

In Column 183, Line 33 (Approx.), Change "(5)-1:" to --(S)-1:--.

In the Claims

In Column 187, Lines 8-14 (Approx.), In Claim 1,

Change " 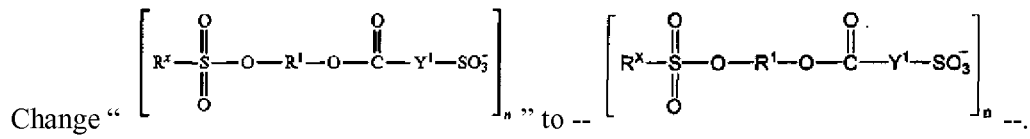 --.

At Column 187, Line 16, In Claim 1, Change "$R^x$" to --$R^X$--.